US009663495B2

(12) United States Patent
Han et al.

(10) Patent No.: US 9,663,495 B2
(45) Date of Patent: May 30, 2017

(54) TRIAZOLONE DERIVATIVES OR SALTS THEREOF AND PHARMACEUTICAL COMPOSITION COMPRISING THE SAME

(71) Applicant: YUHAN CORPORATION, Seoul (KR)

(72) Inventors: Tae-Dong Han, Yongin-si (KR); Eun-Hye Jung, Yongin-si (KR); Chung-Ho Yi, Seoul (KR); Byoung-Moon Lee, Yongin-si (KR); Yoo-Hoi Park, Suwon-si (KR); Dong-Hoon Lee, Suwon-si (KR); Jong-Ho Kang, Seoul (KR); Na-Yeon Yang, Hwaseong-si (KR); Do-Hoon Kim, Yongin-si (KR); Kwan-Hoon Hyun, Incheon (KR); Kaap-Joo Park, Seoul (KR); Chun-Ho Lee, Seoul (KR); Su-Youn Nam, Seoul (KR)

(73) Assignee: YUHAN CORPORATION, Seoul (KR)

( * ) Notice: Subject to any disclaimer, the term of this patent is extended or adjusted under 35 U.S.C. 154(b) by 26 days.

(21) Appl. No.: 14/786,837

(22) PCT Filed: Apr. 22, 2014

(86) PCT No.: PCT/KR2014/003480
§ 371 (c)(1),
(2) Date: Oct. 23, 2015

(87) PCT Pub. No.: WO2014/175621
PCT Pub. Date: Oct. 30, 2014

(65) Prior Publication Data
US 2016/0068515 A1  Mar. 10, 2016

(30) Foreign Application Priority Data

Apr. 25, 2013 (KR) .................. 10-2013-0045985

(51) Int. Cl.
| | | |
|---|---|---|
| C07D 401/10 | (2006.01) |
| C07D 401/14 | (2006.01) |
| C07D 403/04 | (2006.01) |
| C07C 403/10 | (2006.01) |
| C07C 403/14 | (2006.01) |
| C07D 405/04 | (2006.01) |
| C07D 405/06 | (2006.01) |
| C07D 413/14 | (2006.01) |
| C07D 249/12 | (2006.01) |
| C07D 403/10 | (2006.01) |
| C07D 403/14 | (2006.01) |
| C07D 405/14 | (2006.01) |

(52) U.S. Cl.
CPC ......... *C07D 401/14* (2013.01); *C07D 249/12* (2013.01); *C07D 401/10* (2013.01); *C07D 403/04* (2013.01); *C07D 403/10* (2013.01); *C07D 403/14* (2013.01); *C07D 405/04* (2013.01); *C07D 405/06* (2013.01); *C07D 405/14* (2013.01); *C07D 413/14* (2013.01)

(58) Field of Classification Search
None
See application file for complete search history.

(56) References Cited

PUBLICATIONS

Sheng et al., "Design and synthesis of novel triazole antifungal derivatives by structure-based bioisosterism", European Journal of Medicinal Chemistry, vol. 46, pp. 5276-5282, (2011).
Shah, "GPR119 agonists: A promising new approach for the treatment of type 2 diabetes and related metabolic disorders", Current Opinion in Drug Discovery & Development, vol. 12, No. 4, pp. 519-532, (2009).
Sears et al., "Mechanisms of human insulin resistance and thiazolidinedione-mediated insulin sensitization", PNAS, vol. 106, No. 44, pp. 18745-18750, (2009).
Lauffer et al., "GPR119 Is Essential for Oleoylethanolamide-Induced Glucagon-Like Peptide-1 Secretion From the Intestinal Enteroendocrine L-Cell", Diabetes, vol. 58, pp. 1058-1066, (2009).
Matias et al., "Role and regulation of acylethanolamides in energy balance: focus on adipocytes and β-cells", British Journal of Pharmacology, vol. 152, pp. 676-690, (2007).
Hansen et al., "N-acylethanolamines, anandamide and food intake", Biochemical Pharmacology, vol. 78, pp. 553-560, (2009).
Oshima et al., "Novel GPR119 agonist AS1669058 potentiates insulin secretion from rat islets and has potent anti-diabetic effects in ICR and diabetic db/db mice", Life Sciences, vol. 92, pp. 167-173, (2013).
Ansarullah et al., "Stimulating β-Cell Regeneration by Combining a GPR119 Agonist with a DDP-IV Inhibitor", PLOS ONE, vol. 8, Issue 1, e53345, 11 pages, (2013).
Gao et al., "Stimulating beta cell replication and improving islet graft function by GPR119 agonists", European Society for Organ Transplantation, vol. 24, pp. 1124-1134, (2011).

*Primary Examiner* — Alicia L Otton
(74) *Attorney, Agent, or Firm* — Vorys, Sater, Seymour & Pease LLP; Mih Suhn Koh

(57) ABSTRACT

Provided is a triazolone derivative or its pharmaceutically acceptable salt, a process for the preparation thereof, and a pharmaceutical composition comprising the same. The triazolone derivative or its pharmaceutically acceptable salt can effectively activate GPR119; and therefore be usefully applied for preventing or treating diabetes mellitus.

13 Claims, No Drawings

TRIAZOLONE DERIVATIVES OR SALTS THEREOF AND PHARMACEUTICAL COMPOSITION COMPRISING THE SAME

TECHNICAL FIELD

The present invention relates to a triazolone derivative or its pharmaceutically acceptable salt, a process for the preparation thereof, and a pharmaceutical composition comprising the same.

BACKGROUND ART

Diabetes mellitus is classified into type 1 diabetes mellitus and type 2 diabetes mellitus. About 95% of the patients suffer from type 2 diabetes mellitus. For treating diabetes mellitus and/or complications thereof, there have been used various agents, for example, agents for stimulating insulin secretion (such as sulfonylurea derivatives, meglitinide derivatives, etc.), agents for improving insulin resistance (such as biguanide derivatives, thiazolidinedione derivatives, etc.), agents for inhibiting carbohydrate digestion (such as alpha-glucosidase inhibitors, etc.), incretins (such as GLP-1 analogs, DPP-4 inhibitors, etc.) (Current Opinion in Drug Discovery & Development, 2009, 12). However, it is well-known in the art that the agents for stimulating insulin secretion, which are most commonly used, cause side effects such as hypoglycemia, weight gain, etc. In addition, it have been reported that the biguanide derivatives show side effects such as lactic acidosis, etc.; and that the thiazolidinedione derivatives show side effects such as hepatic toxicity, heart failure, etc. (D. D. Sears et al., Proc Natl Acad Sci USA 2009; 106: 18745-18750).

Meanwhile, G protein-coupled receptor also known as GPR119 is mainly expressed in pancreatic islets and in the gastrointestinal tract. GPR119 activation mediates insulin secretion through direct action on pancreatic β-cells; and stimulates the glucagon-like peptide-1 (GLP-1) secretion in the intestinal L-cells, thereby improving glucose stimulated insulin secretion (GSIS) (Lina M. L. et al., Diabetes 2009; 58: 1058-1066). Therefore, it is expected that an agent for activating GPR119 increases glucose homeostasis, thereby being able to be used as a potential agent for treating diabetes mellitus as well as inhibiting food intake and weight gain. In fact, there are various reports that GPR119 agonists show fat loss and weight loss through various obesity animal models (Matias I. et al., Br J Pharmacol 2007; 152(2): 676-690, Hansen H. S. et al., Biochemical Pharmacology 78 (2009) 553-560, Hiroyuki O. et al., Life sciences 92 (2013) 167-173).

The stimulation of insulin secretion by GPR119 activation can avoid potential hypoglycemia, since it makes glucose-dependent insulin secretion possible through stimulating the formation of cyclic adenosine monophosphate (cAMP) in the β-cells. The GLP-1 secretion and cAMP activation by continuous GPR119 activation increase the islet beta cell mass, which improves self-insulin production, thereby making it possible to treat insulin-dependent diabetes mellitus (Ansarullah et al., Plos one 2013; 8(1):1-11, Gao J. et al., Transplant International 2011 European Society for Organ Transplantation 24 (2011) 1124-1134). Therefore, it is expected that GPR119 agonists may be continuously used as an agent for treating diabetes mellitus for long duration, while minimizing the side effects (e.g., hypoglycemia, weight gain) of conventional hypoglycemic agents or anti-diabetic agents.

DISCLOSURE OF INVENTION

Technical Problem

The present inventors found that a triazolone derivative or its pharmaceutically acceptable salt remarkably activates GPR119, thereby being useful for preventing or treating diabetes mellitus.

Therefore, the present invention provides said triazolone derivative or its pharmaceutically acceptable salt, a process for the preparation thereof, and a pharmaceutical composition comprising the same.

Solution to Problem

In accordance with an aspect of the present invention, there is provided a triazolone derivative or its pharmaceutically acceptable salt having a hypoglycemic activity through GPR119 activation.

According to another aspect of the present invention, there is provided a process for preparing the triazolone derivative or its pharmaceutically acceptable salt.

According to still another aspect of the present invention, there is provided a pharmaceutical composition for preventing or treating diabetes mellitus comprising the triazolone derivative or its pharmaceutically acceptable salt as an active ingredient.

Advantageous Effects of Invention

The compound of the present invention, i.e., the triazolone derivative or its pharmaceutically acceptable salt, effectively activates GPR119. Therefore, the triazolone derivative or its pharmaceutically acceptable salt may be usefully applied for preventing or treating diabetes mellitus.

BEST MODE FOR CARRYING OUT THE INVENTION

As used herein, the term "alkyl" refers to a straight or branched aliphatic hydrocarbon radical. For example, $C_1$~$C_6$ alkyl means a straight or branched aliphatic hydrocarbon having 1 to 6 carbon atoms, such as methyl, ethyl, propyl, n-butyl, n-pentyl, n-hexyl, isopropyl, isobutyl, sec-butyl, tert-butyl, neopentyl, and isopentyl.

The term "alkoxy" refers to a radical formed by substituting the hydrogen atom of a hydroxyl group with an alkyl. For example, $C_1$~$C_6$ alkoxy includes methoxy, ethoxy, propoxy, n-butoxy, n-pentyloxy, isopropoxy, sec-butoxy, tert-butoxy, neopentyloxy, and isopentyloxy.

The term "aryl" refers to a functional group derived from an aromatic ring with delocalized pi electron clouds. The "aryl" includes, for example, a $C_6$~$C_{12}$ hydrocarbon-ring such as phenyl, naphthyl, and biphenyl.

The term "heteroaryl" refers to a 5- to 12-membered aromatic radical having 1 to 3 hetero atoms selected from nitrogen (N) atom, oxygen (O) atom, and sulfur (S) atom, including a 5- or 6-membered monocyclic heteroaryl radical and a bicyclic heteroaryl radical formed by fusing the 5- or 6-membered monocyclic heteroaryl radical with benzene or pyridine. For example, the monocyclic heteroaryl includes thiazole, pyrazole, oxazole, imidazole, pyrrole, furan, thiophene, isothiazole, isoxazole, triazole, thiadiazole, tetrazole, oxadiazole, triazine, pyridine, pyridazine, pyrimidine, pyrazine, etc. And also, the bicyclic heteroaryl includes benzothiazole, bezoxazole, benzimidazole, benzofuran, benzothiophene, benzisoxazole, indole, indoline, quinoline, isoquinoline, quinazoline, imidazopyridine, oxazolopyridine, etc. Preferably, the "heteroaryl" may be 5- or 6-membered heteroaryl radical, such as pyridine, pyrimidine, oxadiazole, etc.

The term "hetercycle" refers to a 3- or 12-membered mono- or poly-cyclic ring having one or more, preferably 1 to 4, same or different hetero atoms selected from nitrogen (N) atom, oxygen (O) atom, and sulfur (S) atom, but not having an aromatic ring. For example, the "hetercycle" includes pyrrolidine, imidazolin, imidazolidine, pyrazoline, pyrazolidine, piperidine, morpholine, piperazine, tetrahydrofuran, tetrahydropyrimidin-2(1H)-one, imidazolidin-2-one, etc. Preferably, the "hetercycle" may be 5- or 6-membered monocyclic ring, such as pyrrolidine, morpholine, piperazine, tetrahydrofuran, piperidine, etc.

The present invention provides a compound of Formula 1 or its pharmaceutically acceptable salt:

<Formula 1>

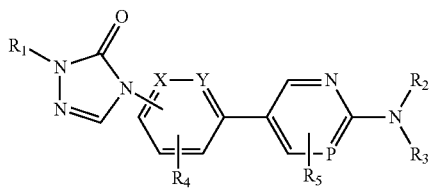

wherein, $R_1$ is hydrogen; a $C_1$~$C_6$ alkyl group optionally substituted with one or more substituents selected from the group consisting of hydroxy, halogen, $C_1$~$C_6$ alkoxy optionally substituted with $C_1$~$C_6$ alkoxy, $C_3$~$C_6$ cycloalkyl, cyano, 3- to 12-membered heterocyclic optionally substituted with one or more $C_1$~$C_6$ alkyls, —$NR_6R_7$, and

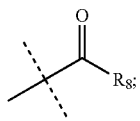

a $C_1$~$C_6$ alkylcarbonyl group; a $C_1$~$C_6$ alkoxycarbonyl group; or a 3- to 12-membered heterocyclic group optionally substituted with one or more substituents selected from the group consisting of $C_1$~$C_6$ alkyl, $C_2$~$C_6$ alkynyl, $C_1$~$C_6$ alkoxy, $C_3$~$C_6$ cycloalkyl, $C_1$~$C_6$ alkoxycarbonyl, $C_1$~$C_6$ alkylcarbonylamino, and $C_1$~$C_6$ alkylsulfonyl, $R_2$ is hydrogen or a $C_1$~$C_6$ alkyl group, $R_3$ is a $C_1$~$C_6$ alkyl group; or is cyclized with $R_2$ to form a 3- to 12-membered heterocyclic group, wherein the heterocyclic group may be optionally substituted with one or more substituents selected from the group consisting of $C_1$~$C_6$ alkyl optionally substituted with one or more halogens;

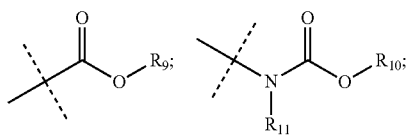

-continued

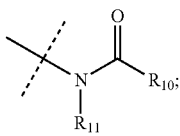

—$NR_{12}R_{13}$; 5- to 12-membered heteroaryl; and 3- to 12-membered heterocyclic (wherein, the heteroaryl or heterocyclic moiety may be optionally substituted with one or more $C_1$~$C_6$ alkyls optionally substituted with one or more halogens), $R_4$ and $R_5$ are, independently each other, hydrogen; a hydroxy group; a halogen group; a cyano group; a $C_1$~$C_6$ alkyl group optionally substituted with one or more halogens; a $C_1$~$C_6$ alkoxy group; or a mono- or di-$C_1$~$C_6$ alkylamino group, X and P are, independently each other, N or $CR_{14}$, Y is $CR_{14}$ or N, $R_6$ and $R_7$ are, independently each other, hydrogen; a $C_1$~$C_6$ alkyl group optionally substituted with one or more substituents selected from the group consisting of hydroxy, $C_1$~$C_6$ alkoxy and $C_3$~$C_6$ cycloalkyl; a $C_1$~$C_6$ alkylcarbonyl group; a $C_1$~$C_6$ alkoxycarbonyl group; or a $C_1$~$C_6$ alkylsulfonyl group, $R_8$ is a hydroxy group, a $C_1$~$C_6$ alkoxy group, an amino group, or a 3- to 12-membered heterocyclic group, $R_9$ is a $C_1$~$C_6$ alkyl group or a $C_2$~$C_6$ alkenyl group, $R_{10}$ is a $C_1$~$C_6$ alkyl group optionally substituted with one or more substituents selected from the group consisting of halogen, $C_3$~$C_6$ cycloalkyl, $C_1$~$C_6$ alkoxy, and 5- to 12-membered heteroaryl; a $C_2$~$C_8$ alkenyl group; a $C_3$~$C_6$ cycloalkyl group; a 6- to 12-membered aryl group optionally substituted with one or more substituents selected from the group consisting of halogen, $C_1$~$C_6$ alkyl optionally substituted with one or more halogens, and $C_1$~$C_6$ alkoxy; a 5- to 12-membered heteroaryl group; or a 3- to 12-membered heterocyclic group (wherein, the heteroaryl group or the heterocyclic group may be optionally substituted with one or more substituents selected from the group consisting of $C_1$~$C_6$ alkyl, nitro, hydroxy, and oxo), $R_{11}$ is hydrogen, a $C_1$~$C_6$ alkyl group, or a $C_2$~$C_6$ alkenyl group, $R_{12}$ is a $C_1$~$C_6$ alkylsulfonyl group; a $C_3$~$C_6$ cycloalkylsulfonyl group; a di-$C_1$~$C_6$ alkylaminosulfonyl group; a 5- to 12-membered heteroaryl group optionally substituted with $C_1$~$C_6$ alkyl; or a 3- to 12-membered heterocyclic group, $R_{13}$ is a $C_1$~$C_6$ alkyl group, $R_{14}$ is hydrogen; a halogen group; a cyano group; a nitro group; a $C_1$~$C_6$ alkyl group optionally substituted with one or more halogens; a $C_1$~$C_6$ alkoxy group; or a mono- or di-$C_1$~$C_6$ alkylamino group.

In the compound of Formula 1 or its pharmaceutically acceptable salt of the present invention, $R_1$ may be hydrogen; a $C_1$~$C_6$ alkyl group optionally substituted with one or more substituents selected from the group consisting of hydroxy, $C_1$~$C_6$ alkoxy, cyano, 3- to 12-membered, preferably 5- to 6-membered heterocyclic optionally substituted with $C_1$~$C_6$ alkyl, —$NR_6R_7$, and

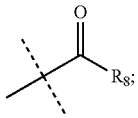

a $C_1$~$C_6$ alkoxycarbonyl group; or a 3- to 12-membered, preferably 5- to 6-membered heterocyclic group.

In the —$NR_6R_7$, $R_6$ and $R_7$ may be, independently each other, hydrogen; a $C_1$~$C_6$ alkyl group; a $C_1$~$C_6$ alkylcarbonyl group; a $C_1$~$C_6$ alkoxycarbonyl group; or a $C_1$~$C_6$ alkylsulfonyl group.

In the

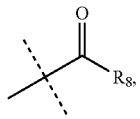

$R_8$ may be a $C_1$~$C_6$ alkoxy group, an amino group, or a 3- to 12-membered, preferably 5- to 6-membered heterocyclic group, In the compound of Formula 1 or its pharmaceutically acceptable salt of the present invention, $R_2$ and $R_3$ may be cyclized each other to form a 3- to 12-membered, preferably 5- to 6-membered heterocyclic group, wherein the heterocyclic group may be optionally substituted with one or more substituents selected from the group consisting of $C_1$~$C_6$ alkyl optionally substituted with one or more halogens;

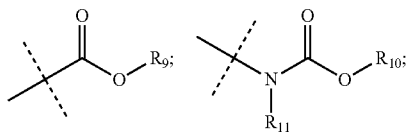

—$NR_{12}R_{13}$; and 5- to 12-membered, preferably 5- to 6-membered heteroaryl (wherein, the heteroaryl moiety may be optionally substituted with $C_1$~$C_6$ alkyl optionally substituted with one or more halogens).

Preferably, $R_2$ and $R_3$ may be cyclized each other to form a piperazinyl group or a piperidinyl group.

More preferably, $R_2$ and $R_3$ may cyclized each other to form a piperazinyl group or a piperidinyl group, and the piperazinyl group or the piperidinyl group may be optionally substituted with one or more substituents selected from the group consisting of $C_1$~$C_6$ alkyl optionally substituted with one or more halogens;

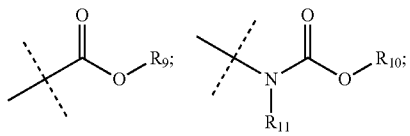

—$NR_{12}R_{13}$; and 5- to 12-membered heteroaryl selected from the group consisting of pyrimidyl, pyridyl, or 1,2,4-oxadiazolyl (wherein, the heteroaryl moiety may be optionally substituted with $C_1$~$C_6$ alkyl optionally substituted with one or more halogens).

In the

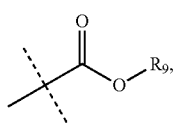

$R_9$ may be a $C_1$~$C_6$ alkyl group.

In the

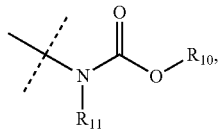

$R_{10}$ may be a $C_1$~$C_6$ alkyl group or a $C_2$~$C_6$ alkenyl group, and $R_{11}$ may be a $C_1$~$C_6$ alkyl group.

In the —$NR_{12}R_{13}$, $R_{12}$ may be a $C_1$~$C_6$ alkylsulfonyl group or a 5- to 12-membered, preferably 5- to 6-membered heteroaryl group optionally substituted with $C_1$~$C_6$ alkyl, and $R_{13}$ may be a $C_1$~$C_6$ alkyl group.

In the compound of Formula 1 or its pharmaceutically acceptable salt of the present invention, $R_4$ and $R_5$ may be, independently each other, hydrogen; a halogen group; a cyano group; or a $C_1$~$C_6$ alkyl group optionally substituted with one or more halogens.

In the compound of Formula 1 or its pharmaceutically acceptable salt of the present invention, X and P may be, independently each other, N or $CR_{14}$; and $R_{14}$ may be hydrogen or a halogen group.

In the compound of Formula 1 or its pharmaceutically acceptable salt of the present invention, Y may be $CR_{14}$; and $R_{14}$ may be hydrogen or a halogen group.

In an embodiment of the present invention, $R_1$ is hydrogen; a $C_1$~$C_6$ alkyl group optionally substituted with one or more substituents selected from the group consisting of hydroxy, $C_1$~$C_6$ alkoxy, cyano, 3- to 12-membered, preferably 5- to 6-membered heterocyclic optionally substituted with $C_1$~$C_6$ alkyl, —$NR_6R_7$, and

a $C_1$~$C_6$ alkoxycarbonyl group; or a 3- to 12-membered, preferably 5- to 6-membered heterocyclic group, $R_2$ and $R_3$ are cyclized each other to form a 3- to 12-membered, preferably 5- to 6-membered heterocyclic group, wherein the heterocyclic group may be optionally substituted with one or more substituents selected from the group consisting of $C_1$~$C_6$ alkyl optionally substituted with one or more halogens;

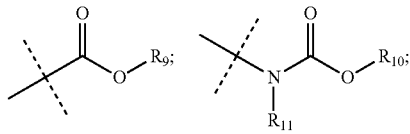

—$NR_{12}R_{13}$; and 5- to 12-membered, preferably 5- to 6-membered heteroaryl (wherein, the heteroaryl moiety may be optionally substituted with $C_1$~$C_6$ alkyl optionally substituted with one or more halogens), $R_4$ and $R_5$ are, independently each other, hydrogen; a halogen group; a cyano group; or a $C_1$~$C_6$ alkyl group optionally substituted with one or more halogens, X and P are, independently each other, N or $CR_{14}$, Y is $CR_{14}$, $R_6$ and $R_7$ are, independently each other, hydrogen; a $C_1$~$C_6$ alkyl group; a $C_1$~$C_6$ alkylcarbonyl group; a $C_1$~$C_6$ alkoxycarbonyl group; or a $C_1$~$C_6$ alkylsulfonyl group, $R_8$ is a $C_1$~$C_6$ alkoxy group, an amino group, or a 3- to 12-membered, preferably 5- to 6-membered heterocyclic group, $R_9$ is a $C_1$~$C_6$ alkyl group, $R_{10}$ is a $C_1$~$C_6$ alkyl group or a $C_2$~$C_6$ alkenyl group, $R_{11}$ is a $C_1$~$C_6$ alkyl group, $R_{12}$ is a $C_1$~$C_6$ alkylsulfonyl group or a 5- to 12-membered, preferably 5- to 6-membered heteroaryl group optionally substituted with $C_1$~$C_6$ alkyl, $R_{13}$ is a $C_1$~$C_6$ alkyl group, $R_{14}$ is hydrogen or a halogen group.

In another embodiment of the present invention, $R_2$ and $R_3$ are cyclized each other to form a piperazinyl group or a piperidinyl group.

In still another embodiment of the present invention, $R_2$ and $R_3$ are cyclized each other to form a piperazinyl group or a piperidinyl group, and the piperazinyl group or the piperidinyl group is optionally substituted with one or more substituents selected from the group consisting of $C_1$~$C_6$ alkyl optionally substituted with one or more halogens;

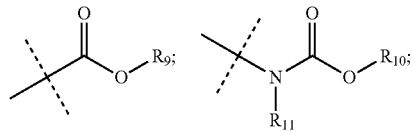

—$NR_{12}R_{13}$; and 5- to 12-membered, preferably 5- to 6-membered heteroaryl selected from the group consisting of pyrimidyl, pyridyl, or 1,2,4-oxadiazolyl (wherein, the heteroaryl moiety may be optionally substituted with $C_1$~$C_6$ alkyl optionally substituted with one or more halogens).

The compound of Formula 1 or its pharmaceutically acceptable salt may have substituents containing asymmetric carbon and therefore be in the form of racemic mixture (RS) or in forms of optical isomers, such as (R) or (S) isomer. The compound of Formula 1 or its pharmaceutically acceptable salt comprises both racemic mixture (RS) and optical isomers such as (R) or (S) isomer.

The compound of Formula 1 of the present invention may be in a pharmaceutically acceptable salt form. The salt may be an acid addition salt form, which includes e.g., salts derived from an inorganic acid such as hydrochloric acid, hydrobromic acid, sulfuric acid, sulfamic acid, phosphoric acid, or nitric acid; and salts derived from an organic acid such as acetic acid, propionic acid, succinic acid, glycolic acid, stearic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethanesulfonic acid, oxalic acid or trifluoroacetic acid. And also, the salt includes e.g., salts derived from sodium hydroxide, lithium hydroxide, potassium hydroxide, calcium hydroxide, potassium carbonate, calcium carbonate, potassium t-butoxide, sodium ethoxide, triethylamine, ammonia, guanidine, ethylenediamine, ethanolamine, diethanolamine, triethanolamine, piperazine, morpholine, or dicyclohexylamine.

The pharmaceutically acceptable salt form of the compound of Formula 1 may be prepared from the compound of Formula 1 having basic amine and/or carboxylic acid group, according to conventional methods. In general, the salt may be prepared by reacting a compound of Formula 1 in the form of free acid/base with a salt-forming inorganic, inorganic salt, organic acid or organic salt in stoichiometric amount or excessive amount, in a suitable solvent or a mixture of two or more solvents.

The compound of Formula 1 or its pharmaceutically acceptable salt of the present invention may be prepared according to the following exemplary processes. In an embodiment, the present invention provides a process for preparing a compound of Formula 1a or its pharmaceutically acceptable salt, which comprises reacting a compound of Formula 2 with a compound of Formula 3:

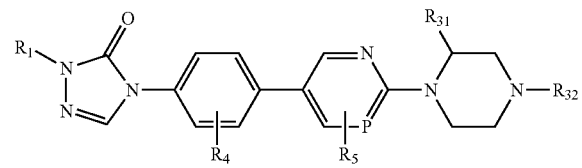

<Formula 1a>

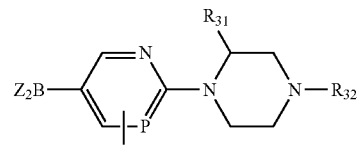

<Formula 2>

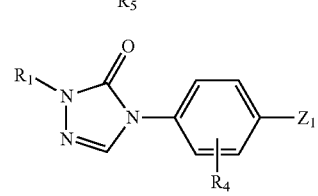

<Formula 3> wherein, $Z_1$ is halogen or O-trifluoromethanesulfonyl, $Z_2$ is hydroxy, $C_1$~$C_6$ alkyl, or $C_1$~$C_6$ alkoxy, $R_{31}$ is hydrogen; $C_1$~$C_6$ alkyl optionally substituted with one or more halogens;

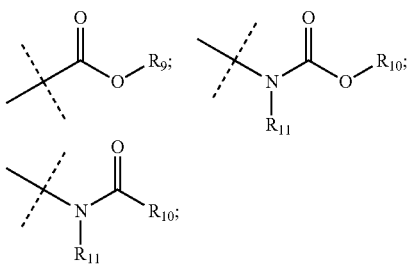

or —$NR_{12}R_{13}$, $R_{32}$ is

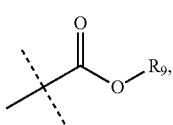

5- to 12-membered heteroaryl or 3- to 12-membered heterocyclic (wherein, the heteroaryl or heterocyclic moiety may be optionally substituted with one or more $C_1$~$C_6$ alkyls optionally substituted with one or more halogens), and $R_1$, $R_4$, $R_5$, $R_9$, $R_{10}$, $R_{11}$, $R_{12}$, $R_{13}$, and P are the same as defined in the above.

The reaction between the compound of Formula 2 and the compound of Formula 3 may be performed according to Suzuki reaction. The reaction may be carried out using a palladium catalyst. The palladium catalyst includes, for example, palladium diacetate ($Pd(OAc)_2$), tris(dibenzylideneacetone)dipalladium ($Pd_2(dba)_3$), tetrakis(triphenylphosphine)palladium ($Pd(PPh_3)_4$) or palladium di[1,1'-bis(diphenylphosphino)ferrocene]dichloride ($PdCl_2(dppf)_2$). In carrying out the reaction, a ligand and a base may be also added thereto, in addition to the palladium catalyst. The ligand includes, for example, (S)-2,2-bis(diphenylphosphino)-1,1-binaphthyl (BINAP), 1,1'-bis(diphenylphosphino)ferrocene (dppf) or tri(O-tolyl)phosphine ($P(O-Tol)_3$). The base includes an inorganic base, such as cesium carbonate ($Cs_2CO_3$), sodium carbonate ($Na_2CO_3$), potassium carbonate ($K_2CO_3$), potassium fluoride (KF), cesium fluoride (CsF), sodium hydroxide (NaOH), potassium phosphate ($K_3PO_4$), sodium tert-butoxide (tert-BuONa) or potassium tert-butoxide (tert-BuOK). The reaction may be carried out in a non-polar organic solvent such as benzene or toluene, or a polar solvent such as dioxane, tetrahydrofuran, acetonitrile, 1,2-dimethoxyethane or N,N-dimethylformamide. The reaction may be also carried out at a temperature ranging from 50° C. to 150° C., preferably from 80° C. to 110° C. Other reaction conditions, including e.g., reaction time, may be determined from the reaction conditions for conventional Suzuki reaction (Barbara Czako and Laszlo Kurti, STRATEGIC APPLICATIONS of NAMED REACTIONS in ORGANIC SYNTHESIS, 2005).

The compound of Formula 2 may be prepared according to the following Reaction Scheme 1 or 2.

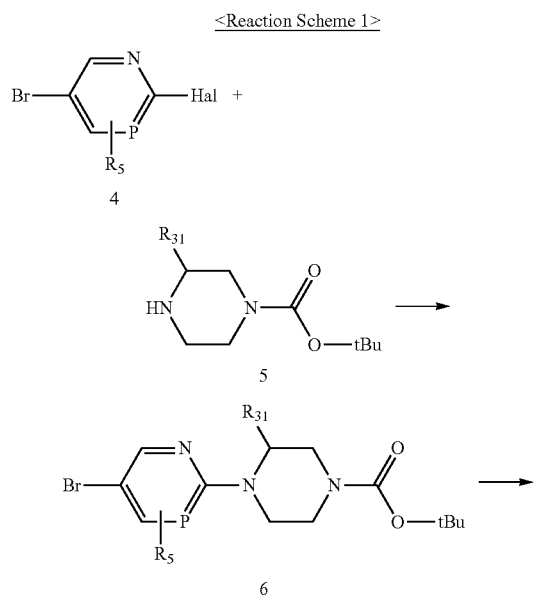

<Reaction Scheme 1>

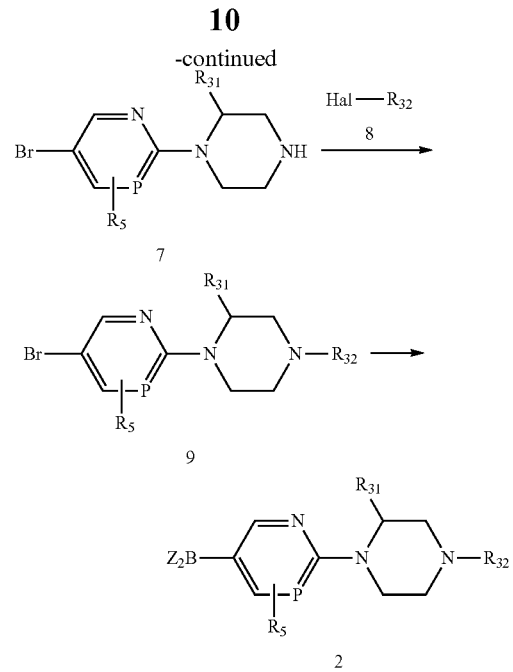

In the Reaction Scheme 1, Hal is halogen; tBu is tert-butyl; and $R_5$, $R_{31}$, $R_{32}$, $Z_2$, and P are the same as defined in the above.

The compound of Formula 4 and the compound of Formula 5 are commercially available. The coupling reaction of the compound of Formula 4 and the compound of Formula 5 may be carried out in the presence of a base and a solvent. The base includes cesium carbonate, potassium carbonate, sodium carbonate, etc. The solvent includes an organic solvent such as N,N-dimethylformamide, dioxane, tetrahydrofuran, etc. And also, the reaction may be carried out at a temperature ranging from room temperature to 100° C.

The compound of Formula 6 may be converted to the compound of Formula 7 via deprotecting reaction. The deprotection may be carried out according to conventional methods (Theodora W. Greene and Peter G. M. Wuts, Protective groups in organic synthesis, 3rd Ed., 1999). For example, the deprotection may be carried out using trifluoroacetic acid or hydrochloric acid solution, in an organic solvent such as dichloromethane, dioxane or ethyl acetate at room temperature.

The compound of Formula 7 may be coupled with the commercially available $R_{32}$ halide (i.e., the compound of Formula 8) to give the compound of Formula 9. The coupling reaction may be carried out in the presence of a conventional inorganic base and a conventional organic solvent.

The compound of Formula 9 may be converted to the compound of Formula 2 via boron-esterification. The reaction for boron-esterification may be carried out using a boron-esterification reagent and a palladium catalyst. The boron-esterification reagent includes, for example, tetrahydroxydiboron, pinacol diborane, etc. The palladium catalyst includes, for example, tris(dibenzylideneacetone)dipalladium ($Pd_2(dba)_3$), palladium di[1,1'-bis(diphenylphosphino)ferrocene]dichloride ($PdCl_2(dppf)_2$) or palladium diacetate ($Pd(OAc)_2$). In carrying out the reaction, a ligand and a base may be also added thereto, in addition to the palladium catalyst. The ligand includes, for example, 2-dichlorohexylphophino-2',4',6'-triisopropylbiphenyl (XPhos) or 1,1'-bis (diphenylphosphino)ferrocene (dppf). The base includes an inorganic base, such as potassium acetate or potassium tert-butoxide. The reaction may be carried out in a polar solvent such as dioxane or N,N-dimethylformamide, at a temperature ranging from 80° C. to 100° C.

The compound of Formula 2 may be also prepared according to the following Reaction Scheme 2.

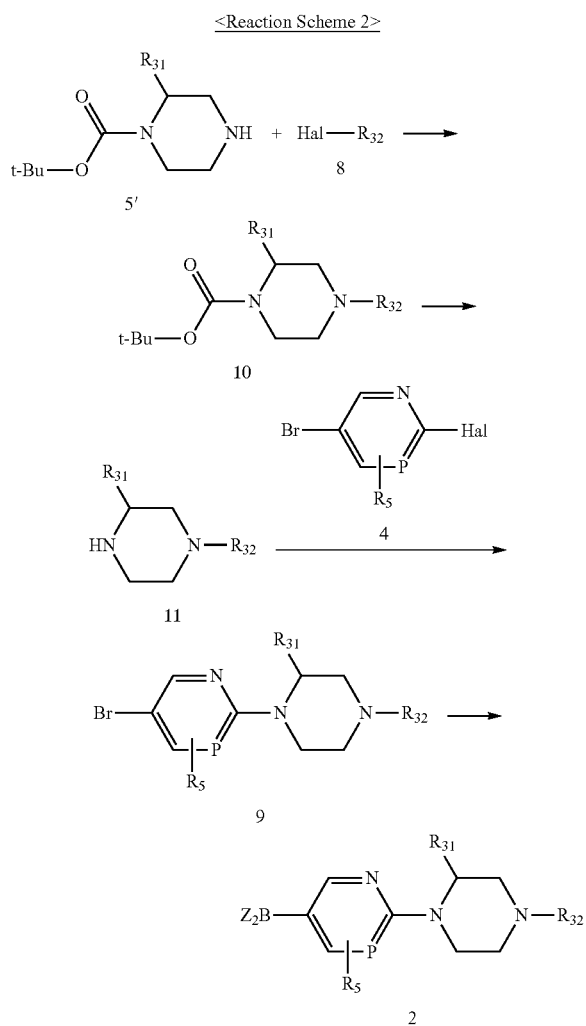

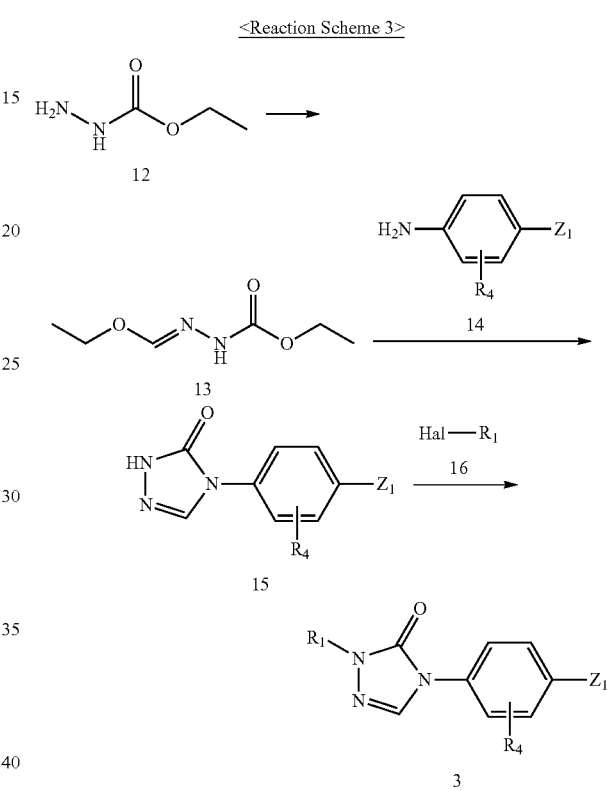

In the Reaction Scheme 2, Hal is halogen; tBu is tert-butyl; and $R_5$, $R_{31}$, $R_{32}$, $Z_2$, and P are the same as defined in the above.

The compound of Formula 5' and the compound of Formula 8 are commercially available. The coupling reaction of the compound of Formula 5' and the compound of Formula 8 may be carried out according to the same methods as in the coupling reaction of the compound of Formula 7 and the compound of Formula 8 in the Reaction Scheme 1.

The deprotection of the compound of Formula 10 may be carried out according to the same methods as in the deprotection of the compound of Formula 6 in the Reaction Scheme 1.

The compound of Formula 11 may be coupled with the commercially available compound of Formula 4 to give the compound of Formula 9. The coupling reaction may be carried out according to the same methods as in the coupling reaction of the compound of Formula 4 and the compound of Formula 5 in the Reaction Scheme 1.

The compound of Formula 9 may be converted to the compound of Formula 2 via boron-esterification. The reaction for boron-esterification may be carried out according to the same methods as in the boron-esterification in the Reaction Scheme 1.

The compound of Formula 3 may be prepared according to the following Reaction Scheme 3.

In the Reaction Scheme 3, Hal is halogen; and $R_1$, $R_4$, and $Z_1$ are the same as defined in the above.

The compound of Formula 12 may be formylated to give the compound of Formula 13. The formylation may be carried out according to an ortho-ester reaction, using for example triethyl orthoformate or trimethyl orthoformate. The formylation may be carried out in a solvent such as methanol or N,N-dimethylformamide at a temperature ranging from 80° C. to 150° C.

The compound of Formula 13 may be cyclized with the compound of Formula 14 to give the compound of Formula 15. The cyclization may be carried out using sodium methoxide or potassium hydroxide, in a solvent such as methanol or N,N-dimethylformamide at a temperature ranging from 50° C. to 150° C.

The compound of Formula 15 may be reacted with the commercially available compound of Formula 16 to give the compound of Formula 3. The reaction may be carried out in the presence of a conventional inorganic base, according to N-alkylation reaction.

In another embodiment, the present invention provides a process for preparing a compound of Formula 1b or its pharmaceutically acceptable salt, which comprises reacting a compound of Formula 17 with a compound of Formula 3:

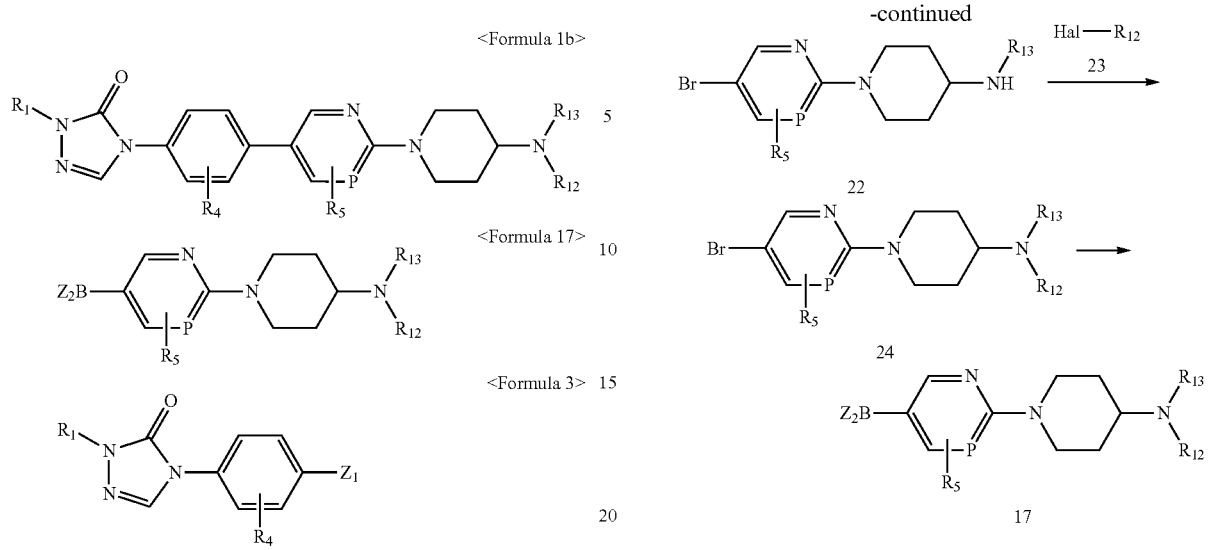

wherein, $Z_1$ is halogen or O-trifluoromethanesulfonyl, $Z_2$ is hydroxy, $C_1$~$C_6$ alkyl, or $C_1$~$C_6$ alkoxy, $R_1$, $R_4$, $R_5$, $R_{12}$, $R_{13}$, and P are the same as defined in the above.

The reaction between the compound of Formula 17 and the compound of Formula 3 may be performed according to Suzuki reaction. The reaction may be carried out using a palladium catalyst. Other reaction conditions, including e.g., reaction time, may be determined from the reaction conditions for conventional Suzuki reaction (Barbara Czako and Laszlo Kurd, STRATEGIC APPLICATIONS of NAMED REACTIONS in ORGANIC SYNTHESIS, 2005).

The compound of Formula 17 may be prepared according to the following Reaction Scheme 4.

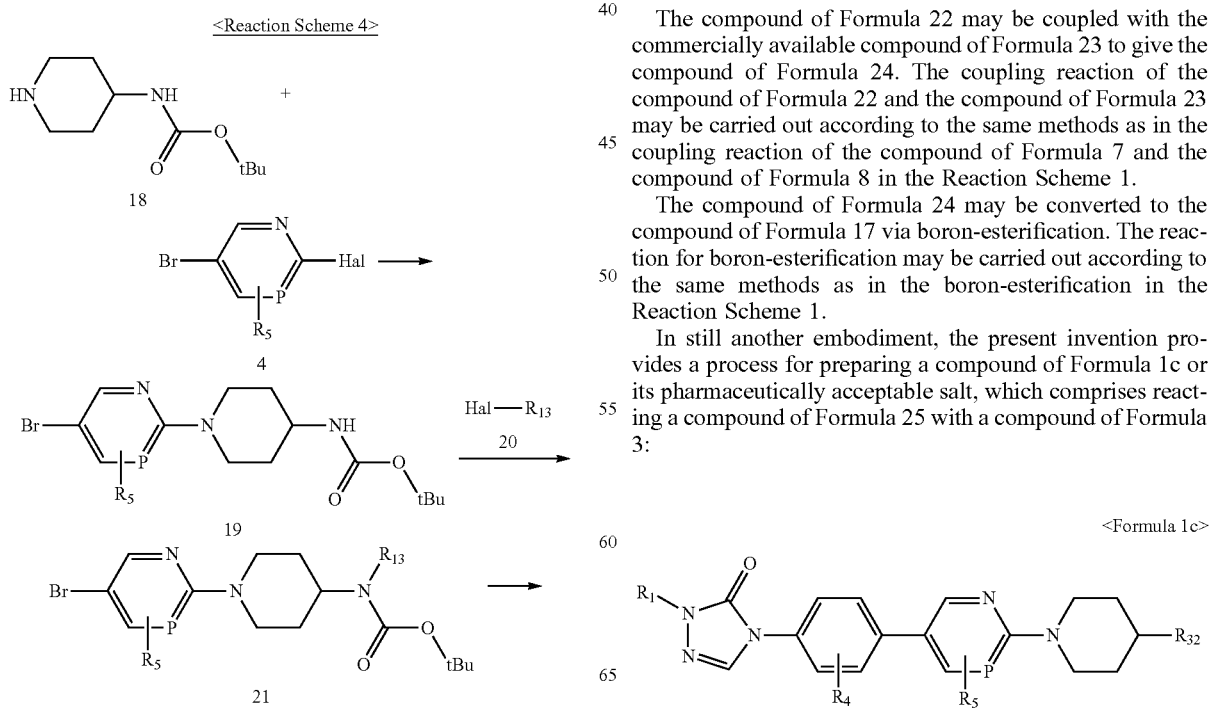

In the Reaction Scheme 4, Hal is halogen; tBu is tert-butyl; and $R_5$, $R_{12}$, $R_{13}$, $Z_2$, and P are the same as defined in the above.

The compound of Formula 18 and the compound of Formula 4 are commercially available. The coupling reaction of the compound of Formula 18 and the compound of Formula 4 may be carried out according to the same methods as in the coupling reaction of the compound of Formula 4 and the compound of Formula 5 in the Reaction Scheme 1.

The compound of Formula 19 may be reacted with the commercially available compound of Formula 20 to give the compound of Formula 21. The reaction may be carried out in the presence of a conventional inorganic base, according to N-alkylation reaction.

The deprotection of the compound of Formula 21 may be carried out according to the same methods as in the deprotection of the compound of Formula 6 in the Reaction Scheme 1.

The compound of Formula 22 may be coupled with the commercially available compound of Formula 23 to give the compound of Formula 24. The coupling reaction of the compound of Formula 22 and the compound of Formula 23 may be carried out according to the same methods as in the coupling reaction of the compound of Formula 7 and the compound of Formula 8 in the Reaction Scheme 1.

The compound of Formula 24 may be converted to the compound of Formula 17 via boron-esterification. The reaction for boron-esterification may be carried out according to the same methods as in the boron-esterification in the Reaction Scheme 1.

In still another embodiment, the present invention provides a process for preparing a compound of Formula 1c or its pharmaceutically acceptable salt, which comprises reacting a compound of Formula 25 with a compound of Formula 3:

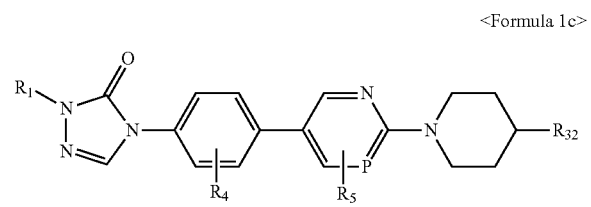

-continued

<Formula 25>

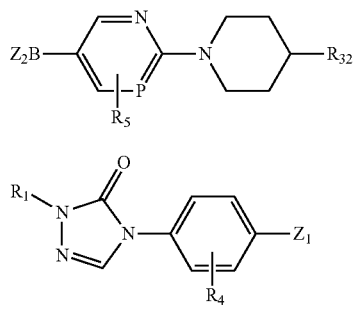

<Formula 3>

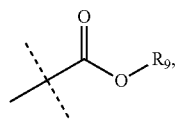

wherein, $Z_1$ is halogen or O-trifluoromethanesulfonyl,
$Z_2$ is hydroxy, $C_1$~$C_6$ alkyl, or $C_1$~$C_6$ alkoxy,
$R_{32}$ is

5- to 12-membered heteroaryl or 3- to 12-membered heterocyclic (wherein, the heteroaryl or heterocyclic moiety may be optionally substituted with one or more $C_1$~$C_6$ alkyls optionally substituted with one or more halogens), $R_1$, $R_4$, $R_5$, and P are the same as defined in the above.

The reaction between the compound of Formula 25 and the compound of Formula 3 may be performed according to Suzuki reaction. The reaction may be carried out using a palladium catalyst. Other reaction conditions, including e.g., reaction time, may be determined from the reaction conditions for conventional Suzuki reaction (Barbara Czako and Laszlo Kurd, STRATEGIC APPLICATIONS of NAMED REACTIONS in ORGANIC SYNTHESIS, 2005).

The compound of Formula 25, wherein $R_{32}$ is for example 3-isopropyl-1,2,4-oxadiazole, may be prepared according to the following Reaction Scheme 5 or 6.

<Reaction Scheme 5>

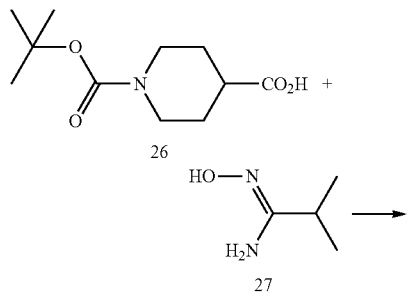

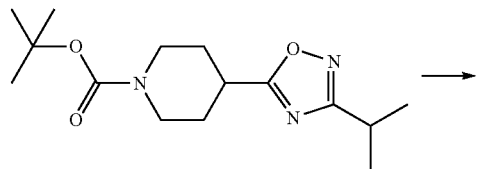

-continued

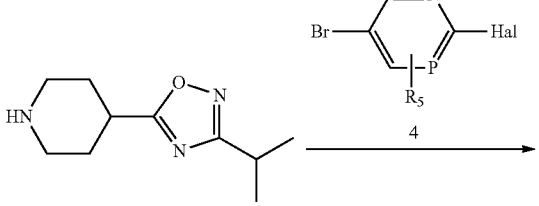

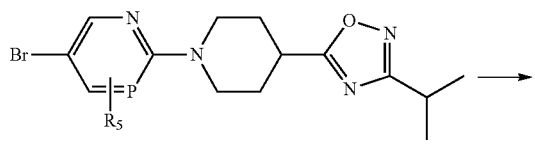

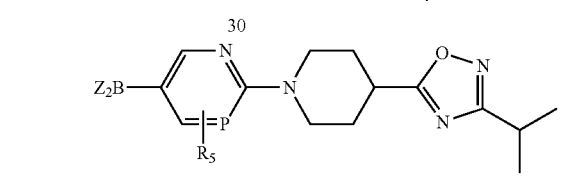

In the Reaction Scheme 5, Hal is halogen; and $R_5$, $R_{32}$, $Z_2$, and P are the same as defined in the above.

The compound of Formula 26 and the compound of Formula 27 are commercially available. The compound of Formula 26 may be cyclized with the compound of Formula 27 to give the compound of Formula 28. The cyclization may be carried out using sodium methoxide or sodium hydride, in a solvent such as tetrahydrofuran or N,N-dimethylformamide at a temperature ranging from 50° C. to 150° C.

The deprotection of the compound of Formula 28 may be carried out according to the same methods as in the deprotection of the compound of Formula 6 in the Reaction Scheme 1.

The compound of Formula 29 may be coupled with the commercially available compound of Formula 4 to give the compound of Formula 30. The coupling reaction may be carried out according to the same methods as in the coupling reaction of the compound of Formula 4 and the compound of Formula 5 in the Reaction Scheme 1.

The compound of Formula 30 may be converted to the compound of Formula 25 via boron-esterification. The reaction for boron-esterification may be carried out according to the same methods as in the boron-esterification in the Reaction Scheme 1.

The compound of Formula 25, wherein $R_{32}$ is for example 3-isopropyl-1,2,4-oxadiazole, may be also prepared according to the following Reaction Scheme 6.

<Reaction Scheme 6>

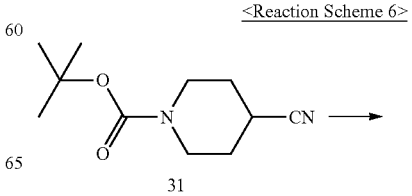

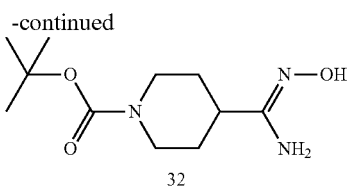

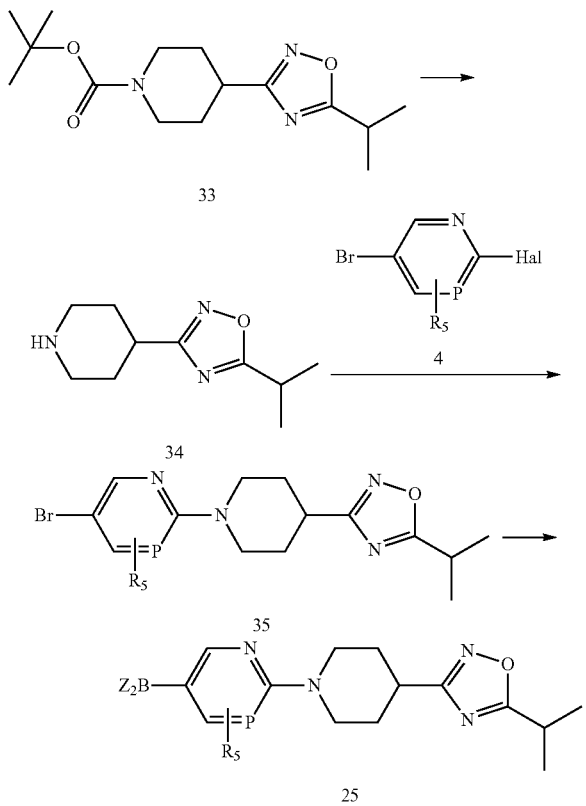

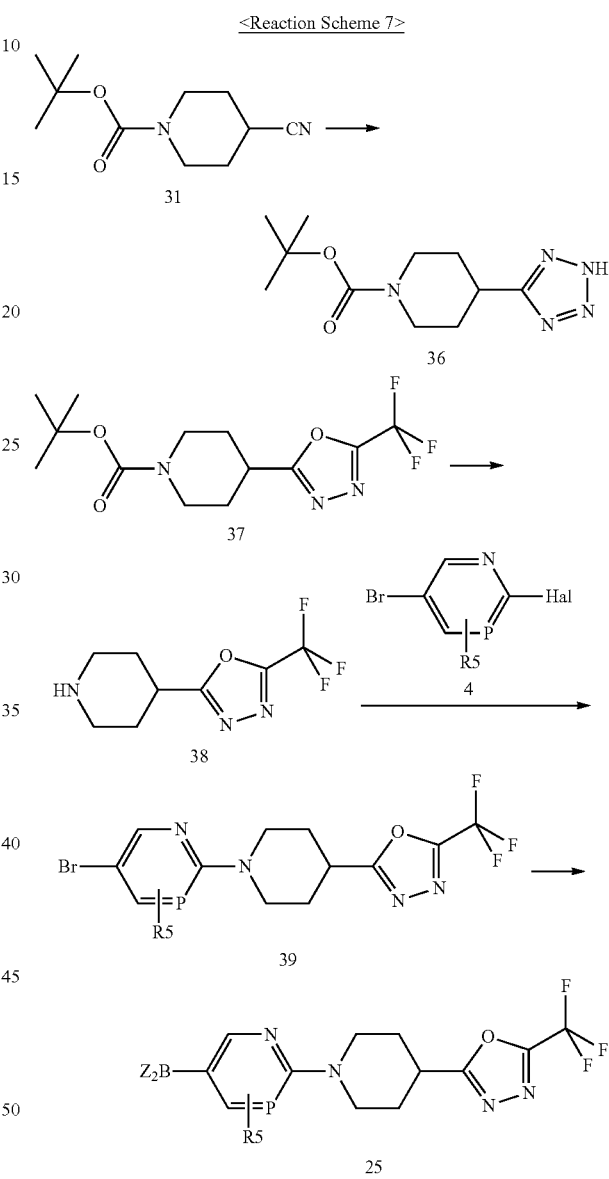

In the Reaction Scheme 6, Hal is halogen; and $R_5$, $R_{32}$, $Z_2$, and P are the same as defined in the above.

The compound of Formula 31 is commercially available. The compound of Formula 31 may be converted to the compound of Formula 32, through hydroxylamine incorporation. The reaction for hydroxylamine incorporation may be carried out according to conventional methods (Pace, Paola; Francesco, M. Emilia Di; Gardelli, Cristina; Harper, Steven; Muraglia, Ester; Nizi, Emanuela, Journal of Medicinal Chemistry, 50, 2225-2239, 2007).

The compound of Formula 32 may be cyclized to give the compound of Formula 33. The cyclization may be carried out using N-ethyl-N,N-diisopropylamine (DIPEA) or triethylamine, in a solvent such as toluene or N,N-dimethylformamide at a temperature ranging from 50° C. to 150° C.

The deprotection of the compound of Formula 33 may be carried out according to the same methods as in the deprotection of the compound of Formula 6 in the Reaction Scheme 1.

The compound of Formula 34 may be coupled with the commercially available compound of Formula 4 to give the compound of Formula 35. The coupling reaction may be carried out according to the same methods as in the coupling reaction of the compound of Formula 4 and the compound of Formula 5 in the Reaction Scheme 1.

The compound of Formula 35 may be converted to the compound of Formula 25 via boron-esterification. The reaction for boron-esterification may be carried out according to the same methods as in the boron-esterification in the Reaction Scheme 1.

The compound of Formula 25, wherein $R_{32}$ is for example 5-trifluoromethyl-1,3,4-oxadiazole, may be prepared according to the following Reaction Scheme 7.

In the Reaction Scheme 7, Hal is halogen; and $R_5$, $R_{32}$, $Z_2$, and P are the same as defined in the above.

The compound of Formula 31 is commercially available. The compound of Formula 31 may be converted to the compound of Formula 36, through azide addition. The reaction for azide addition may be carried out using sodium azide, in a solvent such as toluene or N,N-dimethylformamide at a temperature ranging from 100° C. to 150° C.

The compound of Formula 36 may be reacted with anhydrous trifluoroacetic acid to give the compound of Formula 37. The reaction between the compound of Formula 36 and anhydrous trifluoroacetic acid may be carried out according to conventional methods (Pradip K. Sasmal, Rashmi Talwar; J. Swetha, D. Balasubrahmanyam; B. Venkatesham, Khaji Abdul Rawoof; B. Neelima Devi, Vikram P. Jadhav; Sanjoy K. Khan, Priya Mohan; D. Srinivasa Reddy, Vijay Kumar Nyavanandi, Bioorganic and Medicinal Chemistry Letters, 21, 4913-4918, 2011).

The deprotection of the compound of Formula 37 may be carried out according to the same methods as in the deprotection of the compound of Formula 6 in the Reaction Scheme 1.

The compound of Formula 38 may be coupled with the commercially available compound of Formula 4 to give the compound of Formula 39. The coupling reaction may be carried out according to the same methods as in the coupling reaction of the compound of Formula 4 and the compound of Formula 5 in the Reaction Scheme 1.

The compound of Formula 39 may be converted to the compound of Formula 25 via boron-esterification. The reaction for boron-esterification may be carried out according to the same methods as in the boron-esterification in the Reaction Scheme 1.

The compound of Formula 2, wherein $R_{32}$ is for example 5-trifluoromethyl-1,3,4-oxadiazole, may be also prepared according to the following Reaction Scheme 8.

<Reaction Scheme 8>

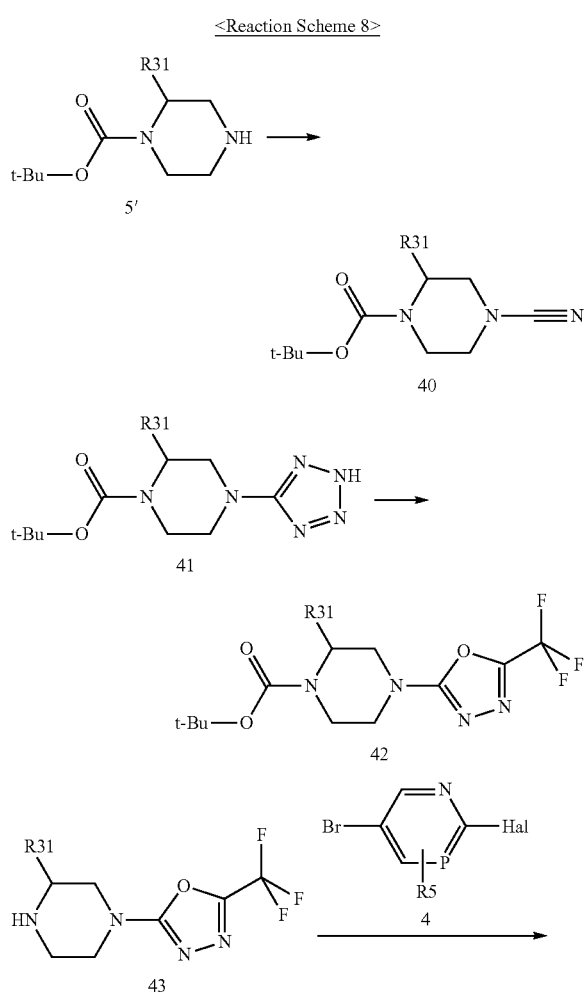

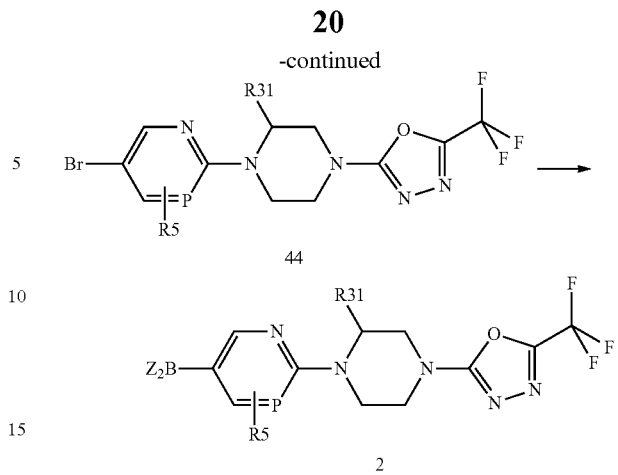

In the Reaction Scheme 8, Hal is halogen; t-Bu is tert-butyl; and $R_5$, $R_{31}$, $R_{32}$, $Z_2$, and P are the same as defined in the above.

The compound of Formula 5' may be coupled with cyanogen halide to give the compound of Formula 40. The coupling reaction may be carried out in the presence of a conventional inorganic base and a conventional organic solvent.

The compound of Formula 40 may be converted to the compound of Formula 41, through azide addition. The reaction for azide addition may be carried out according to the same methods as in the reaction for azide addition of the compound of Formula 31 in the Reaction Scheme 7.

The compound of Formula 41 may be reacted with anhydrous trifluoroacetic acid to give the compound of Formula 42. The reaction between the compound of Formula 41 and anhydrous trifluoroacetic acid may be carried out according to the same methods as in the reaction between the compound of Formula 36 and anhydrous trifluoroacetic acid in the Reaction Scheme 7.

The deprotection of the compound of Formula 42 may be carried out according to the same methods as in the deprotection of the compound of Formula 6 in the Reaction Scheme 1.

The compound of Formula 43 may be coupled with the commercially available compound of Formula 4 to give the compound of Formula 44. The coupling reaction may be carried out according to the same methods as in the coupling reaction of the compound of Formula 4 and the compound of Formula 5 in the Reaction Scheme 1.

The compound of Formula 44 may be converted to the compound of Formula 2 via boron-esterification. The reaction for boron-esterification may be carried out according to the same methods as in the boron-esterification in the Reaction Scheme 1.

In the processes described in the above, the following compound of Formula 3a is a new compound useful for preparing the compounds according to the present invention. Therefore, the present invention also provides a compound of Formula 3a:

<Formula 3a>

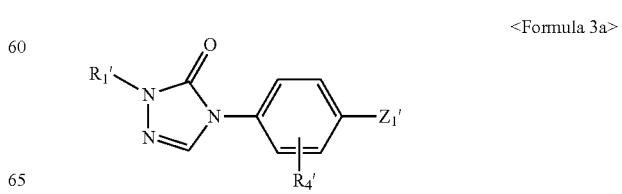

wherein, $R_1'$ is a $C_1$~$C_6$ alkyl group optionally substituted with one or more substituents selected from the group consisting of hydroxy, $C_1$~$C_3$ alkoxy, 5- to 6-membered heterocyclic, $C_1$~$C_3$ dialkylamino, and hydroxycarbonyl; a $C_1$~$C_3$ alkylcarbonyl group; or a 5- to 6-membered heterocyclic group, $R_4'$ and $Z_1'$ are, independently each other, a halogen group.

In the compound of Formula 3a, $R_1'$ may be a $C_1$~$C_6$ alkyl group optionally substituted with one or more substituents selected from the group consisting of hydroxy, methoxy, pyrrolidinyl, morpholinyl, diethylamino, and hydroxycarbonyl; a methylcarbonyl group; or a tetrahydrofuranyl group. In the compound of Formula 3a, $R_4'$ may be a fluoro group. And also, in the compound of Formula 3a, $Z_1'$ may be a bromo group.

Examples of preferable compounds of Formula 3a include:

4-(4-bromo-2-fluorophenyl)-1-methyl-1H-1,2,4-triazol-5 (4H)-one;
4-(4-bromo-2-fluorophenyl)-1-propyl-1H-1,2,4-triazol-5 (4H)-one;
4-(4-bromo-2-fluorophenyl)-1-isopropyl-1H-1,2,4-triazol-5 (4H)-one;
4-(4-bromo-2-fluorophenyl)-1-(2-methoxyethyl)-1H-1,2,4-triazol-5(4H)-one;
4-(4-bromo-2-fluorophenyl)-1-[2-(diethylamino)ethyl]-1H-1,2,4-triazol-5(4H)-one;
4-(4-bromo-2-fluorophenyl)-1-(2-hydroxy-2-methylpropyl)-1H-1,2,4-triazol-5(4H)-one;
4-(4-bromo-2-fluorophenyl)-1-isobutyl-1H-1,2,4-triazol-5 (4H)-one;
methyl 2-[4-(4-bromo-2-fluorophenyl)-5-oxo-4,5-dihydro-1H-1,2,4-triazol-1-yl]acetate;
4-(4-bromo-2-fluorophenyl)-1-(2-morpholinoethyl)-1H-1,2,4-triazol-5(4H)-one;
(S)-4-(4-bromo-2-fluorophenyl)-1-(tetrahydrofuran-3-yl)-1H-1,2,4-triazol-5(4H)-one
4-(4-bromo-2-fluorophenyl)-1-(methoxymethyl)-1H-1,2,4-triazol-5(4H)-one;
ethyl 4-(4-bromo-2-fluorophenyl)-5-oxo-4,5-dihydro-1H-1,2,4-triazol-1-carboxylate;
(R)-4-(4-bromo-2-fluorophenyl)-1-(tetrahydrofuran-3-yl)-1H-1,2,4-triazol-5(4H)-one; and
4-(4-bromo-2-fluorophenyl)-1-(pyrrolidin-1-ylmethyl)-1H-1,2,4-triazol-5(4H)-one.

The present invention provides a pharmaceutical composition for preventing or treating diabetes mellitus comprising a therapeutically effective amount of the compound of Formula 1 or its pharmaceutically acceptable salt as an active ingredient.

The pharmaceutical composition of the present invention may comprise a pharmaceutically acceptable carrier, such as diluents, disintegrants, sweeteners, lubricants, or flavoring agents. The pharmaceutical composition may be formulated to an oral dosage form such as tablets, capsules, powders, granules, suspensions, emulsions, or syrups; or a parenteral dosage form such as injection, according to conventional methods. The dosage form may be various forms, e.g., dosage forms for single administration or for multiple administrations.

The composition of the present invention may be administered orally or parenterally, including intravenous, intramuscular, intraperitoneal, subcutaneous, rectal and topical routes of administration. Preferably, the composition of the present invention may be administered orally. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular bloodstream by local bolus injection.

The compound of Formula 1 or its pharmaceutically acceptable salt may be administered in a therapeutically effective amount ranging from about 10 mg/kg to about 500 mg/kg per day to a subject patient. Of course, the dosage may be changed according to the patient's age, weight, susceptibility, symptom, or activity of the compound.

The present invention also provides a method for preventing or treating diabetes mellitus in a mammal, including a human, in need thereof, which comprises administering to such mammal a therapeutically effective amount of the compound of Formula 1 or its pharmaceutically acceptable salt.

The present invention also provides a use of the compound or its pharmaceutically acceptable salt for the manufacture of a medicament for preventing or treating diabetes mellitus.

The following examples and experimental examples are provided for illustration purposes only, and are not intended to limit the scope of the invention.

The analyses of the compounds prepared in the following Preparations and Examples were carried out as follows: Nuclear magnetic resonance (NMR) spectrum analysis was carried out using Bruker 400 MHz spectrometer and chemical shifts thereof were analyzed in ppm. Column chromatography was carried out on silica gel (Merck, 70-230 mesh) (W. C. Still, *J. Org. Chem.*, 1978 (43), 2923-2925). The abbreviations used in the following Preparations and Examples are as follows: 'methyl' is abbreviated to 'Me'; 'ethyl' is abbreviated to 'Et'; 'phenyl' is abbreviated to 'Ph'; 'tertbutyloxycarbonyl' is abbreviated to 'BOC'. The starting materials in each Example are known compounds, which were synthesized according literatures or obtained from Sigma-Aldrich.

Preparation 1. 4-(4-bromo-2-fluorophenyl)-1-methyl-1H-1,2,4-triazol-5(4H)-one

Step 1: (E)-ethyl 2-(ethoxymethylene)hydrazinecarboxylate

A solution of ethyl carbazate (200.0 g) in triethyl orthoformate (1.0 L) was stirred at 110° C. for 12 hours. The solution was cooled to room temperature and then concentrated under reduced pressure to give 292 g of the titled compound as a white solid (Yield: 95.0%).

$^1$H-NMR (CDCl$_3$) δ 8.05 (s, 1H), 6.53 (s, 1H), 4.18 (q, 2H), 4.13 (q, 2H), 1.36 (t, 3H), 1.31 (t, 3H)

Step 2: 4-(4-bromo-2-fluorophenyl)-1H-1,2,4-triazol-5(4H)-one

To a solution of (E)-ethyl 2-(ethoxymethylene)hydrazinecarboxylate (292.0 g) prepared in Step 1 in methanol (1.0 L), was added 4-bromo-2-fluoroaniline (200.0 g). The reaction mixture was refluxed at 110° C. for 3 days and then cooled to room temperature. A solution of NaOMe in methanol (25%) was added to the reaction mixture, which was then refluxed at 110° C. for 4 hours. The reaction mixture was cooled to room temperature and then concentrated under reduced pressure. To the resulting residue, was added ethyl acetate (500.0 mL). The mixture was washed with an aqueous solution of ammonium chloride, dried over anhydrous sodium sulfate, and then concentrated under reduced pressure to give 423.2 g of the titled compound as a white solid (Yield: 90.1%).
$^1$H-NMR (MeOD) δ 7.97 (s, 1H), 7.62 (t, 1H), 7.55-7.53 (m, 2H)

Step 3: 4-(4-bromo-2-fluorophenyl)-1-methyl-1H-1,2,4-triazol-5(4H)-one

To a solution of 4-(4-bromo-2-fluorophenyl)-1H-1,2,4-triazol-5(4H)-one (1.0 g) prepared in Step 2 in N,N-dimethylformamide (50.0 mL), was added potassium hydroxide (435.0 mg). The reaction mixture was stirred at room temperature for 10 minutes and then iodomethane (0.48 mL) was added thereto. The reaction mixture was stirred at 40° C. for 12 hours, cooled to room temperature, and then concentrated under reduced pressure. Ethyl acetate (30.0 mL) and brine (30.0 mL) were added to the residue and then the organic layer was separated. Ethyl acetate (30.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=2/1) to give 728.0 mg of the titled compound as a white solid (Yield: 69.1%).
$^1$H-NMR (CDCl$_3$) δ 7.64 (s, 1H), 7.62 (t, 1H), 7.44-7.42 (m, 2H), 3.54 (s, 3H)

Preparation 2. 4-(4-bromo-2-fluorophenyl)-1-propyl-1H-1,2,4-triazol-5(4H)-one

To a solution of 4-(4-bromo-2-fluorophenyl)-1H-1,2,4-triazol-5(4H)-one (3.0 g) prepared in Step 2 of Preparation 1 in N,N-dimethylformamide (120.0 mL), was added potassium hydroxide (1.3 g). The reaction mixture was stirred at room temperature for 10 minutes and then 1-bromopropane (1.08 mL) was added thereto. The reaction mixture was stirred at 60° C. for 12 hours, cooled to room temperature, and then concentrated under reduced pressure. Ethyl acetate (50.0 mL) and brine (50.0 mL) were added to the residue and then the organic layer was separated. Ethyl acetate (50.0 mL) was added to the water layer and then the organic layer was separated. The combined organic layer was dried over anhydrous sodium sulfate and then concentrated under reduced pressure to give 3.41 g of the titled compound as a white solid (Yield: 98.0%).
$^1$H-NMR (CDCl$_3$) δ 7.66 (s, 1H), 7.64 (t, 1H), 7.45-7.42 (m, 2H), 3.82 (t, 2H), 1.86-1.79 (m, 2H), 0.98 (t, 3H)

Preparation 3. 4-(4-bromo-2-fluorophenyl)-1-isopropyl-1H-1,2,4-triazol-5(4H)-one To a solution of 4-(4-bromo-2-fluorophenyl)-1H-1,2,4-triazol-5(4H)-one (100.0 mg) prepared in Step 2 of Preparation 1 in N,N-dimethylformamide (5.0 mL), was added potassium hydroxide (43.5 mg). The reaction mixture was stirred at room temperature for 10 minutes and then 2-bromopropane (72.8 μL) was added thereto. The reaction mixture was stirred at 60° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=2/1) to give 76.7 mg of the titled compound as a white solid (Yield: 66.0%).
$^1$H-NMR (CDCl$_3$) δ 7.66 (s, 1H), 7.64 (t, 1H), 7.45-7.42 (m, 2H), 2.21-2.17 (m, 1H), 0.97 (d, 6H)

Preparation 4. 4-(4-bromo-2-fluorophenyl)-1-(2-methoxyethyl)-1H-1,2,4-triazol-5(4H)-one To a solution of 4-(4-bromo-2-fluorophenyl)-1H-1,2,4-triazol-5(4H)-one (2.0 g) prepared in Step 2 of Preparation 1 in N,N-dimethylformamide (20.0 mL), was added potassium hydroxide (870.0 mg). The reaction mixture was stirred at room temperature for 10 minutes and then 2-bromoethyl methyl ether (1.46 mL) was added thereto. The reaction mixture was stirred at 60° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=1/2) to give 1.74 g of the titled compound as a white solid (Yield: 71.0%).
$^1$H-NMR (CDCl$_3$) δ 7.71 (s, 1H), 7.62 (t, 1H), 7.46-7.44 (m, 2H), 4.07 (t, 2H), 3.81 (t, 2H), 3.49 (s, 3H)

Preparation 5. 4-(4-bromo-2-fluorophenyl)-1-[2-(diethylamino)ethyl]-1H-1,2,4-triazol-5(4H)-one To a solution of 4-(4-bromo-2-fluorophenyl)-1H-1,2,4-triazol-5(4H)-one (200.0 mg) prepared in Step 2 of Preparation 1 in N,N-dimethylformamide (5.0 mL), was added NaH (62.0 mg). The reaction mixture was stirred at room temperature for 30 minutes and then 2-chloro-N,N-diethylethylamine hydrochloride (160.0 mg) was added thereto. The reaction mixture was stirred at 70° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a colorless oily residue. The residue was purified with silica gel column chromatography (dichloromethane/methanol=20/1) to give 107.0 mg of the titled compound as a colorless oil (Yield: 38.7%).

¹H-NMR (CDCl₃) δ 7.64-7.61 (m, 2H), 7.44-7.41 (m, 2H), 3.93 (t, 2H), 2.85 (t, 2H), 2.60 (q, 4H), 1.03 (t, 6H)

Preparation 6. 4-(4-bromo-2-fluorophenyl)-1-(2-hydroxy-2-methylpropyl)-1H-1,2,4-triazol-5(4H)-one To a solution of 4-(4-bromo-2-fluorophenyl)-1H-1,2,4-triazol-5(4H)-one (500.0 mg) prepared in Step 2 of Preparation 1 in N,N-dimethylformamide (20.0 mL), was added potassium carbonate (536.0 mg). The reaction mixture was stirred at room temperature for 10 minutes and then 1,2-epoxy-2-methylpropane (345.0 μL) was added thereto. The reaction mixture was stirred at 45° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give 245.0 mg of the titled compound as a white solid (Yield: 38.1%).

¹H-NMR (CDCl₃) δ 7.71 (s, 1H), 7.62 (t, 1H), 7.46-7.44 (m, 2H), 3.91 (s, 2H), 3.30 (s, 1H), 1.30 (s, 6H)

Preparation 7. 4-(4-bromo-2-fluorophenyl)-1-isobutyl-1H-1,2,4-triazol-5(4H)-one

To a solution of 4-(4-bromo-2-fluorophenyl)-1H-1,2,4-triazol-5(4H)-one (500.0 mg) prepared in Step 2 of Preparation 1 in N,N-dimethylformamide (15.0 mL), was added potassium hydroxide (217.0 mg). The reaction mixture was stirred at room temperature for 10 minutes and then 1-bromo-2-methylpropane (215.0 μL) was added thereto. The reaction mixture was stirred at 60° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=2/1) to give 597.0 mg of the titled compound as a yellow solid (Yield: 98.0%).

¹H-NMR (CDCl₃) δ 7.76 (s, 1H), 7.62 (t, 1H), 7.44-7.39 (m, 2H), 3.65 (d, 2H), 2.21-2.17 (m, 1H), 0.97 (d, 6H)

Preparation 8. 4-(4-bromo-2-fluorophenyl)-1-neopentyl-1H-1,2,4-triazol-5(4H)-one To a solution of 4-(4-bromo-2-fluorophenyl)-1H-1,2,4-triazol-5(4H)-one (500.0 mg) prepared in Step 2 of Preparation 1 in N,N-dimethylformamide (15.0 mL), was added potassium hydroxide (217.0 mg). The reaction mixture was stirred at room temperature for 10 minutes and then neopentyl bromide (249.0 μL) was added thereto. The reaction mixture was stirred at 60° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=2/1) to give 629.5 mg of the titled compound as a yellow solid (Yield: 99.0%).

¹H-NMR (CDCl₃) δ 6.91 (s, 1H), 6.79 (t, 1H), 6.72-6.66 (m, 2H), 2.79 (s, 2H), 0.18 (s, 9H)

Preparation 9. Methyl-2-[4-(4-bromo-2-fluorophenyl)-5-oxo-4,5-dihydro-1H-1,2,4-triazol-1-yl]acetate To a solution of 4-(4-bromo-2-fluorophenyl)-1H-1,2,4-triazol-5(4H)-one (200.0 mg) prepared in Step 2 of Preparation 1 in N,N-dimethylformamide (10.0 mL), was added potassium carbonate (353.0 mg). The reaction mixture was stirred at room temperature for 10 minutes and then methyl bromoacetate (121.0 μL) was added thereto. The reaction mixture was stirred at 80° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give 250.8 mg of the titled compound as a white solid (Yield: 98.0%).

¹H-NMR (CDCl₃) δ 7.78 (s, 1H), 7.63 (t, 1H), 7.47-7.45 (m, 2H), 4.66 (s, 2H), 3.80 (s, 3H)

Preparation 10. 4-(4-bromo-2-fluorophenyl)-1-[2-(pyrrolidin-1-yl)ethyl]-1H-1,2,4-triazol-5(4H)-one To a solution of 4-(4-bromo-2-fluorophenyl)-1H-1,2,4-triazol-5(4H)-one (500.0 mg) prepared in Step 2 of Preparation 1 in N,N-dimethylformamide (10.0 mL), was added NaH (155.2 mg). The reaction mixture was stirred at room temperature for 30 minutes and then 1-(2-chloroethyl)pyrrolidine hydrochloride (396.0 mg) was added thereto. The reaction mixture was stirred at 70° C. for 12 hours, cooled to room temperature, and then concentrated under reduced pressure. Ethyl acetate (20.0 mL) and brine (20.0 mL) were added to the residue and then the organic layer was separated. Ethyl acetate (20.0 mL) was added to the water layer and then the organic layer was separated. The combined organic layer was dried over anhydrous sodium sulfate and then concentrated under reduced pressure to give a colorless oily residue. The residue was purified with silica gel column chromatography (dichloromethane/methanol=20/1) to give 618.0 mg of the titled compound as a white solid (Yield: 89.7%).

¹H-NMR (CDCl₃) δ 7.66 (s, 1H), 7.65 (t, 1H), 7.50-7.42 (m, 2H), 4.01 (t, 2H), 2.85 (t, 2H), 2.60 (s, 4H), 1.79 (s, 4H)

Preparation 11. 4-(4-bromo-2-fluorophenyl)-1-(2-morpholinoethyl)-1H-1,2,4-triazol-5(4H)-one To a solution of 4-(4-bromo-2-fluorophenyl)-1H-1,2,4-triazol-5(4H)-one (1.0 g) prepared in Step 2 of Preparation 1 in N,N-dimethylformamide (50.0 mL), was added NaH (310.0 mg). The reaction mixture was stirred at room temperature for 30 minutes and then 4-(2-chloroethyl)morpholine hydrochloride (865.0 mg) was added thereto. The reaction mixture was stirred at 70° C. for 12 hours, cooled to room temperature, and then concentrated under reduced pressure. Ethyl acetate (50.0 mL) and brine (50.0 mL) were added to the residue and then the organic layer was separated. Ethyl acetate (50.0 mL) was added to the water layer and then the organic layer was separated. The combined organic layer was dried over anhydrous sodium sulfate and then concentrated under reduced pressure to give a colorless oily residue. The residue was purified with silica gel column chromatography (dichloromethane/methanol=20/1) to give 788.0 mg of the titled compound as a white solid (Yield: 54.7%).

$^1$H-NMR (CDCl$_3$) δ 7.65 (s, 1H), 7.62 (t, 1H), 7.50-7.43 (m, 2H), 3.99 (t, 2H), 3.68 (s, 4H), 2.76 (t, 2H), 2.54 (s, 4H)

Preparation 12. tert-butyl 2-[4-(4-bromo-2-fluorophenyl)-5-oxo-4,5-dihydro-1H-1,2,4-triazol-1-yl]ethyl(isopropyl)carbamate To a solution of 4-(4-bromo-2-fluorophenyl)-1H-1,2,4-triazol-5(4H)-one (1.0 g) prepared in Step 2 of Preparation 1 in N,N-dimethylformamide (50.0 mL), was added NaH (310.0 mg). The reaction mixture was stirred at room temperature for 30 minutes and then tert-butyl 2-bromoethyl(isopropyl)carbamate (1.2 g) was added thereto. The reaction mixture was stirred at 55° C. for 12 hours, cooled to room temperature, and then concentrated under reduced pressure. Ethyl acetate (25.0 mL) and brine (25.0 mL) were added to the residue and then the organic layer was separated. Ethyl acetate (25.0 mL) was added to the water layer and then the organic layer was separated. The combined organic layer was dried over anhydrous sodium sulfate and then concentrated under reduced pressure to give a colorless oily residue. The residue was purified with silica gel column chromatography (dichloromethane/methanol=20/1) to give 813.0 mg of the titled compound as a white solid (Yield: 47.5%).

$^1$H-NMR (CDCl$_3$) δ 7.65 (s, 1H), 7.62 (t, 1H), 7.50-7.43 (m, 2H), 4.04 (t, 2H), 3.55-3.30 (m, 3H), 1.51 (s, 9H), 1.13 (d, 6H)

Preparation 13. tert-butyl 2-[4-(4-bromo-2-fluorophenyl)-5-oxo-4,5-dihydro-1H-1,2,4-triazol-1-yl]ethylcarbamate To a solution of 4-(4-bromo-2-fluorophenyl)-1H-1,2,4-triazol-5(4H)-one (2.8 g) prepared in Step 2 of Preparation 1 in N,N-dimethylformamide (50.0 mL), was added NaH (644.1 mg). The reaction mixture was stirred at 0° C. for 30 minutes and then tert-butyl 2-bromoethylcarbamate (2.7 g) was added thereto. The reaction mixture was stirred at 55° C. for 12 hours, cooled to room temperature, and then concentrated under reduced pressure. Ethyl acetate (25.0 mL) and brine (25.0 mL) were added to the residue and then the organic layer was separated. Ethyl acetate (25.0 mL) was added to the water layer and then the organic layer was separated. The combined organic layer was dried over anhydrous sodium sulfate and then concentrated under reduced pressure to give a colorless oily residue. The residue was purified with silica gel column chromatography (dichloromethane/methanol=20/1) to give 2.2 g of the titled compound as a white solid (Yield: 51.2%).

$^1$H-NMR (CDCl$_3$) δ 7.65 (s, 1H), 7.62 (t, 1H), 7.50-7.43 (m, 2H), 5.04 (s, 1H), 3.99 (t, 2H), 3.60-3.50 (m, 2H), 1.42 (s, 9H)

Preparation 14. 2-[4-(4-bromo-2-fluorophenyl)-5-oxo-4,5-dihydro-1H-1,2,4-triazol-1-yl]acetonitrile To a solution of 4-(4-bromo-2-fluorophenyl)-1H-1,2,4-triazol-5(4H)-one (500.0 mg) prepared in Step 2 of Preparation 1 in N,N-dimethylformamide (20.0 mL), was added potassium carbonate (1.07 g). The reaction mixture was stirred at room temperature for 10 minutes and then chloroacetonitrile (220.8 μL) was added thereto. The reaction mixture was stirred at 80° C. for 12 hours, cooled to room temperature, and then concentrated under reduced pressure. Ethyl acetate (30.0 mL) and brine (30.0 mL) were added to the residue and then the organic layer was separated. Ethyl acetate (30.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=1/1) to give 414.6 mg of the titled compound as a white solid (Yield: 72.2%).

$^1$H-NMR (CDCl$_3$) δ 7.74 (s, 1H), 7.58 (t, 1H), 7.49-7.44 (m, 2H), 4.80 (s, 2H)

Preparation 15. 4-(4-bromo-2-fluorophenyl)-1-trityl-1H-1,2,4-triazol-5(4H)-one

To a solution of 4-(4-bromo-2-fluorophenyl)-1H-1,2,4-triazol-5(4H)-one (5.0 g) prepared in Step 2 of Preparation 1 in N,N-dimethylformamide (50.0 mL), was added NaH (930.0 mg). The reaction mixture was stirred at room temperature for 30 minutes and then trityl chloride (5.67 g) was added thereto. The reaction mixture was stirred at room temperature for 12 hours and then concentrated under reduced pressure. Ethyl acetate (30.0 mL) and brine (30.0 mL) were added to the residue and then the organic layer was separated. Ethyl acetate (30.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=3/1) to give 3.88 g of the titled compound as a white solid (Yield: 40.0%).

$^1$H-NMR (CDCl$_3$) δ 7.72 (s, 1H), 7.51 (t, 1H), 7.38-7.28 (m, 17H)

Preparation 16. N-{2-[4-(4-bromo-2-fluorophenyl)-5-oxo-4,5-dihydro-1H-1,2,4-triazol-1-yl]ethyl}methanesulfonamide To a solution of 4-(4-bromo-2-fluorophenyl)-1H-1,2,4-triazol-5(4H)-one (5.0 g) prepared in Step 2 of Preparation 1 in N,N-dimethylformamide (50.0 mL), was added NaH (930.0 mg). The reaction mixture was stirred at room temperature for 30 minutes and then N-(2-bromoethyl)methanesulfonamide (7.8 g) was added thereto. The reaction mixture was stirred at 55° C. for 12 hours and then concentrated under reduced pressure. Ethyl acetate (30.0 mL) and brine (30.0 mL) were added to the residue and then the organic layer was separated. Ethyl acetate (30.0 mL) was added to the water layer and then the organic layer was separated. The combined organic layer was dried over anhydrous sodium sulfate and then concentrated under reduced pressure to give a colorless oily residue. The residue was purified with silica gel column chromatography (dichloromethane/methanol=20/1) to give 3.7 g of the titled compound as a white solid (Yield: 50.7%).

$^1$H-NMR (CDCl$_3$) δ 7.65 (s, 1H), 7.62 (t, 1H), 7.50-7.43 (m, 2H), 6.99 (s, 1H), 3.42 (t, 2H), 2.95 (s, 3H), 2.86 (m, 2H)

Preparation 17. (S)-4-(4-bromo-2-fluorophenyl)-1-(tetrahydrofuran-3-yl)-1H-1,2,4-triazol-5(4H)-one To a solution of 4-(4-bromo-2-fluorophenyl)-1H-1,2,4-triazol-5(4H)-one (2.4 g) prepared in Step 2 of Preparation 1 in N,N-dimethylformamide (50.0 mL), was added NaH (757.0 mg). The reaction mixture was stirred at room temperature for 30 minutes and then (R)-tetrahydrofuran-3-yl methanesulfonate (1.9 g) was added thereto. The reaction mixture was stirred at 80° C. for 12 hours and then concentrated under reduced pressure. Ethyl acetate (25.0 mL) and brine (25.0 mL) were added to the residue and then the organic layer was separated. Ethyl acetate (25.0 mL) was added to the water layer and then the organic layer was separated. The combined organic layer was dried over anhydrous sodium sulfate and then concentrated under reduced pressure to give a yellow oily residue. The residue was purified with silica gel column chromatography (dichloromethane/methanol=20/1) to give 1.9 g of the titled compound as a yellow oil (Yield: 61.8%).

$^1$H-NMR (CDCl$_3$) δ 7.66 (s, 1H), 7.63 (t, 1H), 7.50-7.40 (m, 2H), 5.00-4.90 (m, 1H), 4.20-4.10 (m, 1H), 4.10-4.05 (m, 1H), 4.05-3.90 (m, 2H), 2.42-2.28 (m, 2H)

Preparation 18. (R)-tert-butyl 3-[4-(4-bromo-2-fluorophenyl)-5-oxo-4,5-dihydro-1H-1,2,4-triazol-1-yl]pyrrolidin-1-carboxylate To a solution of 4-(4-bromo-2-fluorophenyl)-1H-1,2,4-triazol-5(4H)-one (2.5 g) prepared in Step 2 of Preparation 1 in N,N-dimethylformamide (50.0 mL), was added NaH (765.6 mg). The reaction mixture was stirred at room temperature for 30 minutes and then (S)-tert-butyl 3-(methylsulfonyloxy)pyrrolidin-1-carboxylate (3.0 g) was added thereto. The reaction mixture was stirred at 80° C. for 12 hours and then concentrated under reduced pressure. Ethyl acetate (25.0 mL) and brine (25.0 mL) were added to the residue and then the organic layer was separated. Ethyl acetate (25.0 mL) was added to the water layer and then the organic layer was separated. The combined organic layer was dried over anhydrous sodium sulfate and then concentrated under reduced pressure to give a yellow oily residue. The residue was purified with silica gel column chromatography (dichloromethane/methanol=20/1) to give 1.8 g of the titled compound as a yellow oil (Yield: 44.0%).

$^1$H-NMR (CDCl$_3$) δ 7.65 (s, 1H), 7.61 (t, 1H), 7.50-7.40 (m, 2H), 4.92-4.87 (m, 1H), 3.79-3.74 (m, 1H), 3.67-3.60 (m, 2H), 3.50-3.40 (m, 1H), 2.35-2.25 (m, 2H), 1.47 (s, 9H)

Preparation 19. 4-(4-bromo-2-fluorophenyl)-1-(methoxymethyl)-1H-1,2,4-triazol-5(4H)-one To a solution of 4-(4-bromo-2-fluorophenyl)-1H-1,2,4-triazol-5(4H)-one (1.0 g) prepared in Step 2 of Preparation 1 in N,N-dimethylformamide (40.0 mL), was added NaH (200.0 mg). The reaction mixture was stirred at room temperature for 30 minutes and then 2-bromomethyl methyl ether (620.0 mg) was added thereto. The reaction mixture was stirred at 60° C. for 12 hours and then concentrated under reduced pressure. Ethyl acetate (20.0 mL) and brine (20.0 mL) were added to the residue and then the organic layer was separated. Ethyl acetate (20.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=1/2) to give 530.6 mg of the titled compound as a yellow oil (Yield: 37.4%).

$^1$H-NMR (CDCl$_3$) δ 7.65 (s, 1H), 7.61 (t, 1H), 7.50-7.40 (m, 2H), 5.22 (s, 2H), 3.49 (s, 3H)

Preparation 20. ethyl 4-(4-bromo-2-fluorophenyl)-5-oxo-4,5-dihydro-1H-1,2,4-triazol-1-carboxylate To a solution of 4-(4-bromo-2-fluorophenyl)-1H-1,2,4-triazol-5(4H)-one (5.0 g) prepared in Step 2 of Preparation 1 in N,N-dimethylformamide (125.0 mL), was added potassium carbonate (8.8 g). The reaction mixture was stirred at room temperature for 10 minutes and then ethyl chloroformate (3.6 mL) was added thereto. The reaction mixture was stirred at 80° C. for 12 hours and then concentrated under reduced pressure. Ethyl acetate (50.0 mL) and brine (50.0 mL) were added to the residue and then the organic layer was separated. Ethyl acetate (50.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=1/2) to give 4.2 g of the titled compound as a yellow oil (Yield: 65.6%).

$^1$H-NMR (CDCl$_3$) δ 7.72 (s, 1H), 7.64 (t, 1H), 7.50-7.40 (m, 2H), 4.24 (q, 2H), 1.30 (t, 3H)

Preparation 21. 3-[4-(4-bromo-2-fluorophenyl)-5-oxo-4,5-dihydro-1H-1,2,4-triazol-1-yl]-2,2-dimethyl propanenitrile To a solution of 4-(4-bromo-2-fluorophenyl)-1H-1,2,4-triazol-5(4H)-one (500.0 mg) prepared in Step 2 of Preparation 1 in N,N-dimethylformamide (20.0 mL), was added potassium carbonate (536.0 mg). The reaction mixture was stirred at room temperature for 10 minutes and then cyclopropanecarbonitrile (245.0 μL) was added thereto. The reaction mixture was stirred at 45° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give 185.0 mg of the titled compound as a white solid (Yield: 29.8%).

$^1$H-NMR (CDCl$_3$) δ 7.71 (s, 1H), 7.62 (t, 1H), 7.46-7.44 (m, 2H), 3.45 (s, 2H), 1.46 (s, 6H)

Preparation 22. 4-(4-bromo-2-fluorophenyl)-1-(morpholinomethyl)-1H-1,2,4-triazol-5(4H)-one To a solution of 4-(4-bromo-2-fluorophenyl)-1H-1,2,4-triazol-5(4H)-one (80.0 mg) prepared in Step 2 of Preparation 1 in ethanol (2.0 mL), were added morpholine (14.4 μL) and an aqueous solution of formaldehyde (37%, 330.0 mg). The reaction mixture was stirred at room temperature for 12 hours and then concentrated under reduced pressure to give 78.2 mg of the titled compound as a white solid (Yield: 81.2%).

$^1$H-NMR (CDCl$_3$) δ 7.72 (s, 1H), 7.64 (t, 1H), 7.50-7.40 (m, 2H), 4.75 (s, 2H), 3.73 (s, 4H), 2.77 (s, 4H)

Preparation 23. (S)-4-(4-bromo-2-fluorophenyl)-1-[(2,2-dimethyl-1,3-dioxolane-4-yl)methyl]-1H-1,2,4-triazol-5(4H)-one To a solution of 4-(4-bromo-2-fluorophenyl)-1H-1,2,4-triazol-5(4H)-one (2.0 g) prepared in Step 2 of Preparation 1 in N,N-dimethylformamide (70.0 mL), was added potassium carbonate (2.1 g). The reaction mixture was stirred at room temperature for 10 minutes and then (R)-4-(chloromethyl)-2,2-dimethyl-1,3-dioxolane (1.3 mL) was added thereto. The reaction mixture was stirred at 100° C. for 12 hours and then concentrated under reduced pressure. Ethyl acetate (40.0 mL) and brine (40.0 mL) were added to the residue and then the organic layer was separated. Ethyl acetate (40.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=1/2) to give 539.7 mg of the titled compound as a yellow oil (Yield: 18.7%).

$^1$H-NMR (CDCl$_3$) δ 7.67 (s, 1H), 7.65 (t, 1H), 7.50-7.40 (m, 2H), 4.55-4.45 (m, 1H), 4.15-4.04 (m, 2H), 3.94-3.85 (m, 2H), 1.46 (s, 3H), 1.37 (s, 3H)

Preparation 24. 4-(4-bromo-2-fluorophenyl)-1-[2-oxo-2-(pyrrolidin-1-yl)ethyl]-1H-1,2,4-triazol-5(4H)-one To a solution of 4-(4-bromo-2-fluorophenyl)-1H-1,2,4-triazol-5(4H)-one (100.0 mg) prepared in Step 2 of Preparation 1 in N,N-dimethylformamide (5.0 mL), was added sodium hydroxide (150.0 mg). The reaction mixture was stirred at room temperature for 10 minutes and then 2-bromo-1-(pyrrolidin-1-yl)ethanone (90.0 mg) was added thereto. The reaction mixture was stirred at 60° C. for 12 hours and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a yellow oily residue. The residue was purified with silica gel column chromatography (dichloromethane/methanol=20/1) to give 30.6 mg of the titled compound as a white solid (Yield: 40.3%).

$^1$H-NMR (CDCl$_3$) δ 7.67 (s, 1H), 7.65 (t, 1H), 7.50-7.40 (m, 2H), 4.05 (s, 2H), 3.09 (s, 4H), 1.83 (s, 4H)

Preparation 25. 4-(4-bromo-2,5-difluorophenyl)-1-methyl-1H-1,2,4-triazol-5(4H)-one The intermediate (2.0 g) was prepared in accordance with the same procedures as in Step 2 of Preparation 1, using 4-bromo-2,5-difluoroaniline (5.0 g), instead of 4-bromo-2-fluoroaniline. To a solution of the resulting intermediate in N,N-dimethylformamide (10.0 mL), was added sodium hydroxide (80.0 mg). The reaction mixture was stirred at room temperature for 10 minutes and then iodomethane (200.0 mg) was added thereto. The reaction mixture was stirred at 60° C. for 12 hours and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=2/1) to give 47.6 mg of the titled compound as a white solid (Yield: 32.3%).

$^1$H-NMR (CDCl$_3$) δ 7.62 (s, 1H), 7.50 (s, 1H), 7.34 (s, 1H), 2.74 (s, 3H)

Preparation 26. 4-(4-bromo-3-fluorophenyl)-1-isopropyl-1H-1,2,4-triazol-5(4H)-one The intermediate (2.3 g) was prepared in accordance with the same procedures as in Step 2 of Preparation 1, using 4-bromo-3-fluoroaniline (5.0 g), instead of 4-bromo-2-fluoroaniline. To a solution of the resulting intermediate in N,N-dimethylformamide (10.0 mL), was added sodium hydroxide (80.0 mg). The reaction mixture was stirred at room temperature for 10 minutes and then 2-bromopropane (72.8 μL) was added thereto. The reaction mixture was stirred at 60° C. for 12 hours and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=2/1) to give 29.7 mg of the titled compound as a white solid (Yield: 22.4%).

$^1$H-NMR (CDCl$_3$) δ 8.49 (d, 1H), 7.64 (s, 1H), 7.56 (d, 1H), 7.50 (s, 1H), 4.00-3.90 (m, 1H), 1.27 (s, 6H)

Preparation 27. 4-(4-bromophenyl)-1-methyl-1H-1,2,4-triazol-5(4H)-one

The intermediate (2.4 g) was prepared in accordance with the same procedures as in Step 2 of Preparation 1, using 4-bromoaniline (5.0 g), instead of 4-bromo-2-fluoroaniline. To a solution of the resulting intermediate in N,N-dimethylformamide (10.0 mL), was added NaH (80.0 mg). The reaction mixture was stirred at room temperature for 10 minutes and then iodomethane (200.0 mg) was added thereto. The reaction mixture was stirred at 60° C. for 12 hours and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=2/1) to give 320.6 mg of the titled compound as a white solid (Yield: 35.3%).

$^1$H-NMR (CDCl$_3$) δ 7.74 (s, 1H), 7.69 (dd, 2H), 7.60 (dd, 2H), 3.54 (s, 3H)

Preparation 28. N-{2-[4-(4-bromo-2-fluorophenyl)-5-oxo-4,5-dihydro-1H-1,2,4-triazol-1-yl]ethyl}acetamide To a solution of 4-(4-bromo-2-fluorophenyl)-1H-1,2,4-triazol-5(4H)-one (5.0 g) prepared in Step 2 of Preparation 1 in N,N-dimethylformamide (50.0 mL), was added NaH (930.0 mg). The reaction mixture was stirred at room temperature for 30 minutes and then N-(2-bromoethyl)acetamide (6.5 g) was added thereto. The reaction mixture was stirred at 55° C. for 12 hours and then concentrated under reduced pressure. Ethyl acetate (30.0 mL) and brine (30.0 mL) were added to the residue and then the organic layer was separated. Ethyl acetate (30.0 mL) was added to the water layer and then the organic layer was separated. The combined organic layer was dried over anhydrous sodium sulfate and then concentrated under reduced pressure to give a colorless oily residue. The residue was purified with silica gel column chromatography (dichloromethane/methanol=20/1) to give 3.7 g of the titled compound as a white solid (Yield: 50.7%).

$^1$H-NMR (CDCl$_3$) δ 8.01 (s, 1H), 7.65 (s, 1H), 7.62 (t, 1H), 7.50-7.43 (m, 2H), 3.66 (t, 2H), 3.42 (t, 2H), 1.84 (s, 3H)

Preparation 29. 4-(4-bromophenyl)-1-(2-methoxyethyl)-1H-1,2,4-triazol-5(4H)-one

The titled compound (35.7 mg) as a white solid was prepared in accordance with the same procedures as in Preparation 27, using 2-bromoethyl methyl ether (50.0 mg) instead of iodomethane (Yield: 44.7%).

$^1$H-NMR (CDCl$_3$) δ 7.74 (s, 1H), 7.69 (dd, 2H), 7.60 (dd, 2H), 4.07 (t, 2H), 3.81 (t, 2H), 3.49 (s, 3H)

Preparation 30. (R)-4-(4-bromophenyl)-1-(tetrahydrofuran-3-yl)-1H-1,2,4-triazol-5(4H)-one The titled compound (40.2 mg) as a white solid was prepared in accordance with the same procedures as in Preparation 27, using (S)-tetrahydrofuran-3-yl methanesulfonate (50.0 mg), instead of iodomethane (Yield: 49.5%).

$^1$H-NMR (CDCl$_3$) δ 7.74 (s, 1H), 7.69 (dd, 2H), 7.60 (dd, 2H), 5.00-4.90 (m, 1H), 4.20-4.10 (m, 1H), 4.10-4.05 (m, 1H), 4.05-3.90 (m, 2H), 2.42-2.28 (m, 2H)

Preparation 31. 4-(4-bromo-2-fluorophenyl)-1-[(4-methylpiperazin-1-yl)methyl]-1H-1,2,4-triazol-5(4H)-one To a solution of 4-(4-bromo-2-fluorophenyl)-1H-1,2,4-triazol-5(4H)-one (80.0 mg) prepared in Step 2 of Preparation 1 in ethanol (2.0 mL), were added 1-methylpiperazine (18.3 mg) and an aqueous solution of formaldehyde (37%, 330.0 mg). The reaction mixture was stirred at room temperature for 12 hours and then concentrated under reduced pressure to give 40.0 mg of the titled compound as a white solid (Yield: 40.6%).

$^1$H-NMR (CDCl$_3$) δ 7.72 (s, 1H), 7.64 (t, 1H), 7.50-7.40 (m, 2H), 4.79 (s, 2H), 2.82 (s, 4H), 2.48 (s, 4H), 2.29 (s, 3H)

Preparation 32. (R)-4-(4-bromo-2-fluorophenyl)-1-(tetrahydrofuran-3-yl)-1H-1,2,4-triazol-5(4H)-one To a solution of 4-(4-bromo-2-fluorophenyl)-1H-1,2,4-triazol-5(4H)-one (2.4 g) prepared in Step 2 of Preparation 1 in N,N-dimethylformamide (50.0 mL), was added NaH (757.0 mg). The reaction mixture was stirred at room temperature for 30 minutes and then (S)-tetrahydrofuran-3-yl methanesulfonate (1.9 g) was added thereto. The reaction mixture was stirred at 80° C. for 12 hours and then concentrated under reduced pressure. Ethyl acetate (25.0 mL) and brine (25.0 mL) were added to the residue and then the organic layer was separated. Ethyl acetate (25.0 mL) was added to the water layer and then the organic layer was separated. The combined organic layer was dried over anhydrous sodium sulfate and then concentrated under reduced pressure to give a yellow oily residue. The residue was purified with silica gel column chromatography (dichloromethane/methanol=20/1) to give 1.9 g of the titled compound as a yellow oil (Yield: 61.8%).

$^1$H-NMR (CDCl$_3$) δ 7.66 (s, 1H), 7.63 (t, 1H), 7.50-7.40 (m, 2H), 5.00-4.90 (m, 1H), 4.20-4.10 (m, 1H), 4.10-4.05 (m, 1H), 4.05-3.90 (m, 2H), 2.42-2.28 (m, 2H)

Preparation 33. 4-(4-bromo-2-fluorophenyl)-1-(pyrrolidin-1-ylmethyl)-1H-1,2,4-triazol-5(4H)-one To a solution of 4-(4-bromo-2-fluorophenyl)-1H-1,2,4-triazol-5(4H)-one (80.0 mg) prepared in Step 2 of Preparation 1 in ethanol (2.0 mL), were added pyrrolidine (13.6 μL) and an aqueous solution of formaldehyde (37%, 330.0 mg). The reaction mixture was stirred at room temperature for 12 hours and then concentrated under reduced pressure to give 50.7 mg of the titled compound as a white solid (Yield: 53.9%).

$^1$H-NMR (CDCl$_3$) δ 7.72 (s, 1H), 7.64 (t, 1H), 7.50-7.40 (m, 2H), 4.86 (s, 2H), 2.84 (s, 4H), 1.79 (s, 4H)

Preparation 34. 4-(4-bromophenyl)-1-ethyl-1H-1,2,4-triazol-5(4H)-one

The titled compound (30.2 mg) as a white solid was prepared in accordance with the same procedures as in Preparation 27, using iodoethane (50.0 mg), instead of iodomethane (Yield: 48.8%).

$^1$H-NMR (CDCl$_3$) δ 7.74 (s, 1H), 7.69 (dd, 2H), 7.60 (dd, 2H), 4.13 (q, 2H), 1.31 (t, 3H)

Preparation 35. 4-(4-bromophenyl)-1-(methoxymethyl)-1H-1,2,4-triazol-5(4H)-one

The titled compound (28.7 mg) as a white solid was prepared in accordance with the same procedures as in Preparation 27, using 2-bromomethyl methyl ether (50.0 mg), instead of iodomethane (Yield: 42.6%).

$^1$H-NMR (CDCl$_3$) δ 7.74 (s, 1H), 7.69 (dd, 2H), 7.60 (dd, 2H), 5.22 (s, 2H), 3.49 (s, 3H)

Preparation 36. (S)-4-(4-bromophenyl)-1-(tetrahydrofuran-3-yl)-1H-1,2,4-triazol-5(4H)-one The titled compound (30.7 mg) as a white solid was prepared in accordance with the same procedures as in Preparation 27, using (R)-tetrahydrofuran-3-yl methanesulfonate (50.0 mg), instead of iodomethane (Yield: 45.2%).

$^1$H-NMR (CDCl$_3$) δ 7.74 (s, 1H), 7.69 (dd, 2H), 7.60 (dd, 2H), 5.00-4.90 (m, 1H), 4.20-4.10 (m, 1H), 4.10-4.05 (m, 1H), 4.05-3.90 (m, 2H), 2.42-2.28 (m, 2H)

Preparation 37. (S)-tert-butyl 3-[4-(4-bromophenyl)-5-oxo-4,5-dihydro-1H-1,2,4-triazol-1-yl]pyrrolidin-1-carboxylate The titled compound (27.8 mg) as a white solid was prepared in accordance with the same procedures as in Preparation 27, using (R)-tert-butyl 3-(methylsulfonyloxy)pyrrolidin-1-carboxylate (50.0 mg), instead of iodomethane (Yield: 30.6%).

$^1$H-NMR (CDCl$_3$) δ 7.74 (s, 1H), 7.69 (dd, 2H), 7.60 (dd, 2H), 4.92-4.87 (m, 1H), 3.79-3.74 (m, 1H), 3.67-3.60 (m, 2H), 3.50-3.40 (m, 1H), 2.35-2.25 (m, 2H), 1.47 (s, 9H)

Preparation 38. 2-[4-(4-bromophenyl)-5-oxo-4,5-dihydro-1H-1,2,4-triazol-1-yl]acetamide The titled compound (37.8 mg) as a white solid was prepared in accordance with the same procedures as in Preparation 27, using 2-bromoacetamide (50.0 mg), instead of iodomethane (Yield: 42.6%).

¹H-NMR (CDCl₃) δ 7.74 (s, 1H), 7.69 (dd, 2H), 7.60 (dd, 2H), 7.21 (s, 2H), 4.50 (s, 2H)

Preparation 39. 4-(4-bromophenyl)-1-isopropyl-1H-1,2,4-triazol-5(4H)-one

The titled compound (357.2 mg) as a white solid was prepared in accordance with the same procedures as in Preparation 27, using 2-iodopropane (425.0 mg), instead of iodomethane (Yield: 60.8%).

¹H-NMR (CDCl₃) δ 7.67 (s, 1H), 7.60 (dd, 2H), 7.48 (dd, 2H), 4.58-4.52 (m, 1H), 1.42 (d, 6H)

Example 1

(S)-tert-butyl 4-(5-(3-fluoro-4-(1-methyl-5-oxo-1H-1,2,4-triazol-4(5H)-yl)phenyl)pyrimidin-2-yl)-3-methylpiperazin-1-carboxylate Step 1: (S)-tert-butyl 4-(5-bromopyrimidin-2-yl)-3-methylpiperazin-1-carboxylate To a solution of 5-bromo-2-chloropyrimidine (7.7 g) in N,N-dimethylformamide (250.0 mL), was added cesium carbonate (19.5 g). The reaction mixture was stirred at room temperature for 10 minutes and then (S)-4-N—BOC-2-methylpiperazine (8.0 g) was added thereto. The reaction mixture was stirred at 100° C. for 12 hours, cooled to room temperature, and then concentrated under reduced pressure. Ethyl acetate (100.0 mL) and brine (100.0 mL) were added to the residue and then the organic layer was separated. Ethyl acetate (100.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=5/1) to give 5.3 g of the titled compound as a white solid (Yield: 37.1%).

¹H-NMR (CDCl₃) δ 8.30 (s, 2H), 4.80 (s, 1H), 4.39 (d, 1H), 4.15-4.11 (m, 2H), 3.17 (t, 1H), 3.17-2.90 (m, 2H), 1.49 (s, 9H), 1.18 (d, 3H)

Step 2: (S)-tert-butyl 3-methyl-4-[5-(4,4,5,5-tetramethyl-1,3,2-dioxaborolan-2-yl)pyrimidin-2-yl]piperazin-1-carboxylate To a solution of (S)-tert-butyl 4-(5-bromopyrimidin-2-yl)-3-methylpiperazin-1-carboxylate (5.3 g) prepared in Step 1 in 1,4-dioxane (165.0 mL), were added potassium acetate (4.4 g), bis(pinacolato)diboron (4.1 g), 2-dicyclohexylphosphino-2',4',6'-triisopropylbiphenyl (423.3 mg) and tris(dibenzylideneacetone)dipalladium(0) (406.6 mg). The reaction mixture was stirred at 100° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give yellow oily residue. The residue was purified with silica gel column chromatography (hexane/ethyl acetate=5/1) to give 4.8 g of the titled compound as a white solid (Yield: 80.4%).

¹H-NMR (CDCl₃) δ 8.31 (s, 2H), 4.98 (s, 1H), 4.56 (d, 1H), 4.23-3.80 (m, 2H), 3.18 (t, 1H), 3.15-2.80 (m, 2H), 1.49 (s, 9H), 1.32 (s, 12H) 1.19 (d, 3H)

Step 3: (S)-tert-butyl 4-(5-(3-fluoro-4-(1-methyl-5-oxo-1H-1,2,4-triazol-4(5H)-yl)phenyl)pyrimidin-2-yl)-3-methylpiperazin-1-carboxylate To a solution of (S)-tert-butyl 3-methyl-4-[5-(4,4,5,5-tetramethyl-1,3,2-dioxaborolan-2-yl)pyrimidin-2-yl]piperazin-1-carboxylate (123.0 mg) prepared in Step 2, 4-(4-bromo-2-fluorophenyl)-1-methyl-1H-1,2,4-triazol-5(4H)-one (82.6 mg) prepared in Preparation 1 and tetrakis(triphenylphosphine)palladium(0) (17.6 mg) in N,N-dimethylformamide (3.0 mL), was added an aqueous solution of sodium carbonate (2.0 M, 0.5 mL). The reaction mixture was stirred at 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give yellow oily residue. The residue was purified with silica gel column chromatography (hexane/ethyl acetate=1/2) to give 21.5 mg of the titled compound as a white solid (Yield: 16.4%).

¹H-NMR (CDCl₃) δ 8.55 (s, 2H), 7.75 (t, 1H), 7.68 (s, 1H), 7.42-7.31 (m, 2H), 4.95 (s, 1H), 4.54 (d, 1H), 4.30-3.85 (m, 2H), 3.56 (s, 3H), 3.25 (t, 1H), 3.20-2.82 (m, 2H), 1.50 (s, 9H), 1.24 (d, 3H)

Example 2

(S)-tert-butyl 4-(5-(3-fluoro-4-(5-oxo-1-propyl-1H-1,2,4-triazol-4(5H)-yl)phenyl)pyrimidin-2-yl)-3-methylpiperazin-1-carboxylate The titled compound was prepared in accordance with the same procedures as in Step 3 of Example 1, using 4-(4-bromo-2-fluorophenyl)-1-propyl-1H-1,2,4-triazol-5(4H)-one (53.8 mg) prepared in Preparation 2 instead of 4-(4-bromo-2-fluorophenyl)-1-methyl-1H-1,2,4-triazol-5(4H)-one.

Yield: 20.0%

¹H-NMR (CDCl₃) δ 8.55 (s, 2H), 7.78 (t, 1H), 7.68 (s, 1H), 7.42-7.30 (m, 2H), 4.95 (s, 1H), 4.54 (d, 1H), 4.30-3.90 (m, 2H), 3.84 (t, 2H), 3.25 (t, 1H), 3.20-2.85 (m, 2H), 1.90-1.80 (m, 2H), 1.49 (s, 9H), 1.24 (s, 3H), 1.00 (t, 3H)

Example 3

(S)-tert-butyl 4-(5-(3-fluoro-4-(1-isopropyl-5-oxo-1H-1,2,4-triazol-4(5H)-yl)phenyl)pyrimidin-2-yl)-3-methylpiperazin-1-carboxylate The titled compound was prepared in accordance with the same procedures as in Step 3 of Example 1, using 4-(4-bromo-2-fluorophenyl)-1-isopropyl-1H-1,2,4-triazol-5(4H)-one (45.3 mg) prepared in Preparation 3 instead of 4-(4-bromo-2-fluorophenyl)-1-methyl-1H-1,2,4-triazol-5(4H)-one.

Yield: 34.0%

¹H-NMR (CDCl₃) δ 8.55 (s, 2H), 7.78 (t, 1H), 7.68 (s, 1H), 7.42-7.30 (m, 2H), 4.95 (s, 1H), 4.62-4.48 (m, 2H), 4.28-3.85 (m, 2H), 3.25 (t, 1H), 3.20-2.85 (m, 2H), 1.50 (s, 9H), 1.44 (d, 6H), 1.23 (d, 3H)

Example 4

(S)-tert-butyl 4-(5-(3-fluoro-4-(1-(2-methoxyethyl)-5-oxo-1H-1,2,4-triazol-4(5H)-yl)phenyl)pyrimidin-2-yl)-3-methylpiperazin-1-carboxylate The titled compound was prepared in accordance with the same procedures as in Step 3 of Example 1, using 4-(4- bromo-2-fluorophenyl)-1-(2-methoxyethyl)-1H-1,2,4-triazol-5(4H)-one (40.6 mg) prepared in Preparation 4 instead of 4-(4-bromo-2-fluorophenyl)-1-methyl-1H-1,2,4-triazol-5(4H)-one.

Yield: 16.9%

$^1$H-NMR (CDCl$_3$) δ 8.55 (s, 2H), 7.79 (t, 1H), 7.70 (s, 1H), 7.42-7.31 (m, 2H), 4.95 (s, 1H), 4.54 (d, 1H), 4.28-3.90 (m, 2H), 4.08 (t, 2H), 3.77 (t, 2H), 3.41 (s, 3H), 3.26 (t, 1H), 3.20-2.85 (m, 2H), 1.50 (s, 9H), 1.24 (d, 3H)

Example 5

(S)-tert-butyl 4-(3-cyano-5-(3-fluoro-4-(5-oxo-1-propyl-1H-1,2,4-triazol-4(5H)-yl)phenyl)pyridin-2-yl)-3-methylpiperazin-1-carboxylate The intermediate (4.0 g) was prepared in accordance with the same procedures as in Steps 1 and 2 of Example 1, using 5-bromo-2-chloronicotinonitrile (10.0 g) instead of 5-bromo-2-chloropyrimidine. The titled compound was prepared in accordance with the same procedures as in Step 3 of Example 1, using the intermediate and 4-(4-bromo-2-fluorophenyl)-1-propyl-1H-1,2,4-triazol-5(4H)-one (67.4 mg) prepared in Preparation 2 instead of (S)-tert-butyl 3-methyl-4-[5-(4,4,5,5-tetramethyl-1,3,2-dioxaborolan-2-yl)pyrimidin-2-yl]piperazin-1-carboxylate and 4-(4-bromo-2-fluorophenyl)-1-methyl-1H-1,2,4-triazol-5(4H)-one, respectively.

Yield: 42.1%

$^1$H-NMR (CDCl$_3$) δ 8.56 (s, 1H), 7.96 (s, 1H), 7.84 (t, 1H), 7.71 (s, 1H), 7.46-7.32 (m, 2H), 4.75 (s, 1H), 4.21 (d, 1H), 4.13-3.88 (m, 2H), 3.85 (t, 2H), 3.45 (t, 1H), 3.32-2.97 (m, 2H), 1.85 (q, 2H), 1.50 (s, 9H), 1.33 (d, 3H), 1.00 (t, 3H)

Example 6

(S)-tert-butyl 4-(5-(3-fluoro-4-(5-oxo-1-propyl-1H-1,2,4-triazol-4(5H)-yl)phenyl)-3-(trifluoromethyl)pyridin-2-yl)-3-methylpiperazin-1-carboxylate The intermediate (2.4 g) was prepared in accordance with the same procedures as in Steps 1 and 2 of Example 1, using 5-bromo-2-chloro-3-(trifluoromethyl)-pyridine (3.1 g) instead of 5-bromo-2-chloropyrimidine. The titled compound was prepared in accordance with the same procedures as in Step 3 of Example 1, using the intermediate and 4-(4-bromo-2-fluorophenyl)-1-propyl-1H-1,2,4-triazol-5(4H)-one (35.8 mg) prepared in Preparation 2 instead of (S)-tert-butyl 3-methyl-4-[5-(4,4,5,5-tetramethyl-1,3,2-dioxaborolan-2-yl)pyrimidin-2-yl]piperazin-1-carboxylate and 4-(4-bromo-2-fluorophenyl)-1-methyl-1H-1,2,4-triazol-5(4H)-one, respectively.

Yield: 89.0%

$^1$H-NMR (CDCl$_3$) δ 8.74 (s, 1H), 8.08 (s, 1H), 7.89 (t, 1H), 7.73 (s, 1H), 7.54-7.42 (m, 2H), 3.85 (t, 2H), 3.81-3.62 (m, 3H), 3.55-3.40 (m, 1H), 3.26-3.00 (m, 3H), 1.86 (q, 2H), 1.49 (s, 9H), 1.00 (t, 3H), 0.99 (d, 3H)

Example 7

(S)-4-(4-(2-(4-(5-ethylpyrimidin-2-yl)-2-methylpiperazin-1-yl)pyrimidin-5-yl)-2-fluorophenyl)-1-methyl-1H-1,2,4-triazol-5(4H)-one The intermediate (850.0 mg) was prepared in accordance with the same procedures as in Steps 1 and 2 of Example 1, using (S)-5-ethyl-2-(3-methylpiperazin-1-yl)pyrimidine (1.0 g) instead of (S)-4-N—BOC-2-methylpiperazine. The titled compound was prepared in accordance with the same procedures as in Step 3 of Example 1, using the intermediate instead of (S)-tert-butyl 3-methyl-4-[5-(4,4,5,5-tetramethyl-1,3,2-dioxaborolan-2-yl)pyrimidin-2-yl]piperazin-1-carboxylate; and 4-(4-bromo-2-fluorophenyl)-1-methyl-1H-1,2,4-triazol-5(4H)-one (63.0 mg) prepared in Preparation 1.

Yield: 17.1%

$^1$H-NMR (CDCl$_3$) δ 8.57 (s, 2H), 8.21 (s, 2H), 7.75 (t, 1H), 7.55 (s, 1H), 7.60-7.30 (m, 2H), 5.04 (s, 1H), 4.73-4.55 (m, 3H), 3.56 (s, 3H), 3.41 (t, 1H), 3.31 (d, 1H), 3.15 (t, 1H), 2.49 (q, 2H), 1.27 (d, 3H), 1.21 (t, 3H)

Example 8

(S)-4-(2-fluoro-4-(2-(2-methyl-4-(5-(trifluoromethyl)pyridin-2-yl)piperazin-1-yl)pyrimidin-5-yl)phenyl)-1-methyl-1H-1,2,4-triazol-5(4H)-one The intermediate (760.0 mg) was prepared in accordance with the same procedures as in Steps 1 and 2 of Example 1, using (S)-3-methyl-1-(5-(trifluoromethyl)pyridin-2-yl)piperazine (1.0 g) instead of (S)-4-N—BOC-2-methylpiperazine. The titled compound was prepared in accordance with the same procedures as in Step 3 of Example 1, using the intermediate instead of (S)-tert-butyl 3-methyl-4-[5-(4,4,5,5-tetramethyl-1,3,2-dioxaborolan-2-yl)pyrimidin-2-yl]piperazin-1-carboxylate; and 4-(4-bromo-2-fluorophenyl)-1-methyl-1H-1,2,4-triazol-5(4H)-one (63.0 mg) prepared in Preparation 1.

Yield: 28.8%

$^1$H-NMR (CDCl$_3$) δ 8.58 (s, 2H), 8.42 (s, 1H), 7.76 (t, 1H), 7.72-7.58 (m, 2H), 7.50-7.30 (m, 2H), 6.66 (d, 1H), 5.01 (s, 1H), 4.62 (d, 1H), 4.36-4.20 (m, 2H), 3.70-3.45 (m, 5H), 3.30-3.15 (m, 1H), 1.29 (d, 3H)

Example 9

(S)-2-(4-(5-ethylpyrimidin-2-yl)-2-methylpiperazin-1-yl)-5-(3-fluoro-4-(1-methyl-5-oxo-1H-1,2,4-triazol-4(5H)-yl)phenyl)nicotinonitrile Step 1: (S)-tert-butyl 4-(5-bromo-3-cyanopyridin-2-yl)-3-methylpiperazin-1-carboxylate To a solution of 5-bromo-2-chloronicotinonitrile (10.0 g) in a mixed solvent of toluene (45.0 mL) and N,N-dimethylformamide (100.0 mL), was added potassium carbonate (13.0 g). The reaction mixture was stirred at room temperature for 10 minutes and then (S)-4-N—BOC-2-methylpiperazine (9.2 g) was added thereto. The reaction mixture was stirred at 100° C. for 12 hours, cooled to room temperature, and then concentrated under reduced pressure. Ethyl acetate (100.0 mL) and brine (100.0 mL) were added to the residue and then the organic layer was separated. Ethyl acetate (100.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=5/1) to give 3.8 g of the titled compound as a yellow oil (Yield: 72.5%).

$^1$H-NMR (CDCl$_3$) δ 8.34 (s, 1H), 7.84 (s, 1H), 4.60 (s, 1H), 4.25-3.80 (m, 3H), 3.38 (t, 1H), 3.26-2.95 (m, 2H), 1.48 (s, 9H), 1.26 (d, 3H)

Step 2: (S)-5-bromo-2-(2-methylpiperazin-1-yl) nicotinonitrile hydrochloride To a solution of (S)-tert-butyl 4-(5-bromo-3-cyanopyridin-2-yl)-3-methylpiperazin-1-carboxylate (3.8 g) prepared in Step 1 in ethyl acetate (200.0 mL), an aqueous solution of hydrochloric acid (2.0 M, 300.0 mL). The reaction mixture was stirred at room temperature for 12 hours, and then filtered. The resulting solid was washed with ethyl acetate and then dried in an oven to give 2.5 g of the titled compound as a white solid (Yield: 91.0%).

$^1$H-NMR (CDCl$_3$) δ 8.31 (s, 2H), 4.98 (s, 1H), 4.56 (d, 1H), 4.23-3.80 (m, 2H), 3.18 (t, 1H), 3.15-2.80 (m, 2H), 1.32 (s, 12H) 1.19 (d, 3H)

Step 3: (S)-5-bromo-2-(4-(5-ethylpyrimidin-2-yl)-2-methylpiperazin-1-yl)nicotinonitrile To a solution of (S)-5-bromo-2-(2-methylpiperazin-1-yl)nicotinonitrile hydrochloride (2.5 g) prepared in Step 2 in toluene (200.0 mL), were added sodium tert-butoxide (1.3 g), 2-chloro-5-ethylpyrimidine (1.2 mL), 4,5-bis(diphenylphosphino)-9,9-dimethylxanthene (316.0 mg) and tris(dibenzylideneacetone)dipalladium(0) (167.0 mg). The reaction mixture was stirred at 100° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=5/1) to give 3.1 g of the titled compound as a yellow solid (Yield: 86.7%).

$^1$H-NMR (CDCl$_3$) δ 8.35 (s, 1H), 8.19 (s, 2H), 7.84 (s, 1H), 4.75 (s, 1H), 4.61 (d, 1H), 4.49 (d, 1H), 4.21 (d, 1H), 3.52 (t, 1H), 3.39 (d, 1H), 3.24 (t, 1H), 2.49 (q, 2H), 1.30 (d, 3H), 1.20 (t, 3H)

Step 4: (S)-2-(4-(5-ethylpyrimidin-2-yl)-2-methylpiperazin-1-yl)-5-(4,4,5,5-tetramethyl-1,3,2-dioxaborolan-2-yl)nicotinonitrile To a solution of (S)-5-bromo-2-(4-(5-ethylpyrimidin-2-yl)-2-methylpiperazin-1-yl)nicotinonitrile (3.1 g) prepared in Step 3 in 1,4-dioxane (50.0 mL), were added potassium acetate (2.4 g), bis(pinacolato)diboron (2.6 g), 1,1'-bis(diphenylphosphino)ferrocene (133.1 mg) and [1,1'-bis(diphenylphosphino)ferrocene]dichloropalladium(II) (196.0 mg). The reaction mixture was stirred at 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=3/1) to give 1.9 g of the titled compound as a yellow solid (Yield: 54.8%).

$^1$H-NMR (CDCl$_3$) δ 8.62 (s, 1H), 8.19 (s, 2H), 8.15 (s, 1H), 4.93 (s, 1H), 4.61 (d, 1H), 4.51 (d, 1H), 4.42 (d, 1H), 3.54 (t, 1H), 3.37 (d, 1H), 3.23 (t, 1H), 2.48 (q, 2H), 1.33 (s, 12H), 1.30 (d, 3H), 1.20 (t, 3H)

Step 5: (S)-2-(4-(5-ethylpyrimidin-2-yl)-2-methylpiperazin-1-yl)-5-(3-fluoro-4-(1-methyl-5-oxo-1H-1,2,4-triazol-4(5H)-yl)phenyl)nicotinonitrile To a solution of (S)-2-(4-(5-ethylpyrimidin-2-yl)-2-methylpiperazin-1-yl)-5-(4,4,5,5-tetramethyl-1,3,2-dioxaborolan-2-yl)nicotinonitrile (100.0 mg) prepared in Step 4, 4-(4-bromo-2-fluorophenyl)-1-methyl-1H-1,2,4-triazol-5(4H)-one (62.6 mg) prepared in Preparation 1 and tetrakis(triphenylphosphine)palladium (13.3 mg) in N,N-dimethylformamide (3.0 mL), was added an aqueous solution of sodium carbonate (2.0 M, 0.5 mL). The reaction mixture was stirred at 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=1/2) to give 46.8 mg of the titled compound as a white solid (Yield: 40.9%).

$^1$H-NMR (CDCl$_3$) δ 8.77 (s, 1H), 8.57 (s, 1H), 8.41 (s, 1H), 8.05 (s, 1H), 7.70-7.64 (m, 3H), 4.25-4.39 (m, 3H), 3.97-3.87 (m, 3H), 3.31 (s, 3H), 2.66 (q, 2H), 1.42 (d, 3H), 1.26 (t, 3H)

Example 10

(S)-5-(4-(1-(2-(diethylamino)ethyl)-5-oxo-1H-1,2,4-triazol-4(5H)-yl)-3-fluorophenyl)-2-(4-(5-ethylpyrimidin-2-yl)-2-methylpiperazin-1-yl)nicotinonitrile The titled compound was prepared in accordance with the same procedures as in Step 5 of Example 9, using 4-(4-bromo-2-fluorophenyl)-1-[2-(diethylamino)ethyl]-1H-1,2,4-triazol-5(4H)-one (100.0 mg) prepared in Preparation 5 instead of 4-(4-bromo-2-fluorophenyl)-1-methyl-1H-1,2,4-triazol-5(4H)-one.

Yield: 9.5%

$^1$H-NMR (CDCl$_3$) δ 8.57 (s, 1H), 8.21 (s, 2H), 7.96 (s, 1H), 7.83 (t, 1H), 7.70 (s, 1H), 7.45-7.35 (m, 2H), 4.90 (s, 1H), 4.64 (d, 1H), 4.54 (d, 1H), 4.38 (d, 1H), 3.98 (t, 2H), 3.59 (t, 1H), 3.42 (d, 1H), 3.27 (t, 1H), 2.91 (t, 2H), 2.66 (q, 4H), 2.49 (q, 2H), 1.35 (d, 3H), 1.19 (t, 3H), 1.06 (t, 6H)

Example 11

(S)-2-(4-(5-ethylpyrimidin-2-yl)-2-methylpiperazin-1-yl)-5-(3-fluoro-4-(1-(2-hydroxy-2-methylpropyl)-5-oxo-1H-1,2,4-triazol-4(5H)-yl)phenyl)nicotinonitrile The titled compound was prepared in accordance with the same procedures as in Step 5 of Example 9, using 4-(4-bromo-2-fluorophenyl)-1-(2-hydroxy-2-methylpropyl)-1H-1,2,4-triazol-5(4H)-one (220.7 mg) prepared in Preparation 6 instead of 4-(4-bromo-2-fluorophenyl)-1-methyl-1H-1,2,4-triazol-5(4H)-one.

Yield: 22.4%

$^1$H-NMR (CDCl$_3$) δ 8.58 (s, 1H), 8.21 (s, 2H), 7.97 (s, 1H), 7.82 (t, 1H), 7.76 (s, 1H), 7.46-7.36 (m, 2H), 4.90 (s, 1H), 4.65 (d, 1H), 4.54 (d, 1H), 4.39 (d, 1H), 3.93 (s, 2H), 3.59 (t, 1H), 3.42 (d, 1H), 3.27 (t, 1H), 2.49 (q, 2H), 1.35 (d, 3H), 1.31 (s, 6H), 1.23 (t, 3H)

Example 12

(S)-2-(4-(5-ethylpyrimidin-2-yl)-2-methylpiperazin-1-yl)-5-(3-fluoro-4-(1-isobutyl-5-oxo-1H-1,2,4-triazol-4(5H)-yl)phenyl)nicotinonitrile The titled compound was prepared in accordance with the same procedures as in Step 5 of Example 9, using 4-(4- bromo-2-fluorophenyl)-1-isobutyl-1H-1,2,4-triazol-5(4H)-one (304.4 mg) prepared in Preparation 7 instead of 4-(4-bromo-2-fluorophenyl)-1-methyl-1H-1,2,4-triazol-5(4H)-one.

Yield: 28.9%

$^1$H-NMR (CDCl$_3$) δ 8.57 (s, 1H), 8.21 (s, 2H), 7.97 (s, 1H), 7.83 (t, 1H), 7.71 (s, 1H), 7.45-7.33 (m, 2H), 4.89 (s, 1H), 4.64 (d, 1H), 4.54 (d, 1H), 4.38 (d, 1H), 3.69 (d, 2H), 3.62 (t, 1H), 3.46 (d, 1H), 3.27 (t, 1H), 2.49 (q, 2H), 2.29-2.16 (m, 1H), 1.35 (d, 3H), 1.21 (t, 3H), 1.00 (d, 6H)

Example 13

(S)-methyl 2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)acetate The titled compound was prepared in accordance with the same procedures as in Step 5 of Example 9, using methyl 2-[4-(4-bromo-2-fluorophenyl)-5-oxo-4,5-dihydro-1H-1,2,4-triazol-1-yl]acetate (118.0 mg) prepared in Preparation 9 instead of 4-(4-bromo-2-fluorophenyl)-1-methyl-1H-1,2,4-triazol-5(4H)-one.

Yield: 24.4%

$^1$H-NMR (CDCl$_3$) δ 8.58 (s, 1H), 8.21 (s, 2H), 7.97 (s, 1H), 7.84 (t, 1H), 7.77 (s, 1H), 7.49-7.34 (m, 2H), 4.90 (s, 1H), 4.68 (s, 2H), 4.64 (d, 1H), 4.53 (d, 1H), 4.38 (d, 1H), 3.82 (s, 3H), 3.59 (t, 1H), 3.42 (d, 1H), 3.27 (t, 1H), 2.49 (q, 2H), 1.35 (d, 3H), 1.21 (t, 3H)

Example 14

(S)-2-(4-(5-ethylpyrimidin-2-yl)-2-methylpiperazin-1-yl)-5-(3-fluoro-4-(5-oxo-1-(2-pyrrolidin-1-yl)ethyl)-1H-1,2,4-triazol-4(5H)-yl)phenyl)nicotinonitrile The titled compound was prepared in accordance with the same procedures as in Step 5 of Example 9, using 4-(4-bromo-2-fluorophenyl)-1-[2-(pyrrolidin-1-yl)ethyl]-1H-1,2,4-triazol-5(4H)-one (60.0 mg) prepared in Preparation 10 instead of 4-(4-bromo-2-fluorophenyl)-1-methyl-1H-1,2,4-triazol-5(4H)-one.

Yield: 57.5%

$^1$H-NMR (CDCl$_3$) δ 8.57 (s, 1H), 8.21 (s, 2H), 7.96 (s, 1H), 7.84 (t, 1H), 7.71 (s, 1H), 7.44-7.33 (m, 2H), 4.89 (s, 1H), 4.65 (d, 1H), 4.54 (d, 1H), 4.38 (d, 1H), 4.03 (t, 2H), 3.59 (t, 1H), 3.42 (d, 1H), 3.27 (t, 1H), 2.93 (t, 2H), 2.62 (s, 4H), 2.49 (q, 2H), 1.80 (s, 4H), 1.36 (d, 3H), 1.23 (t, 3H)

Example 15

(S)-2-(4-(5-ethylpyrimidin-2-yl)-2-methylpiperazin-1-yl)-5-(3-fluoro-4-(1-(2-morpholinoethyl)-5-oxo-1H-1,2,4-triazol-4(5H)-yl)phenyl)nicotinonitrile The titled compound was prepared in accordance with the same procedures as in Step 5 of Example 9, using 4-(4-bromo-2-fluorophenyl)-1-(2-morpholinoethyl)-1H-1,2,4-triazol-5(4H)-one (171.1 mg) prepared in Preparation 11 instead of 4-(4-bromo-2-fluorophenyl)-1-methyl-1H-1,2,4-triazol-5(4H)-one.

Yield: 26.1%

$^1$H-NMR (CDCl$_3$) δ 8.57 (s, 1H), 8.21 (s, 2H), 7.97 (s, 1H), 7.81 (t, 1H), 7.71 (s, 1H), 7.46-7.33 (m, 2H), 4.90 (s, 1H), 4.65 (d, 1H), 4.54 (d, 1H), 4.38 (d, 1H), 4.02 (t, 2H), 3.70 (s, 4H), 3.59 (t, 1H), 3.42 (d, 1H), 3.28 (t, 1H), 2.78 (t, 2H), 2.56 (s, 4H), 2.49 (q, 2H), 1.36 (d, 3H), 1.23 (t, 3H)

Example 16

(S)-tert-butyl 2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethylcarbamate The titled compound was prepared in accordance with the same procedures as in Step 5 of Example 9, using tert-butyl 2-[4-(4-bromo-2-fluorophenyl)-5-oxo-4,5-dihydro-1H-1,2,4-triazol-1-yl]ethylcarbamate (100.0 mg) prepared in Preparation 13 instead of 4-(4-bromo-2-fluorophenyl)-1-methyl-1H-1,2,4-triazol-5(4H)-one.

Yield: 31.6%

$^1$H-NMR (CDCl$_3$) δ 8.78 (s, 2H), 7.80 (t, 1H), 7.68 (d, 1H), 7.39-7.33 (m, 2H), 4.99 (d, 2H), 3.99-3.96 (m, 1H), 3.86 (t, 2H), 3.31 (t, 4H), 3.00 (t, 2H), 2.71 (s, 3H), 1.97-1.83 (m, 8H), 1.76-1.70 (m, 2H), 0.98 (t, 3H)

Example 17

(S)-5-(4-(1-(2-aminoethyl)-5-oxo-1H-1,2,4-triazol-4(5H)-yl)-3-fluorophenyl)-2-(4-(5-ethylpyrimidin-2-yl)-2-methylpiperazin-1-yl)nicotinonitrile hydrochloride To a solution of (S)-tert-butyl 2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethylcarbamate (50.0 mg) prepared in Example 16 in ethyl acetate (5.0 mL), was added an aqueous solution of hydrochloric acid (2.0 M, 10.0 mL). The reaction mixture was stirred at room temperature for 12 hours and then filtered. The resulting solid was washed with ethyl acetate and then dried in an oven to give 38.3 mg of the titled compound as a white solid (Yield: 91.0%).

$^1$H-NMR (CDCl$_3$) δ 8.78 (s, 1H), 8.57 (s, 1H), 8.39 (s, 1H), 8.16 (s, 1H), 7.77-7.65 (m, 3H), 4.31-4.39 (m, 3H), 4.20-4.17 (m, 2H), 3.88-3.75 (m, 3H), 3.38 (t, 2H), 2.70 (q, 2H), 1.74 (t, 3H), 1.41 (d, 3H)

Example 18

(S)-5-(4-(1-(cyanomethyl)-5-oxo-1H-1,2,4-triazol-4(5H)-yl)-3-fluorophenyl)-2-(4-(5-ethylpyrimidin-2-yl)-2-methylpiperazin-1-yl)nicotinonitrile The titled compound was prepared in accordance with the same procedures as in Step 5 of Example 9, using 2-[4-(4-bromo-2-fluorophenyl)-5-oxo-4,5-dihydro-1H-1,2,4-triazol-1-yl]acetonitrile (102.5 mg) prepared in Preparation 14 instead of 4-(4-bromo-2-fluorophenyl)-1-methyl-1H-1,2,4-triazol-5(4H)-one.

Yield: 12.0%

$^1$H-NMR (CDCl$_3$) δ 8.58 (s, 1H), 8.21 (s, 2H), 7.97 (s, 1H), 7.86-7.75 (m, 2H), 7.47-7.35 (m, 2H), 4.90 (s, 1H), 4.65 (d, 1H), 4.59 (s, 2H), 4.54 (d, 1H), 4.39 (d, 1H), 3.59 (t, 1H), 3.42 (d, 1H), 3.27 (t, 1H), 2.49 (q, 2H), 1.36 (d, 3H), 1.21 (t, 3H)

Example 19

(S)-tert-butyl 2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethyl(isopropyl)carbamate The titled compound was prepared in accordance with the same procedures as in Step 5 of Example 9, using tert-butyl 2-[4-(4-bromo-2-fluorophenyl)-5-oxo-4,5-dihydro-1H-1,2,4-triazol-1-yl]ethyl(isopropyl)carbamate (50.0 mg) prepared in Preparation 12 instead of 4-(4-bromo-2-fluorophenyl)-1-methyl-1H-1,2,4-triazol-5(4H)-one.
Yield: 18.8%
$^1$H-NMR (CDCl$_3$) δ 8.57 (d, 1H), 8.21 (s, 2H), 7.96 (d, 1H), 7.80 (t, 1H), 7.69 (s, 1H), 7.39 (t, 2H), 4.90 (m, 1H), 4.66 (d, 1H), 4.55 (d, 1H), 4.38 (d, 1H), 4.23 (m, 2H), 3.75 (t, 1H), 3.59 (t, 1H), 3.43 (d, 2H), 3.32-3.22 (m, 2H), 2.50 (q, 2H), 1.52 (m, 9H), 1.36 (d, 3H), 1.21 (t, 3H), 1.15 (d, 6H)

Example 20

(S)-2-(4-(5-ethylpyrimidin-2-yl)-2-methylpiperazin-1-yl)-5-(3-fluoro-4-(1-(2-(isopropylamino)ethyl)-5-oxo-1H-1,2,4-triazol-4(5H)-yl)phenyl)nicotinonitrile hydrochloride To a solution of (S)-tert-butyl 2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethyl(isopropyl)carbamate (50.0 mg) prepared in Example 19 in ethyl acetate (5.0 mL), was added an aqueous solution of hydrochloric acid (2.0 M, 10.0 mL). The reaction mixture was stirred at room temperature for 12 hours and then filtered. The resulting solid was washed with ethyl acetate and then dried in an oven to give 40.6 mg of the titled compound as a white solid (Yield: 95.9%).
$^1$H-NMR (MeOD) δ 8.78 (d, 1H), 8.55 (s, 2H), 8.37 (d, 1H), 8.17 (d, 1H), 7.77-7.72 (m, 2H), 7.66 (d, 1H), 4.39 (m, 3H), 4.23 (t, 2H), 3.90-3.69 (m, 3H), 3.50 (t, 2H), 3.41 (m, 1H), 2.68 (q, 2H), 1.40 (d, 3H), 1.37 (d, 6H), 1.28 (t, 3H)

Example 21

(S)-2-(4-(5-ethylpyrimidin-2-yl)-2-methylpiperazin-1-yl)-5-(3-fluoro-4-(5-oxo-1H-1,2,4-triazol-4(5H)-yl)phenyl)nicotinonitrile The intermediate (55.0 mg) was prepared in accordance with the same procedures as in Step 5 of Example 9, using 4-(4-bromo-2-fluorophenyl)-1-trityl-1H-1,2,4-triazol-5(4H)-one (120.4 mg) prepared in Preparation 15 instead of 4-(4-bromo-2-fluorophenyl)-1-methyl-1H-1,2,4-triazol-5(4H)-one. To a solution of the intermediate in dichloromethane (3.0 mL), was added trifluoroacetic acid (30.0 μL). The reaction mixture was stirred at room temperature for 12 hours and then concentrated under reduced pressure to give a colorless oily residue. The residue was purified with silica gel column chromatography (dichloromethane/methanol=20/1) to give 16.4 mg of the titled compound as a white solid (Yield: 42.5%).
$^1$H-NMR (CDCl$_3$) δ 9.48 (s, 1H), 8.58 (s, 1H), 8.21 (s, 2H), 7.97 (s, 1H), 7.81 (t, 1H), 7.73 (s, 1H), 7.48-7.35 (m, 2H), 4.90 (s, 1H), 4.65 (d, 1H), 4.54 (d, 1H), 4.39 (d, 1H), 3.60 (t, 1H), 3.42 (d, 1H), 3.28 (t, 1H), 2.49 (q, 2H), 1.36 (d, 3H), 1.23 (t, 3H)

Example 22

(S)-2-(4-(5-ethylpyrimidin-2-yl)-2-methylpiperazin-1-yl)-5-(3-fluoro-4-(1-(methoxymethyl)-5-oxo-1H-1,2,4-triazol-4(5H)-yl)phenyl)nicotinonitrile The titled compound was prepared in accordance with the same procedures as in Step 5 of Example 9, using 4-(4-bromo-2-fluorophenyl)-1-(methoxymethyl)-1H-1,2,4-triazol-5(4H)-one (50.0 mg) prepared in Preparation 19 instead of 4-(4-bromo-2-fluorophenyl)-1-methyl-1H-1,2,4-triazol-5(4H)-one.
Yield: 46.0%
$^1$H-NMR (CDCl$_3$) δ 8.58 (s, 1H), 8.21 (s, 2H), 7.97 (s, 1H), 7.81 (t, 1H), 7.75 (s, 1H), 7.50-7.35 (m, 2H), 5.22 (s, 2H), 4.90 (s, 1H), 4.65 (d, 1H), 4.55 (d, 1H), 4.40-4.36 (m, 1H), 3.59 (t, 1H), 3.49 (s, 3H), 3.42 (d, 1H), 3.27 (t, 1H), 2.47 (q, 2H), 1.36 (d, 3H), 1.21 (t, 3H)

Example 23

(S)—N-(2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethyl)methanesulfonamide The titled compound was prepared in accordance with the same procedures as in Step 5 of Example 9, using N{2-[4-(4-bromo-2-fluorophenyl)-5-oxo-4,5-dihydro-1H-1,2,4-triazol-1-yl]ethyl}methanesulfonamide (50.0 mg) prepared in Preparation 16 instead of 4-(4-bromo-2-fluorophenyl)-1-methyl-1H-1,2,4-triazol-5(4H)-one.
Yield: 54.0%
$^1$H-NMR (CDCl$_3$) δ 8.57 (d, 1H), 8.21 (s, 2H), 7.97 (d, 1H), 7.78 (t, 1H), 7.73 (d, 1H), 7.41 (t, 2H), 5.17 (t, 1H), 4.90 (m, 1H), 4.65 (d, 1H), 4.54 (d, 1H), 4.39 (d, 1H), 4.09 (m, 1H), 3.63-3.56 (m, 3H), 3.41 (dd, 1H), 3.28 (dd, 1H), 2.98 (s, 3H), 2.49 (q, 2H), 1.36 (d, 3H), 1.21 (t, 3H)

Example 24

(S)-ethyl 4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-carboxylate The titled compound was prepared in accordance with the same procedures as in Step 5 of Example 9, using ethyl 4-(4-bromo-2-fluorophenyl)-5-oxo-4,5-dihydro-1H-1,2,4-triazol-1-carboxylate (200.0 mg) prepared in Preparation 20 instead of 4-(4-bromo-2-fluorophenyl)-1-methyl-1H-1,2,4-triazol-5(4H)-one.
Yield: 14.6%
$^1$H-NMR (CDCl$_3$) δ 8.58 (s, 1H), 8.21 (s, 2H), 7.98 (s, 1H), 7.81 (s, 1H), 7.75 (t, 1H), 7.48-7.37 (m, 2H), 4.91 (s, 1H), 4.65 (d, 1H), 4.60-4.50 (m, 3H), 4.40 (d, 1H), 3.59 (t, 1H), 3.42 (d, 1H), 3.27 (t, 1H), 2.49 (q, 2H), 1.48 (t, 3H), 1.36 (d, 3H), 1.20 (t, 3H)

Example 25

(S)-5-(4-(1-(2-cyano-2-methylpropyl)-5-oxo-1H-1,2,4-triazol-4(5H)-yl)-3-fluorophenyl)-2-(4-(5-ethylpyrimidin-2-yl)-2-methylpiperazin-1-yl)nicotinonitrile The titled compound was prepared in accordance with the same procedures as in Step 5 of Example 9, using 3-[4-(4- bromo-2-fluorophenyl)-5-oxo-4,5-dihydro-1H-1,2,4-triazol-1-yl]-2,2-dimethyl propanenitrile (50.0 mg) prepared in Preparation 21 instead of 4-(4-bromo-2-fluorophenyl)-1-methyl-1H-1,2,4-triazol-5(4H)-one.

Yield: 20.7%

$^1$H-NMR (CDCl$_3$) δ 8.58 (d, 1H), 8.21 (s, 2H), 7.97 (d, 1H), 7.83 (t, 1H), 7.74 (d, 1H), 7.38 (m, 2H), 4.90 (m, 1H), 4.63 (d, 1H), 4.55 (m, 1H), 4.38 (d, 1H), 4.15 (s, 2H), 3.59 (m, 1H), 3.43 (m, 1H), 3.27 (m, 1H), 2.49 (q, 2H), 1.70 (s, 6H), 1.35 (d, 3H), 1.21 (t, 3H)

Example 26

(S)—N-(2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethyl)acetamide The titled compound was prepared in accordance with the same procedures as in Step 5 of Example 9, using N{2-[4-(4-bromo-2-fluorophenyl)-5-oxo-4,5-dihydro-1H-1,2,4-triazol-1-yl]ethyl}acetamide (50.0 mg) prepared in Preparation 28 instead of 4-(4-bromo-2-fluorophenyl)-1-methyl-1H-1,2,4-triazol-5(4H)-one.

Yield: 18.2%

$^1$H-NMR (CDCl$_3$) δ 8.57 (d, 1H), 8.21 (s, 2H), 7.96 (d, 1H), 7.75 (t, 1H), 7.70 (d, 1H), 7.39 (t, 2H), 4.90 (m, 1H), 4.65 (d, 1H), 4.54 (d, 1H), 4.39 (d, 1H), 4.14-4.08 (m, 4H), 3.59 (dt, 1H), 3.41 (dd, 1H), 3.28 (dt, 1H), 2.49 (q, 2H), 2.41 (s, 6H), 1.36 (d, 3H), 1.21 (t, 3H)

Example 27

(S)-2-(4-(5-ethylpyrimidin-2-yl)-2-methylpiperazin-1-yl)-5-(3-fluoro-4-(1-((4-methylpiperazin-1-yl)methyl)-5-oxo-1H-1,2,4-triazol-4(5H)-yl)phenyl)nicotinonitrile The titled compound was prepared in accordance with the same procedures as in Step 5 of Example 9, using 4-(4-bromo-2-fluorophenyl)-1-[(4-methylpiperazin-1-yl)methyl]-1H-1,2,4-triazol-5(4H)-one (80.0 mg) prepared in Preparation 31 instead of 4-(4-bromo-2-fluorophenyl)-1-methyl-1H-1,2,4-triazol-5(4H)-one.

Yield: 39.4%

$^1$H-NMR (CDCl$_3$) δ 8.58 (s, 1H), 8.21 (s, 2H), 7.98 (s, 1H), 7.79 (t, 1H), 7.70 (s, 1H), 7.46-7.34 (m, 2H), 4.89 (s, 1H), 4.79 (s, 2H), 4.65 (d, 1H), 4.54 (d, 1H), 4.38 (d, 1H), 3.59 (t, 1H), 3.41 (d, 1H), 3.27 (t, 1H), 2.82 (s, 4H), 2.64-2.32 (m, 6H), 2.29 (s, 3H), 1.36 (d, 3H), 1.21 (t, 3H)

Example 28

(S)-2-(4-(5-ethylpyrimidin-2-yl)-2-methylpiperazin-1-yl)-5-(3-fluoro-4-(5-oxo-1-(pyrrolidin-1-ylmethyl)-1H-1,2,4-triazol-4(5H)-yl)phenyl)nicotinonitrile The titled compound was prepared in accordance with the same procedures as in Step 5 of Example 9, using 4-(4-bromo-2-fluorophenyl)-1-(pyrrolidin-1-ylmethyl)-1H-1,2,4-triazol-5(4H)-one (80.0 mg) prepared in Preparation 33 instead of 4-(4-bromo-2-fluorophenyl)-1-methyl-1H-1,2,4-triazol-5(4H)-one.

Yield: 52.4%

$^1$H-NMR (CDCl$_3$) δ 8.58 (s, 1H), 8.21 (s, 2H), 7.98 (s, 1H), 7.84 (t, 1H), 7.74 (s, 1H), 7.48-7.34 (m, 2H), 4.89 (s, 1H), 4.86 (s, 2H), 4.65 (d, 1H), 4.54 (d, 1H), 4.38 (d, 1H), 3.59 (t, 1H), 3.41 (d, 1H), 3.27 (t, 1H), 2.84 (s, 4H), 2.49 (q, 2H), 1.79 (s, 4H), 1.36 (d, 3H), 1.21 (t, 3H)

Example 29

(S)-5-(2,5-difluoro-4-(1-methyl-5-oxo-1H-1,2,4-triazol-4(5H)-yl)phenyl)-2-(4-(5-ethyl pyrimidin-2-yl)-2-methylpiperazin-1-yl)nicotinonitrile The titled compound was prepared in accordance with the same procedures as in Step 5 of Example 9, using 4-(4-bromo-2,5-difluorophenyl)-1-methyl-1H-1,2,4-triazol-5(4H)-one (29.1 mg) prepared in Preparation 25 instead of 4-(4-bromo-2-fluorophenyl)-1-methyl-1H-1,2,4-triazol-5(4H)-one.

Yield: 35.8%

$^1$H-NMR (CDCl$_3$) δ 8.53 (d, 1H), 8.21 (s, 2H), 7.98 (t, 1H), 7.76 (m, 2H), 7.28 (m, 1H), 4.93 (m, 1H), 4.64 (m, 1H), 4.55 (m, 1H), 4.42 (m, 1H), 3.62 (m, 1H), 3.56 (s, 3H), 3.40 (m, 1H), 3.27 (m, 1H), 2.49 (q, 2H), 1.36 (d, 3H), 1.21 (t, 3H)

Example 30

2-(4-(5-ethylpyrimidin-2-yl)piperazin-1-yl)-5-(3-fluoro-4-(1-isopropyl-5-oxo-1H-1,2,4-triazol-4(5H)-yl)phenyl)nicotinonitrile

Step 1: tert-butyl 4-(5-ethylpyrimidin-2-yl)piperazin-1-carboxylate

To a solution of 1-BOC piperazine (5.0 g) in N,N-dimethylformamide (100.0 mL), was added cesium carbonate (17.5 g). The reaction mixture was stirred at room temperature for 10 minutes and then 2-chloro-5-ethylpyrimidine (3.2 mL) was added thereto. The reaction mixture was stirred at 100° C. for 12 hours, cooled to room temperature, and then concentrated under reduced pressure. Ethyl acetate (50.0 mL) and brine (50.0 mL) were added to the residue and then the organic layer was separated. Ethyl acetate (50.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=3/1) to give 6.0 g of the titled compound as a colorless oil (Yield: 76.4%).

$^1$H-NMR (CDCl$_3$) δ 8.18 (s, 2H), 3.76 (s, 4H), 3.49 (s, 4H), 2.47 (q, 2H), 1.49 (s, 9H), 1.19 (t, 3H)

Step 2: 5-ethyl-2-(piperazin-1-yl)pyrimidine hydrochloride

To a solution of tert-butyl 4-(5-ethylpyrimidin-2-yl)piperazin-1-carboxylate (6.0 g) prepared in Step 1 in ethyl acetate (60.0 mL), was an aqueous solution of hydrochloric acid (4.0 M, 30.0 mL). The reaction mixture was stirred at room temperature for 12 hours and then filtered. The resulting solid was washed with ethyl acetate and then dried in an oven to give 3.9 g of the titled compound as a white solid (Yield: 99.0%).

$^1$H-NMR (MeOD) δ 8.18 (s, 2H), 3.76 (s, 4H), 3.49 (s, 4H), 2.47 (q, 2H), 1.19 (t, 3H)

Step 3: 5-bromo-2-(4-(5-ethylpyrimidin-2-yl)piperazin-1-yl)nicotinonitrile

To a solution of 5-ethyl-2-(piperazin-1-yl)pyrimidine hydrochloride (3.9 g) prepared in Step 2 in a mixed solvent of toluene (25.0 mL) and N,N-dimethylformamide (50.0 mL), was added potassium carbonate (8.4 g). The reaction mixture was stirred at room temperature for 10 minutes and then 5-bromo-2-chloronicotinonitrile (4.4 g) was added thereto. The reaction mixture was stirred at 100° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=5/1) to give 4.5 g of the titled compound as a white solid (Yield: 60.0%).

$^1$H-NMR (CDCl$_3$) δ 8.36 (s, 1H), 8.21 (s, 2H), 7.86 (s, 1H), 3.94 (s, 4H), 3.81 (s, 4H), 2.49 (q, 2H), 1.20 (t, 3H)

Step 4: 2-(4-(5-ethylpyrimidin-2-yl)piperazin-1-yl)-5-(4,4,5,5-tetramethyl-1,3,2-dioxaborolan-2-yl)nicotinonitrile To a solution of 5-bromo-2-(4-(5-ethylpyrimidin-2-yl)piperazin-1-yl)nicotinonitrile (4.5 g) prepared in Step 3 in 1,4-dioxane (50.0 mL), were added potassium acetate (3.6 g), bis(pinacolato)diboron (4.0 g), 1,1'-bis(diphenylphosphino)ferrocene (201.2 mg) and [1,1'-bis(diphenylphosphino)ferrocene]dichloropalladium(II) (296.4 mg). The reaction mixture was stirred at 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=3/1) to give 3.1 g of the titled compound as a white solid (Yield: 61.4%).

$^1$H-NMR (CDCl$_3$) δ 8.63 (s, 1H), 8.21 (s, 2H), 8.16 (s, 1H), 3.93 (s, 8H), 2.49 (q, 2H), 1.33 (s, 12H), 1.20 (t, 3H)

Step 5: 2-(4-(5-ethylpyrimidin-2-yl)piperazin-1-yl)-5-(3-fluoro-4-(1-isopropyl-5-oxo-1H-1,2,4-triazol-4(5H)-yl)phenyl)nicotinonitrile To a solution of 2-(4-(5-ethylpyrimidin-2-yl)piperazin-1-yl)-5-(4,4,5,5-tetramethyl-1,3,2-dioxaborolan-2-yl)nicotinonitrile (23.1 mg) prepared in Step 4, 4-(4-bromo-2-fluorophenyl)-1-isopropyl-1H-1,2,4-triazol-5(4H)-one (21.5 mg) prepared in Preparation 3 and tetrakis(triphenylphosphine)palladium(0) (3.6 mg) in N,N-dimethylformamide (1.5 mL), was added an aqueous solution of sodium carbonate (2.0 M, 0.5 mL). The reaction mixture was stirred at 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=1/1) to give 10.5 mg of the titled compound as a white solid (Yield: 39.2%).

$^1$H-NMR (CDCl$_3$) δ 8.58 (s, 1H), 8.22 (s, 2H), 7.98 (s, 1H), 7.83 (t, 1H), 7.70 (s, 1H), 7.45-7.34 (m, 2H), 4.59-4.53 (m, 1H), 3.97 (s, 4H), 3.93 (s, 4H), 2.50 (q, 2H), 1.44 (d, 6H), 1.21 (t, 3H)

Example 31

5-(4-(1-(2-methoxyethyl)-5-oxo-1H-1,2,4-triazol-4(5H)-yl)-3-fluorophenyl)-2-(4-(5-ethylpyrimidin-2-yl)piperazin-1-yl)nicotinonitrile The titled compound was prepared in accordance with the same procedures as in Step 5 of Example 30, using 4-(4-bromo-2-fluorophenyl)-1-(2-methoxyethyl)-1H-1,2,4-triazol-5(4H)-one (78.6 mg) prepared in Preparation 4 instead of 4-(4-bromo-2-fluorophenyl)-1-isopropyl-1H-1,2,4-triazol-5(4H)-one.

Yield: 19.2%

$^1$H-NMR (CDCl$_3$) δ 8.58 (s, 1H), 8.22 (s, 2H), 7.97 (s, 1H), 7.84 (t, 1H), 7.72 (s, 1H), 7.45-7.33 (m, 2H), 4.06 (t, 2H), 3.97 (s, 4H), 3.94 (s, 4H), 3.81 (t, 2H), 3.57 (q, 2H), 2.50 (q, 2H), 1.27-1.19 (m, 6H)

Example 32

2-(4-(5-ethylpyrimidin-2-yl)piperazin-1-yl)-5-(3-fluoro-4-(1-neopentyl-5-oxo-1H-1,2,4-triazol-4(5H)-yl)phenyl)nicotinonitrile The titled compound was prepared in accordance with the same procedures as in Step 5 of Example 30, using 4-(4-bromo-2-fluorophenyl)-1-neopentyl-1H-1,2,4-triazol-5(4H)-one (78.6 mg) prepared in Preparation 8 instead of 4-(4-bromo-2-fluorophenyl)-1-isopropyl-1H-1,2,4-triazol-5(4H)-one.

Yield: 23.3%

$^1$H-NMR (CDCl$_3$) δ 8.58 (s, 1H), 8.22 (s, 2H), 7.98 (s, 1H), 7.84 (t, 1H), 7.71 (s, 1H), 7.44-7.32 (m, 2H), 3.97 (s, 4H), 3.93 (s, 4H), 2.50 (q, 2H), 1.21 (t, 3H), 1.05 (s, 9H)

Example 33

(R)-2-(4-(5-ethylpyrimidin-2-yl)piperazin-1-yl)-5-(3-fluoro-4-(5-oxo-1-(tetrahydrofuran-3-yl)-1H-1,2,4-triazol-4(5H)-yl)phenyl)nicotinonitrile The titled compound was prepared in accordance with the same procedures as in Step 5 of Example 30, using (R)-4-(4-bromo-2-fluorophenyl)-1-(tetrahydrofuran-3-yl)-1H-1,2,4-triazol-5(4H)-one (78.6 mg) prepared in Preparation 32 instead of 4-(4-bromo-2-fluorophenyl)-1-isopropyl-1H-1,2,4-triazol-5(4H)-one.

Yield: 27.9%

$^1$H-NMR (CDCl$_3$) δ 8.58 (s, 1H), 8.22 (s, 2H), 7.98 (s, 1H), 7.80 (t, 1H), 7.70 (s, 1H), 7.46-7.34 (m, 2H), 5.10-4.90 (m, 1H), 4.16-4.02 (m, 2H), 4.02-3.75 (m, 10H), 2.50 (q, 2H), 2.43-2.28 (m, 2H), 1.21 (t, 3H)

Example 34

(R)-2-(4-(5-ethylpyrimidin-2-yl)piperazin-1-yl)-5-(3-fluoro-4-(5-oxo-1-(pyrrolidin-3-yl)-1H-1,2,4-triazol-4(5H)-yl)phenyl)nicotinonitrile The intermediate (13.7 mg) was prepared in accordance with the same procedures as in Step 5 of Example 30, using (R)-tert-butyl 3-[4-(4-bromo-2-fluorophenyl)-5-oxo-4,5-dihydro-1H-1,2,4-triazol-1-yl]pyrrolidin-1-carboxylate prepared in Preparation 18 instead of 4-(4-bromo-2-fluorophenyl)-1-isopropyl-1H-1,2,4-triazol-5(4H)-one. To a solution of the intermediate in ethyl acetate (1.0 mL), was added an aqueous solution of hydrochloric acid (2.0 M, 2.0 mL). The reaction mixture was stirred at room temperature for 12 hours and then filtered. The resulting solid was washed with ethyl acetate and then dried in an oven to give 5.8 mg of the titled compound as a yellow solid (Yield: 55.0%).
¹H-NMR (CDCl₃) δ 8.58 (s, 1H), 8.22 (s, 2H), 7.98 (s, 1H), 7.80 (t, 1H), 7.70 (s, 1H), 7.45-7.34 (m, 2H), 4.93-4.89 (m, 1H), 3.97 (s, 4H), 3.94 (s, 4H), 3.81-3.49 (m, 4H), 2.50 (q, 2H), 2.36-2.29 (m, 2H), 1.21 (t, 3H)

Example 35

2-(4-(5-ethylpyrimidin-2-yl)piperazin-1-yl)-5-(3-fluoro-4-(1-(morpholinomethyl)-5-oxo-1H-1,2,4-triazol-4(5H)-yl)phenyl)nicotinonitrile The titled compound was prepared in accordance with the same procedures as in Step 5 of Example 30, using 4-(4-bromo-2-fluorophenyl)-1-(morpholinomethyl)-1H-1,2,4-triazol-5(4H)-one (80.0 mg) prepared in Preparation 22 instead of 4-(4-bromo-2-fluorophenyl)-1-isopropyl-1H-1,2,4-triazol-5(4H)-one.
Yield: 82.3%
¹H-NMR (CDCl₃) δ 8.58 (s, 1H), 8.21 (s, 2H), 7.97 (s, 1H), 7.81 (t, 1H), 7.71 (s, 1H), 7.47-7.35 (m, 2H), 4.90 (s, 1H), 4.75 (s, 2H), 4.65 (d, 1H), 4.54 (d, 1H), 4.39 (d, 1H), 3.73 (s, 4H), 3.59 (t, 1H), 3.42 (d, 1H), 3.27 (t, 1H), 2.77 (s, 4H), 2.49 (q, 2H), 1.36 (d, 3H), 1.21 (t, 3H)

Example 36

(S)-5-(4-(1-(2,3-dihydroxypropyl)-5-oxo-1H-1,2,4-triazol-4(5H)-yl)-3-fluorophenyl)-2-(4-(5-ethylpyrimidin-2-yl)piperazin-1-yl)nicotinonitrile The intermediate (45.5 mg) was prepared in accordance with the same procedures as in Step 5 of Example 30, using (S)-4-(4-bromo-2-fluorophenyl)-1-[(2,2-dimethyl-1,3-dioxolane-4-yl)methyl]-1H-1,2,4-triazol-5(4H)-one prepared in Preparation 23 instead of 4-(4-bromo-2-fluorophenyl)-1-isopropyl-1H-1,2,4-triazol-5(4H)-one. To a solution of the intermediate in tetrahydrofuran (2.0 mL), was added an aqueous solution of hydrochloric acid (3.0 N, 2.0 mL). The reaction mixture was stirred at room temperature for 12 hours, neutralized to pH 8 with 10% sodium hydroxide solution, and then extracted with ethyl acetate two times. The resulting extract was washed with brine, dried over anhydrous sodium sulfate, and then concentrated under reduced pressure to give 39.1 mg of the titled compound as a white solid (Yield: 90.0%).
¹H-NMR (CDCl₃) δ 8.58 (s, 1H), 8.22 (s, 2H), 7.98 (s, 1H), 7.80 (t, 1H), 7.75 (s, 1H), 7.45-7.34 (m, 2H), 4.15-4.04 (m, 2H), 3.97 (s, 4H), 3.94 (s, 4H), 3.74-3.56 (m, 2H), 2.50 (q, 2H), 1.21 (t, 3H)

Example 37

2-(4-(5-ethylpyrimidin-2-yl)piperazin-1-yl)-5-(3-fluoro-4-(5-oxo-1-(2-oxo-2-(pyrrolidin-1-yl)ethyl)-1H-1,2,4-triazol-4(5H)-yl)phenyl)nicotinonitrile The titled compound was prepared in accordance with the same procedures as in Step 5 of Example 30, using 4-(4-bromo-2-fluorophenyl)-1-[2-oxo-2-(pyrrolidin-1-yl)ethyl]-1H-1,2,4-triazol-5(4H)-one (39.1 mg) prepared in Preparation 24 instead of 4-(4-bromo-2-fluorophenyl)-1-isopropyl-1H-1,2,4-triazol-5(4H)-one.
Yield: 48.8%
¹H-NMR (CDCl₃) δ 8.58 (s, 1H), 8.22 (s, 2H), 7.99 (s, 1H), 7.87 (t, 1H), 7.77 (s, 1H), 7.42-7.36 (m, 2H), 4.64 (s, 2H), 3.98 (s, 4H), 3.93 (s, 4H), 3.56-3.49 (m, 4H), 3.48-3.40 (m, 2H), 2.50 (q, 2H), 2.00-1.83 (m, 2H), 1.21 (t, 3H)

Example 38

2-(4-(5-ethylpyrimidin-2-yl)piperazin-1-yl)-5-(2-fluoro-4-(1-isopropyl-5-oxo-1H-1,2,4-triazol-4(5H)-yl)phenyl)nicotinonitrile The titled compound was prepared in accordance with the same procedures as in Step 5 of Example 30, using 4-(4-bromo-3-fluorophenyl)-1-isopropyl-1H-1,2,4-triazol-5(4H)-one (35.7 mg) prepared in Preparation 26 instead of 4-(4-bromo-2-fluorophenyl)-1-isopropyl-1H-1,2,4-triazol-5(4H)-one.
Yield: 42.7%
¹H-NMR (CDCl₃) δ 8.54 (s, 1H), 8.21 (s, 2H), 8.00 (s, 1H), 7.74 (s, 1H), 7.57 (m, 1H), 7.48 (m, 2H), 4.58 (m, 1H), 3.93 (m, 8H), 2.49 (m, 2H), 1.43 (d, 6H), 1.22 (t, 3H)

Example 39

2-(4-(5-ethylpyrimidin-2-yl)piperazin-1-yl)-5-(4-(1-methyl-5-oxo-1H-1,2,4-triazol-4(5H)-yl)phenyl)nicotinonitrile The titled compound was prepared in accordance with the same procedures as in Step 5 of Example 30, using 4-(4-bromophenyl)-1-methyl-1H-1,2,4-triazol-5(4H)-one (60.0 mg) prepared in Preparation 27 instead of 4-(4-bromo-2-fluorophenyl)-1-isopropyl-1H-1,2,4-triazol-5(4H)-one.
Yield: 38.5%
¹H-NMR (CDCl₃) δ 8.60 (s, 1H), 8.22 (s, 2H), 8.00 (s, 1H), 7.73 (s, 1H), 7.67 (dd, 2H), 7.61 (dd, 2H), 3.98 (s, 4H), 3.90 (s, 4H), 3.56 (s, 3H), 2.50 (q, 2H), 1.21 (t, 3H)

Example 40

2-(4-(5-ethylpyrimidin-2-yl)piperazin-1-yl)-5-(4-(1-(2-methoxyethyl)-5-oxo-1H-1,2,4-triazol-4(5H)-yl)phenyl)nicotinonitrile The titled compound was prepared in accordance with the same procedures as in Step 5 of Example 30, using 4-(4-bromophenyl)-1-(2-methoxyethyl)-1H-1,2,4-triazol-5(4H)-one (60.0 mg) prepared in Preparation 29 instead of 4-(4-bromo-2-fluorophenyl)-1-isopropyl-1H-1,2,4-triazol-5(4H)-one.
Yield: 38.5%
¹H-NMR (CDCl₃) δ 8.60 (s, 1H), 8.22 (s, 2H), 8.00 (s, 1H), 7.75 (s, 1H), 7.69 (dd, 2H), 7.60 (dd, 2H), 4.08 (t, 2H), 3.98 (s, 4H), 3.91 (s, 4H), 3.77 (t, 2H), 3.41 (s, 3H), 2.50 (q, 2H), 1.21 (t, 3H)

Example 41

(R)-2-(4-(5-ethylpyrimidin-2-yl)piperazin-1-yl)-5-(4-(5-oxo-1-(tetrahydrofuran-3-yl)-1H-1,2,4-triazol-4(5H)-yl)phenyl)nicotinonitrile The titled compound was prepared in accordance with the same procedures as in Step 5 of Example 30, using (R)-4-(4-bromophenyl)-1-(tetrahydrofuran-3-yl)-1H-1,2,4-triazol- 5(4H)-one (60.0 mg) prepared in Preparation 30 instead of 4-(4-bromo-2-fluorophenyl)-1-isopropyl-1H-1,2,4-triazol-5 (4H)-one.

Yield: 47.2%

$^1$H-NMR (CDCl$_3$) δ 8.60 (s, 1H), 8.22 (s, 2H), 8.02 (s, 1H), 7.75 (s, 1H), 7.67 (dd, 2H), 7.61 (dd, 2H), 5.05-4.95 (m, 1H), 4.18-4.13 (m, 2H), 4.11-4.06 (m, 2H), 4.03 (s, 4H), 3.98 (s, 4H), 2.48 (q, 2H), 2.40-2.34 (m, 2H), 1.21 (t, 3H)

Example 42

(S)-2-(4-(5-ethylpyrimidin-2-yl)piperazin-1-yl)-5-(4-(5-oxo-1-(pyrrolidin-3-yl)-1H-1,2,4-triazol-4(5H)-yl)phenyl)nicotinonitrile The intermediate (50.0 mg) was prepared in accordance with the same procedures as in Step 5 of Example 30, using (S)-tert-butyl 3-[4-(4-bromophenyl)-5-oxo-4,5-dihydro-1H-1,2,4-triazol-1-yl]pyrrolidin-1-carboxylate prepared in Preparation 37 instead of 4-(4-bromo-2-fluorophenyl)-1-isopropyl-1H-1,2,4-triazol-5(4H)-one. To a solution of the intermediate in ethyl acetate (5.0 mL), was added an aqueous solution of hydrochloric acid (2.0 M, 10.0 mL). The reaction mixture was stirred at room temperature for 12 hours and then filtered. The resulting solid was washed with ethyl acetate and then dried in an oven to give 31.1 mg of the titled compound as a white solid (Yield: 75.0%).

$^1$H-NMR (CDCl$_3$) δ 8.50 (s, 1H), 8.22 (s, 2H), 8.00 (s, 1H), 7.73 (s, 1H), 7.67 (dd, 2H), 7.61 (dd, 2H), 4.93-4.88 (m, 1H), 3.98 (s, 4H), 3.91 (s, 4H), 3.81-3.75 (m, 1H), 3.73-3.55 (m, 2H), 3.55-3.40 (m, 1H), 2.50 (q, 2H), 2.40-2.22 (m, 2H), 1.21 (t, 3H)

Example 43

2-(4-(5-ethylpyrimidin-2-yl)piperazin-1-yl)-5-(3-fluoro-4-(1-isopropyl-5-oxo-1H-1,2,4-triazol-4(5H)-yl)phenyl)nicotinonitrile hydrochloride To a solution of 2-(4-(5-ethylpyrimidin-2-yl)piperazin-1-yl)-5-(3-fluoro-4-(1-isopropyl-5-oxo-1H-1,2,4-triazol-4(5H)-yl)phenyl)nicotinonitrile (10.5 mg) prepared in Example 30 in ethyl acetate (1.0 mL), was added an aqueous solution of hydrochloric acid (2.0 M, 2.0 mL). The reaction mixture was stirred at room temperature for 1 hour, and then filtered. The resulting solid was washed with ethyl acetate and then dried in an oven to give 9.8 mg of the titled compound as a yellow solid (Yield: 95.0%).

$^1$H-NMR (CDCl$_3$) δ 8.58 (s, 1H), 8.22 (s, 2H), 7.98 (s, 1H), 7.83 (t, 1H), 7.70 (s, 1H), 7.45-7.34 (m, 2H), 4.59-4.53 (m, 1H), 3.97 (s, 4H), 3.93 (s, 4H), 2.50 (q, 2H), 1.44 (d, 6H), 1.21 (t, 3H)

Example 44

2-(4-(5-ethylpyrimidin-2-yl)piperazin-1-yl)-5-(3-fluoro-4-(1-isopropyl-5-oxo-1H-1,2,4-triazol-4(5H)-yl)phenyl)nicotinonitrile sulfonate To a solution of 2-(4-(5-ethylpyrimidin-2-yl)piperazin-1-yl)-5-(3-fluoro-4-(1-isopropyl-5-oxo-1H-1,2,4-triazol-4(5H)-yl)phenyl)nicotinonitrile (10.5 mg) prepared in Example 30 in ethyl acetate (1.0 mL), was added methanesulfonic acid (2.0 mL). The reaction mixture was stirred at room temperature for 1 hour and then filtered. The resulting solid was washed with ethyl acetate and then dried in an oven to give 10.2 mg of the titled compound as a yellow solid (Yield: 100.0%).

$^1$H-NMR (CDCl$_3$) δ 8.58 (s, 1H), 8.22 (s, 2H), 7.98 (s, 1H), 7.83 (t, 1H), 7.70 (s, 1H), 7.45-7.34 (m, 2H), 4.59-4.53 (m, 1H), 3.97 (s, 4H), 3.93 (s, 4H), 2.50 (q, 2H), 1.44 (d, 6H), 1.21 (t, 3H)

Example 45

5-(3-fluoro-4-(1-methyl-5-oxo-1H-1,2,4-triazol-4(5H)-yl)phenyl)-2-(4-(5-isopropyl-1, 2,4-oxadiazol-3-yl)piperazin-1-yl)nicotinonitrile Step 1: tert-butyl 4-cyanopiperazin-1-carboxylate A solution of 1-BOC-piperazine (30.0 g) in a mixed solvent of dichloromethane (1.0 L) and distilled water (18.0 mL) was cooled to 0° C. and then a solution of cyanogen bromide (3.0 M, 64.4 mL) and sodium hydrogen carbonate (27.1 g) were added thereto. The reaction mixture was stirred at room temperature for 12 hours and then concentrated under reduced pressure. Ethyl acetate (500.0 mL) and brine (500.0 mL) were added to the residue and then the organic layer was separated. Ethyl acetate (500.0 mL) was added to the water layer and then the organic layer was separated. The combined organic layer was dried over anhydrous sodium sulfate and then concentrated under reduced pressure to give 31.6 g of the titled compound as a white solid (Yield: 92.8%).

$^1$H-NMR (CDCl$_3$) δ 3.52 (t, 4H), 3.20 (t, 4H), 1.46 (s, 9H)

Step 2: (E)-tert-butyl 4-(N'-hydroxycarbamimidoyl)piperazin-1-carboxylate

To a solution of tert-butyl 4-cyanopiperazin-1-carboxylate (31.6 g) prepared in Step 1 in ethanol (1.0 L), were added triethylamine (23.8 mL) and hydroxyamine hydrochloride (11.8 g). The reaction mixture was stirred at, 80° C. for 12 hours and then concentrated under reduced pressure to give 34.8 g of the titled compound as a white solid (Yield: 95.2%).

$^1$H-NMR (CDCl$_3$) δ 3.52 (t, 4H), 3.20 (t, 4H), 1.46 (s, 9H)

Step 3: tert-butyl 4-(5-isopropyl-1,2,4-oxadiazol-3-yl)piperazin-1-carboxylate

A solution of (E)-tert-butyl 4-(N'-hydroxycarbamimidoyl)piperazin-1-carboxylate (34.8 g) prepared in Step 2 and triethylamine (22.4 mL) in toluene (1.0 L) was cooled to 0° C. and then isobutyryl chloride (16.9 mL) was slowly added. The reaction mixture was refluxed at 130° C. for 6 hours, cooled to room temperature, and then concentrated under reduced pressure. Ethyl acetate (500.0 mL) and brine (500.0 mL) were added to the residue and then the organic layer was separated. Ethyl acetate (500.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=5/1) to give 17.1 g of the titled compound as a white solid (Yield: 40.5%).

$^1$H-NMR (CDCl$_3$) δ 8.36 (s, 1H), 8.21 (s, 2H), 7.86 (s, 1H), 3.94 (s, 4H), 3.81 (s, 4H), 2.49 (q, 2H), 1.20 (t, 3H)

Step 4: 5-isopropyl-3-(piperazin-1-yl)-1,2,4-oxadiazole

To a solution of tert-butyl 4-(5-isopropyl-1,2,4-oxadiazol-3-yl)piperazin-1-carboxylate (17.1 g) prepared in Step 3 in ethyl acetate (200.0 mL), was added an aqueous solution of hydrochloric acid (4.0 M, 150.0 mL). The reaction mixture was stirred at room temperature for 6 hours and then concentrated under reduced pressure. Ethyl acetate (100.0 mL) and brine (100.0 mL) were added to the residue and then the organic layer was separated. Ethyl acetate (100.0 mL) was added to the water layer and then the organic layer was separated. The combined organic layer was dried over anhydrous sodium sulfate and then concentrated under reduced pressure to give 9.8 g of the titled compound as a white solid (Yield: 86.7%).

$^1$H-NMR (MeOD) δ 8.18 (s, 2H), 3.76 (s, 4H), 3.49 (s, 4H), 2.47 (q, 2H), 1.19 (t, 3H)

Step 5: 5-bromo-2-(4-(5-isopropyl-1,2,4-oxadiazol-3-yl)piperazin-1-yl)nicotinonitrile To a solution of 5-isopropyl-3-(piperazin-1-yl)-1,2,4-oxadiazole (3.1 g) prepared in Step 4 in a mixed solvent of toluene (25.0 mL) and N,N-dimethylformamide (50.0 mL), was added potassium carbonate (4.4 g). The reaction mixture was stirred at room temperature for 10 minutes and then 5-bromo-2-chloronicotinonitrile (3.5 g) was added thereto. The reaction mixture was stirred at 100° C. for 5 hours, cooled to room temperature, and then concentrated under reduced pressure. Ethyl acetate (25.0 mL) and brine (25.0 mL) were added to the residue and then the organic layer was separated. Ethyl acetate (25.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=5/1) to give 5.9 g of the titled compound as a white solid (Yield: 98.0%).

$^1$H-NMR (CDCl$_3$) δ 8.37 (s, 1H), 7.87 (s, 1H), 3.79 (t, 4H), 3.61 (t, 4H), 3.13-3.05 (m, 1H), 1.36 (d, 6H)

Step 6: 2-(4-(5-isopropyl-1,2,4-oxadiazol-3-yl)piperazin-1-yl)-5-(4,4,5,5-tetramethyl-1,3,2-dioxaborolan-2-yl)nicotinonitrile To a solution of 5-bromo-2-(4-(5-isopropyl-1,2,4-oxadiazol-3-yl)piperazin-1-yl)nicotinonitrile (5.9 g) prepared in Step 5 in 1,4-dioxane (50.0 mL), were added potassium acetate (4.6 g), bis(pinacolato)diboron (5.1 g), 1,1'-bis(diphenylphosphino)ferrocene (259.5 mg) and [1,1'-bis(diphenylphosphino)ferrocene]dichloropalladium(II) (382.2 mg). The reaction mixture was stirred at 110° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=3/1) to give 4.2 g of the titled compound as a white solid (Yield: 63.1%).

$^1$H-NMR (CDCl$_3$) δ 8.64 (s, 1H), 8.16 (s, 1H), 3.91 (t, 4H), 3.60 (t, 4H), 3.13-3.05 (m, 1H), 1.36 (d, 6H), 1.33 (s, 12H)

Step 7: 5-(3-fluoro-4-(1-methyl-5-oxo-1H-1,2,4-triazol-4(5H)-yl)phenyl)-2-(4-(5-isopropyl-1, 2,4-oxadiazol-3-yl)piperazin-1-yl)nicotinonitrile To a solution of 2-(4-(5-isopropyl-1,2,4-oxadiazol-3-yl)piperazin-1-yl)-5-(4,4,5,5-tetramethyl-1,3,2-dioxaborolan-2-yl)nicotinonitrile (100.0 mg) prepared in Step 6, 4-(4-bromo-2-fluorophenyl)-1-methyl-1H-1,2,4-triazol-5(4H)-one (64.2 mg) prepared in Preparation 1 and tetrakis(triphenylphosphine)palladium(0) (13.9 mg) in N,N-dimethylformamide (5.0 mL), was added an aqueous solution of sodium carbonate (2.0 M, 0.5 mL). The reaction mixture was stirred at 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=1/2) to give 37.4 mg of the titled compound as a white solid (Yield: 32.2%).

$^1$H-NMR (CDCl$_3$) δ 8.58 (d, 1H), 7.98 (d, 1H), 7.83 (t, 1H), 7.70 (m, 1H), 7.40 (m, 2H), 3.92 (m, 4H), 3.65 (m, 4H), 3.56 (s, 3H), 3.10 (m, 1H), 1.37 (d, 6H)

Example 46

5-(3-fluoro-4-(1-isopropyl-5-oxo-1H-1,2,4-triazol-4 (5H)-yl)phenyl)-2-(4-(5-isopropyl-1,2,4-oxadiazol-3-yl)piperazin-1-yl)nicotinonitrile The titled compound was prepared in accordance with the same procedures as in Step 7 of Example 45, using 4-(4-bromo-2-fluorophenyl)-1-isopropyl-1H-1,2,4-triazol-5 (4H)-one (70.8 mg) prepared in Preparation 3 instead of 4-(4-bromo-2-fluorophenyl)-1-methyl-1H-1,2,4-triazol-5 (4H)-one.

Yield: 61.8%

$^1$H-NMR (CDCl$_3$) δ 8.58 (d, 1H), 7.99 (d, 1H), 7.85 (t, 1H), 7.70 (m, 1H), 7.40 (m, 2H), 4.57 (m, 1H), 3.91 (m, 4H), 3.65 (m, 4H), 3.10 (m, 1H), 1.43 (d, 6H), 1.37 (d, 6H)

Example 47

(S)-5-(3-fluoro-4-(5-oxo-1-(tetrahydrofuran-3-yl)-1H-1,2,4-triazol-4(5H)-yl)phenyl)-2-(4-(5-isopropyl-1,2,4-oxadiazol-3-yl)piperazin-1-yl)nicotinonitrile The titled compound was prepared in accordance with the same procedures as in Step 7 of Example 45, using (S)-4-(4-bromo-2-fluorophenyl)-1-(tetrahydrofuran-3-yl)-1H-1,2,4-triazol-5(4H)-one (77.4 mg) prepared in Preparation 17 instead of 4-(4-bromo-2-fluorophenyl)-1-methyl-1H-1,2,4-triazol-5(4H)-one.

Yield: 20.4%

$^1$H-NMR (CDCl$_3$) δ 8.58 (s, 1H), 7.98 (s, 1H), 7.81 (t, 1H), 7.71 (s, 1H), 7.44-7.33 (m, 2H), 5.05-4.93 (m, 1H), 4.18-4.06 (m, 2H), 4.03-3.94 (m, 2H), 3.91 (s, 4H), 3.64 (s, 4H), 3.14-3.06 (m, 1H), 2.42-2.34 (m, 2H), 1.37 (d, 6H)

Example 48

2-(4-(5-isopropyl-1,2,4-oxadiazol-3-yl)piperazin-1-yl)-5-(4-(1-(methoxymethyl)-5-oxo-1H-1,2,4-triazol-4(5H)-yl)phenyl)nicotinonitrile The titled compound was prepared in accordance with the same procedures as in Step 7 of Example 45, using 4-(4- bromophenyl)-1-(methoxymethyl)-1H-1,2,4-triazol-5(4H)-one (90.4 mg) prepared in Preparation 35 instead of 4-(4-bromo-2-fluorophenyl)-1-methyl-1H-1,2,4-triazol-5(4H)-one.

Yield: 38.7%

$^1$H-NMR (CDCl$_3$) δ 8.58 (s, 1H), 8.01 (s, 1H), 7.80 (s, 1H), 7.67 (dd, 2H), 7.62 (dd, 2H), 5.22 (s, 2H), 3.88 (s, 4H), 3.66 (s, 4H), 3.49 (s, 3H), 3.14-3.03 (m, 1H), 1.37 (d, 6H)

Example 49

5-(3-fluoro-4-(5-oxo-1-propyl-1H-1,2,4-triazol-4(5H)-yl)phenyl)-2-(4-(5-isopropyl-1,2,4-oxadiazol-3-yl)piperazin-1-yl)nicotinonitrile hydrochloride The intermediate (50.0 mg) was prepared in accordance with the same procedures as in Step 7 of Example 45, using 4-(4-bromo-2-fluorophenyl)-1-propyl-1H-1,2,4-triazol-5(4H)-one prepared in Preparation 2 instead of 4-(4-bromo-2-fluorophenyl)-1-methyl-1H-1,2,4-triazol-5(4H)-one. To a solution of the intermediate in ethyl acetate (5.0 mL), was added an aqueous solution of hydrochloric acid (4.0 M, 10.0 mL). The reaction mixture was stirred at room temperature for 2 hours and then filtered. The resulting solid was washed with ethyl acetate and then dried in an oven to give 40.2 mg of the titled compound as a yellow solid (Yield: 82.5%).

$^1$H-NMR (CDCl$_3$) δ 8.58 (s, 1H), 7.98 (s, 1H), 7.85 (t, 1H), 7.70 (s, 1H), 7.42-7.36 (m, 2H), 3.91 (s, 4H), 3.85 (t, 2H), 3.65 (s, 4H), 3.12-3.08 (m, 1H), 1.84 (q, 2H), 1.37 (d, 6H), 1.01 (t, 3H)

Example 50 tert-butyl 4-(5-(3-fluoro-4-(5-oxo-1-propyl-1H-1,2,4-triazol-4(5H)-yl)phenyl)pyridin-2-yl)-3-(tri fluoromethyl)piperazin-1-carboxylate Step 1: tert-butyl 3-(trifluoromethyl)piperazin-1-carboxylate A solution obtained by diluting di-tert-butyl dicarbonate (8.8 mL) with dichloromethane (30.0 mL) was slowly added to a solution of 2-(trifluoromethyl)piperazine (6.0 g) in dichloromethane (120.0 mL). The reaction mixture was stirred at 40° C. for 1 hour and then concentrated under reduced pressure. Ethyl acetate (50.0 mL) and brine (50.0 mL) were added to the residue and then the organic layer was separated. Ethyl acetate (50.0 mL) was added to the water layer and then the organic layer was separated. The combined organic layer was dried over anhydrous sodium sulfate and then concentrated under reduced pressure to give 7.1 g of the titled compound as a yellow oil (Yield: 28.0%).

$^1$H-NMR (CDCl$_3$) δ 5.30 (s, 1H), 4.48 (d, 1H), 4.27 (d, 1H), 3.71 (d, 1H), 3.38 (t, 1H), 3.26 (d, 1H), 3.24-2.77 (m, 1H), 1.48 (s, 9H)

Step 2: tert-butyl 4-(5-bromopyridin-2-yl)-3-(trifluoromethyl)piperazin-1-carboxylate To a solution of tert-butyl 3-(trifluoromethyl)piperazin-1-carboxylate (3.3 g) prepared in Step 1 in toluene (100.0 mL), were added sodium tert-butoxide (1.9 g), 2,5-dibromopyridine (3.1 g), 4,5-bis(diphenylphosphino)-9,9-dimethylxanthene (451.0 mg) and tris(dibenzylideneacetone)dipalladium(0) (238.0 mg). The reaction mixture was stirred at 100° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=5/1) to give 2.4 g of the titled compound as a yellow oil (Yield: 45.0%).

$^1$H-NMR (CDCl$_3$) δ 8.20 (s, 1H), 7.60 (d, 1H), 6.55 (d, 1H), 5.30 (s, 1H), 4.48 (d, 1H), 4.27 (d, 1H), 3.71 (d, 1H), 3.38 (t, 1H), 3.26 (d, 1H), 3.24-2.77 (m, 1H), 1.48 (s, 9H)

Step 3: tert-butyl 4-(5-(4,4,5,5-tetramethyl-1,3,2-dioxaborolan-2-yl)pyridin-2-yl)-3-(trifluoromethyl)piperazin-1-carboxylate To a solution of tert-butyl 4-(5-bromopyridin-2-yl)-3-(trifluoromethyl)piperazin-1-carboxylate (1.0 g) prepared in Step 2 in 1,4-dioxane (20.0 mL), were added potassium acetate (714.3 mg), bis(pinacolato)diboron (677.7 mg), 2-dicyclohexylphophino-2',4',6'-triisopropylbiphenyl (69.4 mg) and tris(dibenzylideneacetone)dipalladium(0) (66.6 mg). The reaction mixture was 100° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=3/1) to give 969.0 mg of the titled compound as a yellow solid (Yield: 87.4%).

$^1$H-NMR (CDCl$_3$) δ 8.54 (s, 1H), 7.89 (d, 1H), 6.61 (d, 1H), 5.52 (s, 1H), 4.48 (d, 1H), 4.27 (d, 1H), 3.84 (d, 1H), 3.40 (t, 1H), 3.25 (d, 1H), 3.23-2.92 (m, 1H), 1.48 (s, 9H), 1.32 (s, 12H)

Step 4: tert-butyl 4-(5-(3-fluoro-4-(5-oxo-1-propyl-1H-1,2,4-triazol-4(5H)-yl)phenyl)pyridin-2-yl)-3-(trifluoromethyl)piperazin-1-carboxylate To a solution of tert-butyl 4-(5-(4,4,5,5-tetramethyl-1,3,2-dioxaborolan-2-yl)pyridin-2-yl)-3-(trifluoromethyl)piperazin-1-carboxylate (81.9 mg) prepared in Step 3, 4-(4-bromo-2-fluorophenyl)-1-propyl-1H-1,2,4-triazol-5(4H)-one (53.8 mg) prepared in Preparation 2 and tetrakis(triphenylphosphine)palladium(0) (10.4 mg) in N,N-dimethylformamide (3.0 mL), was added an aqueous solution of sodium carbonate (2.0 M, 0.5 mL). The reaction mixture was stirred at 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=1/2) to give 32.6 mg of the titled compound as a white solid (Yield: 33.3%).

$^1$H-NMR (CDCl$_3$) δ 8.43 (s, 1H), 7.80-7.72 (m, 2H), 7.69 (s, 1H), 7.47-7.34 (m, 2H), 6.74 (d, 1H), 5.45 (s, 1H), 4.52 (d, 1H), 4.35-3.90 (m, 2H), 3.84 (t, 2H), 3.45 (t, 1H), 3.29 (d, 1H), 3.20-2.90 (m, 1H), 1.90-1.80 (m, 2H), 1.49 (s, 9H), 1.00 (t, 3H)

Example 51 tert-butyl 4-(5-(3-fluoro-4-(1-isopropyl-5-oxo-1H-1,2,4-triazol-4(5H)-yl)phenyl)pyridin-2-yl)-3-(trifluoromethyl)piperazin-1-carboxylate The titled compound was prepared in accordance with the same procedures as in Step 4 of Example 50, using 4-(4- bromo-2-fluorophenyl)-1-isopropyl-1H-1,2,4-triazol-5 (4H)-one (45.3 mg) prepared in Preparation 3 instead of 4-(4-bromo-2-fluorophenyl)-1-methyl-1H-1,2,4-triazol-5 (4H)-one.

Yield: 44.0%

$^1$H-NMR (CDCl$_3$) δ 8.43 (s, 1H), 7.82-7.72 (m, 2H), 7.68 (s, 1H), 7.47-7.33 (m, 2H), 6.74 (d, 1H), 5.45 (s, 1H), 4.62-4.55 (m, 1H), 4.52 (d, 1H), 4.35-3.80 (m, 2H), 3.45 (t, 1H), 3.29 (d, 1H), 3.17-2.85 (m, 1H), 1.49 (s, 9H), 1.44 (d, 6H)

Example 52

4-(2-fluoro-4-(6-(2-(trifluoromethyl)-4-(5-(trifluoromethyl)pyridin-2-yl)piperazin-1-yl)pyridin-3-yl)phenyl)-1-propyl-1H-1,2,4-triazol-5(4H)-one The intermediate (650.0 mg) was prepared in accordance with the same procedures as in Steps 2 and 3 of Example 50, using 3-(trifluoromethyl)-1-(5-(trifluoromethyl)pyridin-2-yl)piperazine (1.0 g) instead of tert-butyl 3-(trifluoromethyl)piperazin-1-carboxylate. The titled compound was prepared in accordance with the same procedures as in Step 4 of Example 50, using the intermediate instead of tert-butyl 4-(5-(4,4,5,5-tetramethyl-1,3,2-dioxaborolan-2-yl)pyridin-2-yl)-3-(trifluoromethyl)piperazin-1-carboxylate; and 4-(4-bromo-2-fluorophenyl)-1-propyl-1H-1,2,4-triazol-5(4H)-one (40.0 mg) prepared in Preparation 2.

Yield: 7.5%

$^1$H-NMR (CDCl$_3$) δ 8.45 (s, 1H), 8.43 (s, 1H), 7.77 (t, 2H), 7.69 (s, 2H), 7.41 (t, 2H), 6.81 (d, 1H), 6.65 (d, 1H), 5.41 (bs, 1H), 4.60 (d, 1H), 4.15 (t, 1H), 3.84 (3H), 3.67 (t, 1H), 3.48-3.27 (m, 2H), 1.85 (q, 2H), 1.00 (t, 3H)

Example 53

4-(4-(6-(4-(5-ethylpyrimidin-2-yl)-2-(trifluoromethyl)piperazin-1-yl)pyridin-3-yl)-2-fluorophenyl)-1-propyl-1H-1,2,4-triazol-5(4H)-one The intermediate (720.0 mg) was prepared in accordance with the same procedures as in Steps 2 and 3 of Example 50, using 5-ethyl-2-(3-(trifluoromethyl)piperazin-1-yl)pyrimidine (1.0 g) instead of tert-butyl 3-(trifluoromethyl)piperazin-1-carboxylate. The titled compound was prepared in accordance with the same procedures as in Step 4 of Example 50, using the intermediate instead of tert-butyl 4-(5-(4,4,5,5-tetramethyl-1,3,2-dioxaborolan-2-yl)pyridin-2-yl)-3-(trifluoromethyl)piperazin-1-carboxylate; and 4-(4-bromo-2-fluorophenyl)-1-propyl-1H-1,2,4-triazol-5(4H)-one (40.0 mg) prepared in Preparation 2.

Yield: 26.3%

$^1$H-NMR (CDCl$_3$) δ 8.45 (t, 1H), 8.22 (s, 1H), 7.76 (d, 2H), 7.69 (s, 1H), 7.41 (t, 2H), 7.17 (d, 2H), 5.50 (bs, 1H), 5.08 (d, 1H), 4.67 (d, 1H), 4.05 (t, 1H), 3.84 (t, 2H), 3.54 (m, 2H), 3.25 (t, 1H), 2.49 (q, 2H), 1.86 (q, 2H), 1.21 (t, 3H), 1.00 (t, 3H)

Example 54 tert-butyl 1-(5-(3-fluoro-4-(5-oxo-1-propyl-1H-1,2,4-triazol-4(5H)-yl)phenyl)pyrimidin-2-yl)piperidin-4-yl(methyl)carbamate Step 1: tert-butyl 1-(5-bromopyrimidin-2-yl)piperidin-4-ylcarbamate To a solution of 5-bromo-2-chloropyrimidine (10.3 g) in N,N-dimethylformamide (150.0 mL), was added cesium carbonate (26.1 g). The reaction mixture was stirred at room temperature for 10 minutes and then 4-(N—BOC-amino)piperidine (10.7 g) was added thereto. The reaction mixture was stirred at 100° C. for 12 hours, cooled to room temperature, and then concentrated under reduced pressure. Ethyl acetate (100.0 mL) and brine (100.0 mL) were added to the residue and then the organic layer was separated. Ethyl acetate (100.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=5/1) to give 5.2 g of the titled compound as a white solid (Yield: 27.4%).

$^1$H-NMR (CDCl$_3$) δ 8.30 (s, 2H), 4.80 (s, 1H), 4.39 (d, 1H), 4.15-4.11 (m, 2H), 3.17 (t, 1H), 3.17-2.90 (m, 2H), 1.49 (s, 9H), 1.18 (d, 3H)

Step 2: tert-butyl 1-(5-bromopyrimidin-2-yl)piperidin-4-yl(methyl)carbamate

To a solution of tert-butyl 1-(5-bromopyrimidin-2-yl)piperidin-4-ylcarbamate (5.2 g) prepared in Step 1 in tetrahydrofuran (100.0 mL), was added sodium hydride (1.4 g). The reaction mixture was stirred at room temperature for 30 minutes and then iodomethane (2.7 g) was added thereto. The reaction mixture was stirred at room temperature for 12 hours, and then concentrated under reduced pressure. Ethyl acetate (50.0 mL) and brine (50.0 mL) were added to the residue and then the organic layer was separated. Ethyl acetate (50.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=5/1) to give 4.8 g of the titled compound as a white solid (Yield: 88.6%).

$^1$H-NMR (CDCl$_3$) δ 7.64-7.61 (m, 2H), 7.44-7.41 (m, 2H), 3.93 (t, 2H), 2.85 (t, 2H), 2.60 (q, 4H), 1.03 (t, 6H)

Step 3: tert-butyl methyl(1-(5-(4,4,5,5-tetramethyl-1,3,2-dioxaborolan-2-yl)pyrimidin-2-yl)piperidin-4-yl)carbamate To a solution of tert-butyl 1-(5-bromopyrimidin-2-yl)piperidin-4-yl(methyl)carbamate (1.5 g) prepared in Step 2 in 1,4-dioxane (100.0 mL), were added potassium acetate (1.2 g), bis(pinacolato)diboron (1.2 g), 2-dicyclohexylphosphino-2',4',6'-triisopropylbiphenyl (120.0 mg) and tris(dibenzylideneacetone)dipalladium(0) (110.0 mg). The reaction mixture was stirred at 100° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=3/1) to give 1.0 g of the titled compound as a white solid (Yield: 58.7%).

$^1$H-NMR (CDCl$_3$) δ 8.35 (s, 1H), 7.85 (s, 1H), 4.36 (t, 1H), 4.32 (t, 1H), 3.32-3.19 (m, 3H), 3.11-3.04 (m, 1H), 2.24-2.19 (m, 2H), 2.10-2.02 (m, 2H), 1.33 (d, 6H), 1.32 (s, 12H)

Step 4: tert-butyl 1-(5-(3-fluoro-4-(5-oxo-1-propyl-1H-1,2,4-triazol-4(5H)-yl)phenyl)pyrimidin-2-yl)piperidin-4-yl(methyl)carbamate To a solution of tert-butyl methyl(1-(5-(4,4,5,5-tetramethyl-1,3,2-dioxaborolan-2-yl)pyrimidin-2-yl)piperidin-4- yl)carbamate (1.0 g) prepared in Step 3, 4-(4-bromo-2-fluorophenyl)-1-propyl-1H-1,2,4-triazol-5(4H)-one (720.0 mg) prepared in Preparation 2 and tetrakis(triphenylphosphine)palladium(0) (140.0 mg) in N,N-dimethylformamide (50.0 mL), was added an aqueous solution of sodium carbonate (2.0 M, 10.0 mL). The reaction mixture was stirred at, 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=1/2) to give 345.0 mg of the titled compound as a white solid (Yield: 28.0%).

$^1$H-NMR (CDCl$_3$) δ 8.53 (s, 2H), 7.78 (t, 1H), 7.67 (s, 1H), 7.38 (t, 2H), 4.95 (d, 2H), 3.84 (t, 2H), 2.96 (t, 2H), 2.72 (s, 3H), 1.88-1.82 (m, 4H), 1.81-1.76 (m, 2H), 1.48 (s, 9H), 1.00 (t, 3H)

Example 55

N-(1-(5-(3-fluoro-4-(5-oxo-1-propyl-1H-1,2,4-triazol-4(5H)-yl)phenyl)pyrimidin-2-yl)piperidin-4-yl)-N-methylpropan-1-sulfonamide To a solution of tert-butyl 1-(5-(3-fluoro-4-(5-oxo-1-propyl-1H-1,2,4-triazol-4(5H)-yl)phenyl)pyrimidin-2-yl)piperidin-4-yl(methyl)carbamate (50.0 mg) prepared in Example 54 in ethyl acetate (10.0 mL), was added an aqueous solution of hydrochloric acid (2.0 M, 30.0 mL). The reaction mixture was stirred at room temperature for 1 hour and then concentrated under reduced pressure to give 48.8 mg of the intermediate. To a solution of the intermediate in dichloromethane (10.0 mL), were added triethylamine (50.0 µL) and 1-propanesulfonyl chloride (30.0 µL) at 0° C. The reaction mixture was stirred at room temperature for 4 hours and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=1/2) to give 14.8 mg of the titled compound as a white solid (Yield: 21.2%).

$^1$H-NMR (CDCl$_3$) δ 8.54 (s, 2H), 7.78 (t, 1H), 7.69 (d, 1H), 7.39-7.33 (m, 2H), 4.99 (d, 2H), 4.02-3.96 (m, 1H), 3.84 (t, 2H), 3.01-2.93 (m, 4H), 2.79 (s, 3H), 1.88-1.74 (m, 8H), 1.09 (t, 3H), 0.99 (t, 3H)

Example 56 tert-butyl ethyl(1-(5-(3-fluoro-4-(5-oxo-1-propyl-1H-1,2,4-triazol-4(5H)-yl)phenyl)pyrimidin-2-yl)piperidin-4-yl)carbamate The intermediate (500.0 mg) was prepared in accordance with the same procedures as in Steps 2 and 3 of Example 54, using tert-butyl 1-(5-bromopyrimidin-2-yl)piperidin-4-yl-carbamate (1.0 g) Prepared in Step 1 of Example 54; and iodoethane (50.0 mL) instead of iodomethane. The titled compound was prepared in accordance with the same procedures as in Step 4 of Example 54, using the intermediate instead of tert-butyl methyl(1-(5-(4,4,5,5-tetramethyl-1,3,2-dioxaborolan-2-yl)pyrimidin-2-yl)piperidin-4-yl)carbamate; and 4-(4-bromo-2-fluorophenyl)-1-propyl-1H-1,2,4-triazol-5(4H)-one (50.0 mg) prepared in Preparation 2.

Yield: 16.2%

$^1$H-NMR (CDCl$_3$) δ 8.53 (s, 2H), 7.77 (t, 1H), 7.68 (d, 1H), 7.36 (m, 2H), 4.94 (d, 2H), 3.84 (t, 2H), 3.12 (s, 2H), 2.95 (t, 2H), 1.88-1.80 (m, 4H), 1.70 (m, 2H), 1.54-1.48 (m, 9H), 1.10 (t, 3H)

Example 57 tert-butyl 1-(3-fluoro-5-(3-fluoro-4-(5-oxo-1-propyl-1H-1,2,4-triazol-4(5H)-yl)phenyl)pyridin-2-yl)piperidin-4-yl(methyl)carbamate The intermediate (5.0 g) was prepared in accordance with the same procedures as in Steps 1 to 3 of Example 54, using 5-bromo-2,3-difluoropyridine (10.0 g) instead of 5-bromo-2-chloropyrimidine. The titled compound was prepared in accordance with the same procedures as in Step 4 of Example 54, using the intermediate instead of tert-butyl methyl(1-(5-(4,4,5,5-tetramethyl-1,3,2-dioxaborolan-2-yl)pyrimidin-2-yl)piperidin-4-yl)carbamate; and 4-(4-bromo-2-fluorophenyl)-1-propyl-1H-1,2,4-triazol-5(4H)-one (50.0 mg) prepared in Preparation 2.

Yield: 40.5%

$^1$H-NMR (CDCl$_3$) δ 8.24 (d, 1H), 7.78 (t, 1H), 7.69 (d, 1H), 7.42 (m, 3H), 4.29 (d, 2H), 3.84 (t, 2H), 2.98 (t, 2H), 2.76 (s, 3H), 1.80 (m, 4H), 1.48 (s, 9H), 1.00 (t, 3H)

Example 58 tert-butyl 1-(3-cyano-5-(3-fluoro-4-(1-isopropyl-5-oxo-1H-1,2,4-triazol-4(5H)-yl)phenyl)pyridin-2-yl)piperidin-4-yl(methyl)carbamate The intermediate (5.0 g) was prepared in accordance with the same procedures as in Steps 1 to 3 of Example 54, using 5-bromo-2-chloronicotinonitrile (10.0 g) instead of 5-bromo-2-chloropyrimidine. The titled compound was prepared in accordance with the same procedures as in Step 4 of Example 54, using the intermediate instead of tert-butyl methyl(1-(5-(4,4,5,5-tetramethyl-1,3,2-dioxaborolan-2-yl)pyrimidin-2-yl)piperidin-4-yl)carbamate; and 4-(4-bromo-2-fluorophenyl)-1-isopropyl-1H-1,2,4-triazol-5(4H)-one (50.0 mg) prepared in Preparation 3 instead of 4-(4-bromo-2-fluorophenyl)-1-propyl-1H-1,2,4-triazol-5(4H)-one.

Yield: 6.1%

$^1$H-NMR (CDCl$_3$) δ 8.55 (s, 1H), 7.94 (s, 1H), 7.83 (t, 1H), 7.69 (s, 1H), 7.38 (t, 2H), 4.62-4.56 (m, 3H), 3.10 (m, 2H), 2.76 (s, 3H), 1.82 (s, 4H), 1.49 (s, 9H), 1.44 (d, 6H)

Example 59 prop-1-en-2-yl 1-(3-cyano-5-(3-fluoro-4-(1-isopropyl-5-oxo-1H-1,2,4-triazol-4(5H)-yl)phenyl)pyridin-2-yl)piperidin-4-yl(methyl)carbamate To a solution of tert-butyl 1-(3-cyano-5-(3-fluoro-4-(1-isopropyl-5-oxo-1H-1,2,4-triazol-4(5H)-yl)phenyl)pyridin-2-yl)piperidin-4-yl(methyl)carbamate (60.0 mg) prepared in Example 58 in ethyl acetate (10.0 mL), was added an aqueous solution of hydrochloric acid (2.0 M, 30.0 mL). The reaction mixture was stirred at room temperature for 1 hour and then concentrated under reduced pressure to give 50.0 mg of the intermediate. To a solution of the intermediate in dichloromethane (2.0 mL), were added triethylamine (183.0 µL) and isopropenyl chloroformate (18.0 µL). The reaction mixture was stirred at room temperature for 12 hours. Dichloromethane (5.0 mL) and brine (5.0 mL) were added to the reaction mixture and then the organic layer was separated. Dichloromethane (5.0 mL) was added to the water layer and then the organic layer was separated. The combined organic layer was dried over anhydrous sodium sulfate and then concentrated under reduced pressure to give a colorless oily residue. The residue was purified with silica gel column chromatography (hexane/ethyl acetate=1/1) to give 26.2 mg of the titled compound as a white solid (Yield: 14.0%).

$^1$H-NMR (CDCl$_3$) δ 8.56 (d, 1H), 7.96 (d, 1H), 7.84 (t, 1H), 7.70 (d, 1H), 7.39 (dt, 2H), 4.71-4.68 (m, 2H), 4.62 (d, 2H), 4.61-4.54 (m, 1H), 3.13 (m, 2H), 2.86 (s, 3H), 1.98 (s, 3H), 1.87 (m, 4H), 1.44 (d, 6H)

Example 60

2-(4-((5-ethylpyrimidin-2-yl)(methyl)amino)piperidin-1-yl)-5-(3-fluoro-4-(1-isopropyl-5-oxo-1H-1,2,4-triazol-4(5H)-yl)phenyl)nicotinonitrile The titled compound was prepared in accordance with the same procedures as in Example 59, using 2-chloro-5-ethylpyrimidine (5.0 g) instead of isopropenyl chloroformate.

Yield: 13.5%

$^1$H-NMR (CDCl$_3$) δ 8.56 (d, 1H), 8.20 (s, 2H), 7.95 (d, 1H), 7.83 (t, 1H), 7.70 (d, 1H), 7.39 (dt, 2H), 4.95 (m, 1H), 4.68 (d, 2H), 4.59 (m, 1H), 3.23 (t, 2H), 3.03 (s, 3H), 2.48 (q, 2H), 1.96-1.85 (m, 4H), 1.44 (d, 6H), 1.20 (t, 3H)

Example 61 tert-butyl 1-(3-cyano-5-(4-(1-(2-(diethylamino)ethyl)-5-oxo-1H-1,2,4-triazol-4(5H)-yl)-3-fluoro phenyl)pyridin-2-yl)piperidin-4-yl(methyl)carbamate The titled compound was prepared in accordance with the same procedures as in Example 58, using 4-(4-bromo-2-fluorophenyl)-1-[2-(diethylamino)ethyl]-1H-1,2,4-triazol-5(4H)-one (145.0 mg) prepared in Preparation 5 instead of 4-(4-bromo-2-fluorophenyl)-1-propyl-1H-1,2,4-triazol-5(4H)-one.

Yield: 12.4%

$^1$H-NMR (CDCl$_3$) δ 8.54 (d, 1H), 7.94 (d, 1H), 7.83 (t, 1H), 7.70 (d, 1H), 7.37 (t, 2H), 4.61 (d, 2H), 3.95 (t, 2H), 3.11 (m, 2H), 2.87 (t, 2H), 2.76 (s, 3H), 2.61 (q, 4H), 1.82 (m, 4H), 1.48 (s, 9H), 1.04 (t, 6H)

Example 62

5-(3-fluoro-4-(5-oxo-1-propyl-1H-1,2,4-triazol-4 (5H)-yl)phenyl)-2-(4-(3-isopropyl-1,2,4-oxadiazol-5-yl)piperidin-1-yl)nicotinonitrile Step 1: tert-butyl 4-(3-isopropyl-1,2,4-oxadiazol-5-yl)piperidin-1-carboxylate A solution of 1-(tert-butoxycarbonyl)-4-piperidinecarboxylic acid (100.0 g) in ethyl acetate (1.0 L) was cooled to 0° C. and then 4-methylmorpholine (52.7 mL) and isopropyl formate (58.8 mL) were added thereto. The reaction mixture was stirred at room temperature for 12 hours and then concentrated under reduced pressure. Ethyl acetate (500.0 mL) and brine (500.0 mL) were added to the residue and then the organic layer was separated. Ethyl acetate (300.0 mL) was added to the water layer and then the organic layer was separated. The combined organic layer was dried over anhydrous sodium sulfate and then concentrated under reduced pressure to give a yellow oily residue. The residue was dissolved in N,N-dimethylformamide (1.0 L) and then N-hydroxybutyramide (49.0 mL) was added thereto. The reaction mixture was stirred at 110° C. for 7 hours, cooled to room temperature, and then concentrated under reduced pressure. Ethyl acetate (500.0 mL) and brine (500.0 mL) were added to the residue and then the organic layer was separated. Ethyl acetate (300.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=5/1) to give 50.9 g of the titled compound as a white solid (Yield: 39.5%).

$^1$H-NMR (CDCl$_3$) δ 4.15-4.09 (m, 2H), 3.11-3.05 (m, 2H), 2.97 (t, 2H), 2.08-2.04 (m, 2H), 1.87-1.77 (m, 2H), 1.47 (s, 9H), 1.33 (d, 6H)

Step 2: 3-isopropyl-5-(piperidin-4-yl)-1,2,4-oxadiazole

To a solution of tert-butyl 4-(3-isopropyl-1,2,4-oxadiazol-5-yl)piperidin-1-carboxylate (20.5 g) prepared in Step 1 in ethyl acetate (200.0 mL), was added an aqueous solution of hydrochloric acid (4.0 M, 41.6 mL). The reaction mixture was stirred at room temperature for 4 hours and then concentrated under reduced pressure. The resulting residue was dried in an oven to give 13.6 g of the titled compound as a white solid (Yield: 100.0%).

$^1$H-NMR (MeOD) δ 3.72-3.60 (m, 2H), 3.53-3.35 (m, 2H), 3.25-3.10 (m, 2H), 3.10-2.90 (m, 1H), 2.44-2.20 (m, 2H), 2.15-1.90 (m, 2H), 1.31 (d, 6H)

Step 3: 5-bromo-2-(4-(3-isopropyl-1,2,4-oxadiazol-5-yl)piperidin-1-yl)nicotinonitrile To a solution of 3-isopropyl-5-(piperidin-4-yl)-1,2,4-oxadiazole (13.6 g) Prepared in Step 2 in a mixed solvent of toluene (250.0 mL) and N,N-dimethylformamide (500.0 mL), was added potassium carbonate (19.2 g). The reaction mixture was stirred at room temperature for 10 minutes and then 5-bromo-2-chloronicotinonitrile (15.1 g) was added thereto. The reaction mixture was stirred at 100° C. for 12 hours, cooled to room temperature, and then concentrated under reduced pressure. Ethyl acetate (500.0 mL) and brine (500.0 mL) were added to the residue and then the organic layer was separated. Ethyl acetate (300.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=5/1) to give 23.3 g of the titled compound as a white solid (Yield: 89.4%), $^1$H-NMR (CDCl$_3$) δ 8.35 (s, 1H), 7.85 (s, 1H), 4.36 (t, 1H), 4.32 (t, 1H), 3.32-3.19 (m, 3H), 3.11-3.04 (m, 1H), 2.24-2.19 (m, 2H), 2.10-2.02 (m, 2H), 1.33 (d, 6H)

Step 4: 2-(4-(3-isopropyl-1,2,4-oxadiazol-5-yl)piperidin-1-yl)-5-(4,4,5,5-tetramethyl-1,3,2-dioxaborolan-2-yl)nicotinonitrile To a solution of 5-bromo-2-(4-(3-isopropyl-1,2,4-oxadiazol-5-yl)piperidin-1-yl)nicotinonitrile (5.0 g) prepared in Step 3 in 1,4-dioxane (50.0 mL), were added potassium acetate (2.9 g), bis(pinacolato)diboron (3.2 g), 1,1'-bis(diphenylphosphino)ferrocene (161.0 mg) and [1,1'-bis(diphenylphosphino)ferrocene]dichloropalladium(II) (237.2 mg). The reaction mixture was stirred at 110° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=3/1) to give 2.7 g of the titled compound as a white solid (Yield: 65.0%).

$^{1}$H-NMR (CDCl$_{3}$) δ 8.35 (s, 1H), 7.85 (s, 1H), 4.36 (t, 1H), 4.32 (t, 1H), 3.32-3.19 (m, 3H), 3.11-3.04 (m, 1H), 2.24-2.19 (m, 2H), 2.10-2.02 (m, 2H), 1.33 (d, 6H), 1.32 (s, 12H)

Step 5: 5-(3-fluoro-4-(5-oxo-1-propyl-1H-1,2,4-triazol-4(5H)-yl)phenyl)-2-(4-(3-isopropyl-1,2,4-oxadiazol-5-yl)piperidin-1-yl)nicotinonitrile To a solution of 2-(4-(3-isopropyl-1,2,4-oxadiazol-5-yl)piperidin-1-yl)-5-(4,4,5,5-tetramethyl-1,3,2-dioxaborolan-2-yl)nicotinonitrile (50.0 mg) prepared in Step 4, 4-(4-bromo-2-fluorophenyl)-1-propyl-1H-1,2,4-triazol-5(4H)-one (35.4 mg) prepared in Preparation 2 and tetrakis(triphenylphosphine)palladium(0) (6.9 mg) in N,N-dimethylformamide (5.0 mL), was added an aqueous solution of sodium carbonate (2.0 M, 1.0 mL). The reaction mixture was stirred at 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=1/1) to give 28.3 mg of the titled compound as a white solid (Yield: 46.6%).

$^{1}$H-NMR (CDCl$_{3}$) δ 8.56 (d, 1H), 7.96 (d, 1H), 7.82 (t, 1H), 7.71 (d, 1H), 7.39 (m, 2H), 4.68 (m, 2H), 4.35 (m, 1H), 3.85 (t, 2H), 3.38 (m, 2H), 3.26 (m, 1H), 3.07 (m, 1H), 2.24 (m, 2H), 2.13 (m, 2H), 1.87 (m, 2H), 1.34 (d, 6H), 1.02 (t, 3H)

Example 63

5-(4-(1-(2-(diethylamino)ethyl)-5-oxo-1H-1,2,4-triazol-4(5H)-yl)-3-fluorophenyl)-2-(4-(3-isopropyl-1,2,4-oxadiazol-5-yl)piperidin-1-yl)nicotinonitrile The titled compound was prepared in accordance with the same procedures as in Step 5 of Example 62, using 4-(4-bromo-2-fluorophenyl)-1-[2-(diethylamino)ethyl]-1H-1,2,4-triazol-5(4H)-one (42.2 mg) prepared in Preparation 5 instead of 4-(4-bromo-2-fluorophenyl)-1-propyl-1H-1,2,4-triazol-5(4H)-one.

Yield: 61.5%

$^{1}$H-NMR (CDCl$_{3}$) δ 8.56 (d, 1H), 7.96 (d, 1H), 7.81 (t, 1H), 7.70 (d, 1H), 7.39 (m, 2H), 4.48 (m, 2H), 3.95 (m, 4H), 3.36 (m, 2H), 3.27 (m, 1H), 3.07 (m, 1H), 2.88 (m, 4H), 2.22 (m, 2H), 2.10 (m, 2H), 1.34 (d, 7H), 1.03 (t, 6H)

Example 64

5-(3-fluoro-4-(5-oxo-1-(pyrrolidin-1-ylmethyl)-1H-1,2,4-triazol-4(5H)-yl)phenyl)-2-(4-(3-isopropyl-1,2,4-oxadiazol-5-yl)piperidin-1-yl)nicotinonitrile The titled compound was prepared in accordance with the same procedures as in Step 5 of Example 62, using 4-(4-bromo-2-fluorophenyl)-1-(pyrrolidin-1-ylmethyl)-1H-1,2,4-triazol-5(4H)-one (100.0 mg) prepared in Preparation 33 instead of 4-(4-bromo-2-fluorophenyl)-1-propyl-1H-1,2,4-triazol-5(4H)-one.

Yield: 55.1%

$^{1}$H-NMR (CDCl$_{3}$) δ 8.57 (d, 1H), 7.96 (d, 1H), 7.82 (t, 1H), 7.72 (d, 1H), 7.39 (m, 2H), 4.86 (s, 2H), 4.48 (d, 2H), 3.37 (m, 2H), 3.26 (m, 1H), 3.09 (m, 1H), 2.85 (m, 2H), 2.25 (m, 2H), 2.13 (m, 2H), 1.80 (m, 2H), 1.34 (d, 6H)

Example 65

5-(4-(1-ethyl-5-oxo-1H-1,2,4-triazol-4(5H)-yl)phenyl)-2-(4-(3-isopropyl-1,2,4-oxadiazol-5-yl)piperidin-1-yl)nicotinonitrile The titled compound was prepared in accordance with the same procedures as in Step 5 of Example 62, using 4-(4-bromophenyl)-1-ethyl-1H-1,2,4-triazol-5(4H)-one (50.0 mg) prepared in Preparation 34 instead of 4-(4-bromo-2-fluorophenyl)-1-propyl-1H-1,2,4-triazol-5(4H)-one.

Yield: 56.3%

$^{1}$H-NMR (CDCl$_{3}$) δ 8.59 (d, 1H), 7.98 (d, 1H), 7.74 (s, 1H), 7.68 (d, 2H), 7.59 (d, 2H), 4.50 (d, 2H), 3.94 (q, 2H), 3.35 (m, 2H), 3.25 (m, 1H), 3.08 (m, 1H), 2.25 (m, 2H), 2.11 (m, 2H), 1.34 (d, 6H)

Example 66

5-(3-fluoro-4-(5-oxo-1-propyl-1H-1,2,4-triazol-4(5H)-yl)phenyl)-2-(4-(5-isopropyl-1,2,4-oxadiazol-3-yl)piperidin-1-yl)nicotinonitrile Step 1: (Z)-tert-butyl 4-(N'-hydroxycarbamimidoyl)piperidin-1-carboxylate To a solution of 1-BOC-4-cyano-piperidine (100.0 g) in ethanol (450.0 mL), were added triethylamine (70.3 mL) and hydroxyamine hydrochloride (35.0 g). The reaction mixture was stirred at 90° C. for 12 hours, cooled to room temperature, and then concentrated under reduced pressure to give 114.5 g of the titled compound as a white solid (Yield: 99.0%).

$^{1}$H-NMR (CDCl$_{3}$) δ 3.52 (t, 4H), 3.20 (t, 4H), 1.46 (s, 9H)

Step 2: tert-butyl 4-(5-isopropyl-1,2,4-oxadiazol-3-yl)piperidin-1-carboxylate

A solution of (Z)-tert-butyl 4-(N'-hydroxycarbamimidoyl)piperidin-1-carboxylate (114.5 g) prepared in Step 1 and triethylamine (66.3 mL) in toluene (300.0 mL) was cooled to 0° C. and then isobutyryl chloride (49.8 mL) was slowly added thereto. The reaction mixture was stirred at 130° C. for 5 hours, cooled to room temperature, and then concentrated under reduced pressure. Ethyl acetate (100.0 mL) and brine (100.0 mL) were added to the residue and then the organic layer was separated. Ethyl acetate (100.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=2/1) to give 69.0 g of the titled compound as a white solid (Yield: 31.5%).

$^{1}$H-NMR (CDCl$_{3}$) δ 8.36 (s, 1H), 8.21 (s, 2H), 7.86 (s, 1H), 3.94 (s, 4H), 3.81 (s, 4H), 2.49 (q, 2H), 1.20 (t, 3H)

Step 3: 5-isopropyl-3-(piperidin-4-yl)-1,2,4-oxadiazole hydrochloride

To a solution of tert-butyl 4-(5-isopropyl-1,2,4-oxadiazol-3-yl)piperidin-1-carboxylate (9.0 g) prepared in Step 2 in ethyl acetate (30.0 mL), was added an aqueous solution of hydrochloric acid (4.0 M, 70.0 mL). The reaction mixture was stirred at room temperature for 1 hour and then concentrated under reduced pressure to give 6.0 g of the titled compound as a white solid (Yield: 85.2%).

$^1$H-NMR (MeOD) δ 8.18 (s, 2H), 3.76 (s, 4H), 3.49 (s, 4H), 2.47 (q, 2H), 1.19 (t, 3H)

Step 4: 5-bromo-2-(4-(5-isopropyl-1,2,4-oxadiazol-3-yl)piperidin-1-yl)nicotinonitrile To a solution of 5-isopropyl-3-(piperidin-4-yl)-1,2,4-oxadiazole hydrochloride (4.3 g) prepared in Step 3 in a mixed solvent of toluene (20.0 mL) and N,N-dimethylformamide (40.0 mL), was added potassium carbonate (7.7 g). The reaction mixture was stirred at room temperature for 10 minutes and then 5-bromo-2-chloronicotinonitrile (4.1 g) was added thereto. The reaction mixture was stirred at 100° C. for 12 hours, cooled to room temperature, and then concentrated under reduced pressure. Ethyl acetate (30.0 mL) and brine (30.0 mL) were added to the residue and then the organic layer was separated. Ethyl acetate (30.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=8/1) to give 2.8 g of the titled compound as a yellow oil (Yield: 40.5%).

$^1$H-NMR (CDCl$_3$) δ 8.35 (s, 1H), 7.85 (s, 1H), 4.36 (t, 1H), 4.32 (t, 1H), 3.32-3.19 (m, 3H), 3.11-3.04 (m, 1H), 2.24-2.19 (m, 2H), 2.10-2.02 (m, 2H), 1.33 (d, 6H)

Step 5: 2-(4-(5-isopropyl-1,2,4-oxadiazol-3-yl)piperidin-1-yl)-5-(4,4,5,5-tetramethyl-1,3,2-dioxaborolan-2-yl)nicotinonitrile To a solution of 5-bromo-2-(4-(5-isopropyl-1,2,4-oxadiazol-3-yl)piperidin-1-yl)nicotinonitrile (2.8 g) prepared in Step 4 in 1,4-dioxane (60.0 mL), were added potassium acetate (2.2 g), bis(pinacolato)diboron (2.3 g), 1,1'-bis(diphenylphosphino)ferrocene (128.0 mg) and [1,1'-bis(diphenylphosphino)ferrocene]dichloropalladium(II) (185.0 mg). The reaction mixture was stirred at 110° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=4/1) to give 1.1 g of the titled compound as a white solid (Yield: 29.0%).

$^1$H-NMR (CDCl$_3$) δ 8.35 (s, 1H), 7.85 (s, 1H), 4.36 (t, 1H), 4.32 (t, 1H), 3.32-3.19 (m, 3H), 3.11-3.04 (m, 1H), 2.24-2.19 (m, 2H), 2.10-2.02 (m, 2H), 1.33 (d, 6H), 1.32 (s, 12H)

Step 6: 5-(3-fluoro-4-(5-oxo-1-propyl-1H-1,2,4-triazol-4(5H)-yl)phenyl)-2-(4-(5-isopropyl-1,2,4-oxadiazol-3-yl)piperidin-1-yl)nicotinonitrile To a solution of 2-(4-(5-isopropyl-1,2,4-oxadiazol-3-yl)piperidin-1-yl)-5-(4,4,5,5-tetramethyl-1,3,2-dioxaborolan-2-yl)nicotinonitrile (61.0 mg) prepared in Step 5, 4-(4-bromo-2-fluorophenyl)-1-propyl-1H-1,2,4-triazol-5(4H)-one (55.0 mg) prepared in Preparation 2 and tetrakis(triphenylphosphine)palladium(0) (7.0 mg) in N,N-dimethylformamide (5.0 mL), was added an aqueous solution of sodium carbonate (2.0 M, 1.0 mL). The reaction mixture was stirred at 85° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=1/1) to give 4.6 mg of the titled compound as a white solid (Yield: 7.4%).

$^1$H-NMR (CDCl$_3$) δ 8.56-8.55 (d, 1H), 7.95-7.94 (d, 1H), 7.82-7.80 (d, 1H), 7.71-7.70 (d, 1H), 7.41-7.36 (m, 2H), 4.55-4.51 (d, 1H), 3.86-3.82 (m, 2H), 3.35-3.32 (m, 2H), 3.29-3.19 (m, 1H), 2.19-2.16 (t, 3H), 2.07-2.01 (t, 2H), 1.88-1.84 (m, 2H), 1.41-1.39 (d, 6H), 1.01-0.98 (t, 3H)

Example 67

5-(4-(1-(2-(diethylamino)ethyl)-5-oxo-1H-1,2,4-triazol-4(5H)-yl)-3-fluorophenyl)-2-(4-(5-isopropyl-1,2,4-oxadiazol-3-yl)piperidin-1-yl)nicotinonitrile The titled compound was prepared in accordance with the same procedures as in Step 6 of Example 66, using 4-(4-bromo-2-fluorophenyl)-1-[2-(diethylamino)ethyl]-1H-1,2,4-triazol-5(4H)-one (86.0 mg) prepared in Preparation 5 instead of 4-(4-bromo-2-fluorophenyl)-1-propyl-1H-1,2,4-triazol-5(4H)-one.

Yield: 33.3%

$^1$H-NMR (CDCl$_3$) δ 8.01 (s, 1H), 7.71-7.61 (m, 2H), 7.44-7.35 (m, 3H), 4.55-4.51 (d, 2H), 3.31-3.21 (m, 2H), 2.95 (s, 3H), 2.88-2.83 (m, 6H), 2.62-2.57 (m, 6H), 2.19-2.01 (m, 4H), 1.23 (s, 3H), 1.06-1.01 (m, 9H)

Example 68

5-(3-fluoro-4-(5-oxo-1-(pyrrolidin-1-ylmethyl)-1H-1,2,4-triazol-4(5H)-yl)phenyl)-2-(4-(3-isopropyl-1,2,4-oxadiazol-5-yl)piperidin-1-yl)nicotinonitrile The titled compound was prepared in accordance with the same procedures as in Step 6 of Example 66, using 4-(4-bromo-2-fluorophenyl)-1-(pyrrolidin-1-ylmethyl)-1H-1,2,4-triazol-5(4H)-one (100.0 mg) prepared in Preparation 33 instead of 4-(4-bromo-2-fluorophenyl)-1-propyl-1H-1,2,4-triazol-5(4H)-one.

Yield: 41.7%

$^1$H-NMR (CDCl$_3$) δ 8.57 (s, 1H), 7.96 (s, 1H), 7.82 (t, 1H), 7.72 (s, 1H), 7.39 (m, 2H), 4.86 (s, 2H), 4.48 (d, 2H), 3.37 (m, 2H), 3.26 (m, 1H), 3.09 (m, 1H), 2.85 (m, 2H), 2.25 (m, 2H), 2.13 (m, 2H), 1.80 (m, 2H), 1.34 (d, 6H)

Example 69

2-(4-(5-isopropyl-1,2,4-oxadiazol-3-yl)piperidin-1-yl)-5-(4-(1-(2-methoxyethyl)-5-oxo-1H-1,2,4-triazol-4(5H)-yl)phenyl)nicotinonitrile The titled compound was prepared in accordance with the same procedures as in Step 6 of Example 66, using 4-(4-bromophenyl)-1-(2-methoxyethyl)-1H-1,2,4-triazol-5(4H)- one (95.1 mg) prepared in Preparation 29 instead of 4-(4-bromo-2-fluorophenyl)-1-propyl-1H-1,2,4-triazol-5(4H)-one.

Yield: 30.7%

¹H-NMR (CDCl₃) δ 8.57 (s, 1H), 7.97 (s, 1H), 7.75 (s, 1H), 7.67 (dd, 2H), 7.59 (dd, 2H), 4.51 (d, 2H), 4.09 (t, 2H), 3.77 (t, 2H), 3.41 (s, 3H), 3.33-3.27 (m, 2H), 3.23-3.19 (m, 1H), 3.14-3.08 (m, 1H), 2.20-2.10 (m, 2H), 2.10-2.00 (m, 2H), 1.40 (d, 6H)

Example 70

(R)-2-(4-(5-isopropyl-1,2,4-oxadiazol-3-yl)piperidin-1-yl)-5-(4-(5-oxo-1-(tetrahydrofuran-3-yl)-1H-1,2,4-triazol-4(5H)-yl)phenyl)nicotinonitrile The titled compound was prepared in accordance with the same procedures as in Step 6 of Example 66, using (R)-4-(4-bromophenyl)-1-(tetrahydrofuran-3-yl)-1H-1,2,4-triazol-5(4H)-one (98.9 mg) prepared in Preparation 30 instead of 4-(4-bromo-2-fluorophenyl)-1-propyl-1H-1,2,4-triazol-5(4H)-one.

Yield: 35.2%

¹H-NMR (CDCl₃) δ 8.57 (s, 1H), 7.97 (s, 1H), 7.75 (s, 1H), 7.67 (dd, 2H), 7.59 (dd, 2H), 5.05-4.95 (m, 1H), 4.51 (d, 2H), 4.18-3.92 (m, 4H), 3.34-3.11 (m, 4H), 2.38-2.34 (m, 2H), 2.20-2.10 (m, 2H), 2.10-1.90 (m, 2H), 1.40 (d, 6H)

Example 71

(S)-2-(4-(5-isopropyl-1,2,4-oxadiazol-3-yl)piperidin-1-yl)-5-(4-(5-oxo-1-(tetrahydrofuran-3-yl)-1H-1,2,4-triazol-4(5H)-yl)phenyl)nicotinonitrile The titled compound was prepared in accordance with the same procedures as in Step 6 of Example 66, using (S)-4-(4-bromophenyl)-1-(tetrahydrofuran-3-yl)-1H-1,2,4-triazol-5(4H)-one (98.9 mg) prepared in Preparation 36 instead of 4-(4-bromo-2-fluorophenyl)-1-propyl-1H-1,2,4-triazol-5(4H)-one.

Yield: 34.2%

¹H-NMR (CDCl₃) δ 8.57 (s, 1H), 7.97 (s, 1H), 7.75 (s, 1H), 7.67 (dd, 2H), 7.59 (dd, 2H), 5.08-4.95 (m, 1H), 4.51 (d, 2H), 4.18-3.91 (m, 4H), 3.35-3.08 (m, 4H), 2.39-2.34 (m, 2H), 2.20-2.10 (m, 2H), 2.10-1.95 (m, 2H), 1.40 (d, 6H)

Example 72

2-(4-(4-(5-cyano-6-(4-(5-isopropyl-1,2,4-oxadiazol-3-yl)piperidin-1-yl)pyridin-3-yl)phenyl)-5-oxo-4,5-dihydro-1H-1,2,4-triazol-1-yl)acetamide The titled compound was prepared in accordance with the same procedures as in Step 6 of Example 66, using 2-[4-(4-bromophenyl)-5-oxo-4,5-dihydro-1H-1,2,4-triazol-1-yl]acetamide (50.0 mg) prepared in Preparation 38 instead of 4-(4-bromo-2-fluorophenyl)-1-propyl-1H-1,2,4-triazol-5(4H)-one.

Yield: 60.5%

¹H-NMR (DMSO) δ 8.83 (s, 1H), 8.57 (s, 1H), 8.49 (s, 1H), 7.90 (d, 2H), 7.82 (d, 2H), 4.50 (s, 2H), 4.40-4.32 (m, 2H), 3.40-3.10 (m, 4H), 2.20-2.00 (m, 2H), 1.90-1.70 (m, 2H), 1.31 (d, 6H)

Example 73

5-(4-(1-isopropyl-5-oxo-1H-1,2,4-triazol-4(5H)-yl)phenyl)-2-(4-(5-(trifluoromethyl)-1,3,4-oxadiazol-2-yl)piperidin-1-yl)nicotinonitrile Step 1: tert-butyl 4-(2H-tetrazol-5-yl)piperidin-1-carboxylate To a solution of 1-BOC-4-cyano-piperidine (5.0 g) in N,N-dimethylformamide (90.0 mL), were added sodium azide (5.0 g) and ammonium chloride (4.1 g). The reaction mixture was stirred at 110° C. for 3 days and then cooled to room temperature. To the reaction mixture, were added dichloromethane (200.0 mL) and an aqueous solution of hydrochloric acid (1N, 200.0 mL). The separated organic layer was washed with brine, dried over anhydrous sodium sulfate, and then concentrated under reduced pressure to give 4.6 g of the titled compound as a white solid (Yield: 76.0%).

¹H-NMR (CDCl₃) δ 4.30-4.15 (m, 2H), 3.39-3.33 (m, 1H), 3.10-2.95 (m, 2H), 2.19-2.06 (m, 2H), 1.95-1.86 (m, 2H), 1.49 (s, 9H)

Step 2: tert-butyl 4-(5-(trifluoromethyl)-1,3,4-oxadiazol-2-yl)piperidin-1-carboxylate A solution of tert-butyl 4-(2H-tetrazol-5-yl)piperidin-1-carboxylate (500.0 mg) prepared in Step 1 in acetonitrile (40.0 mL) was cooled to 0° C. and then anhydrous trifluoroacetic acid (446.0 μL) was slowly added. The reaction mixture was stirred at room temperature for 20 hours and then concentrated under reduced pressure. Ethyl acetate (50.0 mL) and an aqueous solution of sodium hydrogen carbonate (70.0 mL) were added to the residue and then the organic layer was separated. Ethyl acetate (50.0 mL) was added to the water layer and then the organic layer was separated. The combined organic layer was dried over anhydrous sodium sulfate and then concentrated under reduced pressure to give a yellow oily residue. The residue was purified with silica gel column chromatography (ethyl acetate) to give 347.0 mg of the titled compound as a yellow oil (Yield: 51.0%).

¹H-NMR (CDCl₃) δ 4.15-4.11 (m, 2H), 3.18-3.14 (m, 1H), 3.00-2.93 (m, 2H), 2.13-2.09 (m, 2H), 1.89-1.82 (m, 2H), 1.47 (s, 9H)

Step 3: 2-(piperidin-4-yl)-5-(trifluoromethyl)-1,3,4-oxadiazole

A solution of tert-butyl 4-(5-(trifluoromethyl)-1,3,4-oxadiazol-2-yl)piperidin-1-carboxylate (347.0 mg) prepared in Step 2 in an aqueous solution of hydrochloric acid (4.0 M, 3.0 mL) was stirred at room temperature for 1 hours. The reaction mixture was neutralized to pH 8 with a 1N sodium hydroxide solution and then extracted with ethyl acetate twice. The combined organic extract was dried over anhydrous sodium sulfate and then concentrated under reduced pressure to give 83.0 mg of the titled compound as a white solid (Yield: 35.0%).

¹H-NMR (CDCl₃) δ 4.47-4.41 (m, 1H), 4.10-4.06 (m, 1H), 3.46-3.33 (m, 2H), 3.24-3.16 (m, 1H), 2.30-2.25 (m, 2H), 2.08-1.96 (m, 2H)

Step 4: 5-bromo-2-(4-(5-(trifluoromethyl)-1,3,4-oxadiazol-2-yl)piperidin-1-yl)nicotinonitrile To a solution of 2-(piperidin-4-yl)-5-(trifluoromethyl)-1,3,4-oxadiazole (83.0 mg) prepared in Step 3 in a mixed solvent of toluene (1.2 mL) and N,N-dimethylformamide (2.4 mL), was added potassium carbonate (104.0 mg). The reaction mixture was stirred at room temperature for 10 minutes and then 5-bromo-2-chloronicotinonitrile (82.0 mg) was added thereto. The reaction mixture was stirred at 100° C. for 12 hours, cooled to room temperature, and then concentrated under reduced pressure. Ethyl acetate (10.0 mL) and brine (10.0 mL) were added to the residue and then the organic layer was separated. Ethyl acetate (10.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=2/1) to give 16.4 mg of the titled compound as a green solid (Yield: 10.9%).

$^1$H-NMR (CDCl$_3$) δ 8.37 (d, 1H), 7.87 (d, 1H), 4.39-4.33 (m, 2H), 3.36-3.25 (m, 3H), 2.29-2.24 (m, 2H), 2.14-2.03 (m, 2H)

Step 5: 5-(4,4,5,5-tetramethyl-1,3,2-dioxaborolan-2-yl)-2-(4-(5-(trifluoromethyl)-1,3,4-oxadiazol-2-yl)piperidin-1-yl)nicotinonitrile To a solution of 5-bromo-2-(4-(5-(trifluoromethyl)-1,3,4-oxadiazol-2-yl)piperidin-1-yl)nicotinonitrile (2.0 g) prepared in Step 4 in 1,4-dioxane (50.0 mL), were added potassium acetate (1.5 g), bis(pinacolato)diboron (1.6 g), 1,1'-bis(diphenylphosphino)ferrocene (83.0 mg) and [1,1'-bis(diphenylphosphino)ferrocene]dichloropalladium(II) (122.0 mg). The reaction mixture was stirred at 110° C. for 12 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=3/1) to give 1.2 g of the titled compound as a white solid (Yield: 53.7%).

$^1$H-NMR (CDCl$_3$) δ 8.35 (s, 1H), 7.85 (s, 1H), 4.36 (t, 1H), 4.32 (t, 1H), 3.32-3.19 (m, 3H), 3.11-3.04 (m, 1H), 2.24-2.19 (m, 2H), 2.10-2.02 (m, 2H), 1.33 (d, 6H), 1.32 (s, 12H)

Step 6: 5-(4-(1-isopropyl-5-oxo-1H-1,2,4-triazol-4(5H)-yl)phenyl)-2-(4-(5-(trifluoromethyl)-1,3,4-oxadiazol-2-yl)piperidin-1-yl)nicotinonitrile To a solution of 5-(4,4,5,5-tetramethyl-1,3,2-dioxaborolan-2-yl)-2-(4-(5-(trifluoromethyl)-1,3,4-oxadiazol-2-yl)piperidin-1-yl)nicotinonitrile (30.0 mg) prepared in Step 5, 4-(4-bromophenyl)-1-isopropyl-1H-1,2,4-triazol-5(4H)-one (18.9 mg) prepared in Preparation 39 and tetrakis(triphenylphosphine)palladium(0) (3.5 mg) in N,N-dimethylformamide (2.0 mL), was added an aqueous solution of sodium carbonate (2.0 M, 0.1 mL). The reaction mixture was stirred at 80° C. for 26 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=1/1) to give 3.5 mg of the titled compound as a white solid (Yield: 10.0%).

$^1$H-NMR (CDCl$_3$) δ 8.60 (d, 1H), 8.00 (d, 1H), 7.73 (s, 1H), 7.69 (dd, 2H), 7.60 (dd, 2H), 4.60-4.56 (m, 1H), 4.50-4.45 (m, 2H), 3.38-3.31 (m, 3H), 2.32-2.29 (m, 2H), 2.15-2.12 (m, 2H), 1.43 (d, 6H)

Example 74

5-(3-fluoro-4-(1-isopropyl-5-oxo-1H-1,2,4-triazol-4(5H)-yl)phenyl)-2-(4-(5-(trifluoro methyl)-1,3,4-oxadiazol-2-yl)piperidin-1-yl)nicotinonitrile The titled compound was prepared in accordance with the same procedures as in Step 6 of Example 73, using 4-(4-bromo-2-fluorophenyl)-1-isopropyl-1H-1,2,4-triazol-5(4H)-one (20.1 mg) prepared in Preparation 3 instead of 4-(4-bromophenyl)-1-isopropyl-1H-1,2,4-triazol-5(4H)-one.

Yield: 16.0%

$^1$H-NMR (CDCl$_3$) δ 8.58 (d, 1H), 7.98 (d, 1H), 7.90-7.82 (m, 1H), 7.70 (s, 1H), 7.42-7.36 (m, 2H), 4.60-4.57 (m, 1H), 4.57-4.49 (m, 2H), 3.40-3.33 (m, 3H), 2.32-2.29 (m, 2H), 2.14-2.11 (m, 2H), 1.44 (d, 6H)

Example 75

(S)-5-(3-fluoro-4-(5-oxo-1-(tetrahydrofuran-3-yl)-1H-1,2,4-triazol-4(5H)-yl)phenyl)-2-(4-(5-(trifluoromethyl)-1,3,4-oxadiazol-2-yl)piperidin-1-yl)nicotinonitrile The titled compound was prepared in accordance with the same procedures as in Step 6 of Example 73, using (S)-4-(4-bromo-2-fluorophenyl)-1-(tetrahydrofuran-3-yl)-1H-1,2,4-triazol-5(4H)-one (20.1 mg) prepared in Preparation 17 instead of 4-(4-bromophenyl)-1-isopropyl-1H-1,2,4-triazol-5(4H)-one.

Yield: 11.6%

$^1$H-NMR (CDCl$_3$) δ 8.58 (d, 1H), 7.98 (d, 1H), 7.90-7.82 (m, 1H), 7.70 (s, 1H), 7.42-7.36 (m, 2H), 4.60-4.57 (m, 1H), 4.57-4.49 (m, 2H), 3.40-3.33 (m, 3H), 2.32-2.29 (m, 2H), 2.14-2.11 (m, 2H), 1.44 (d, 6H)

Example 76

5-(3-fluoro-4-(1-(2-methoxyethyl)-5-oxo-1H-1,2,4-triazol-4(5H)-yl)phenyl)-2-(4-(5-(trifluoromethyl)-1,3,4-oxadiazol-2-yl)piperidin-1-yl)nicotinonitrile The titled compound was prepared in accordance with the same procedures as in Step 6 of Example 73, using 4-(4-bromo-2-fluorophenyl)-1-(2-methoxyethyl)-1H-1,2,4-triazol-5(4H)-one (21.2 mg) prepared in Preparation 4 instead of 4-(4-bromophenyl)-1-isopropyl-1H-1,2,4-triazol-5(4H)-one.

Yield: 7.5%

$^1$H-NMR (CDCl$_3$) δ 8.58 (d, 1H), 7.98 (d, 1H), 7.88-7.83 (m, 1H), 7.73 (s, 1H), 7.42-7.36 (m, 2H), 4.53-4.49 (m, 2H), 4.08 (t, 2H), 3.77 (t, 2H), 3.42 (s, 3H), 3.42-3.33 (m, 3H), 2.32-2.29 (m, 2H), 2.14-2.11 (m, 2H)

Example 77

5-(4-(1-isopropyl-5-oxo-1H-1,2,4-triazol-4(5H)-yl)phenyl)-2-(4-(5-(trifluoromethyl)-1,3,4-oxadiazol-2-yl)piperazin-1-yl)nicotinonitrile Step 1: tert-butyl 4-cyanopiperazin-1-carboxylate A solution of 1-BOC-piperazine (10.0 g) and sodium hydrogen carbonate (9.0 g) in a mixed solvent of dichloromethane (100.0 mL) and water (6.0 mL) was cooled to 0° C. and then cyanogen bromide (6.8 g) was added thereto. The reaction mixture was stirred at room temperature for 3 hours and then concentrated under reduced pressure. Dichloromethane (100.0 mL) and brine (100.0 mL) were added to the residue and then the organic layer was separated. Dichloromethane (10.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=1/1) to give 5.0 g of the titled compound as a white solid
(Yield: 44.1%).
$^1$H-NMR (CDCl$_3$) δ 3.53-3.50 (m, 4H), 3.21-3.18 (m, 4H), 1.46 (s, 9H)

Step 2: tert-butyl 4-(2H-tetrazol-5-yl)piperazin-1-carboxylate

To a solution of tert-butyl 4-cyanopiperazin-1-carboxylate (5.0 g) prepared in Step 1 in N,N-dimethylformamide (50.0 mL), were added sodium azide (4.6 g) and ammonium chloride (3.8 g). The reaction mixture was stirred at 110° C. for 17 hours and then cooled to room temperature. To the reaction mixture, were added ethyl acetate (50.0 mL) and an aqueous solution of hydrochloric acid (1N, 50.0 mL). The separated organic layer was washed with brine, dried over anhydrous sodium sulfate, and then concentrated under reduced pressure to give 4.6 g of the titled compound as a white solid (Yield: 76.4%).
$^1$H-NMR (CDCl$_3$) δ 13.5 (brs, 1H), 3.70-3.50 (m, 8H), 1.50 (s, 9H)

Step 3: tert-butyl 4-(5-(trifluoromethyl)-1,3,4-oxadiazol-2-yl)piperazin-1-carboxylate A solution of tert-butyl 4-(2H-tetrazol-5-yl)piperazin-1-carboxylate (500.0 mg) prepared in Step 2 in acetonitrile (50.0 mL) was cooled to 0° C. and then anhydrous trifluoroacetic acid (416.6 μL) was slowly added. The reaction mixture was stirred at room temperature for 16 hours and then concentrated under reduced pressure. Ethyl acetate (50.0 mL) and an aqueous solution of sodium hydrogen carbonate (70.0 mL) were added to the residue and then the organic layer was separated. Ethyl acetate (50.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=2/1) to give 432.4 mg of the titled compound as a yellow oil (Yield: 68.3%).
$^1$H-NMR (CDCl$_3$) δ 3.70-3.68 (m, 4H), 3.61-3.57 (m, 4H), 1.48 (s, 9H)

Step 4: 2-(piperazin-1-yl)-5-(trifluoromethyl)-1,3,4-oxadiazole hydrochloride A solution of tert-butyl 4-(5-(trifluoromethyl)-1,3,4-oxadiazol-2-yl)piperazin-1-carboxylate (432.4 mg) prepared in Step 3 in an aqueous solution of hydrochloric acid (4.0 M, 4.0 mL) was stirred at room temperature for 4 hours and then concentrated under reduced pressure to give 346.6 mg of the titled compound as a white solid (Yield: 100.0%).

$^1$H-NMR (MeOD) δ 3.74-3.71 (m, 4H), 3.40-3.37 (m, 4H)

Step 5: 5-bromo-2-(4-(5-(trifluoromethyl)-1,3,4-oxadiazol-2-yl)piperazin-1-yl)nicotinonitrile To a solution of 2-(piperazin-1-yl)-5-(trifluoromethyl)-1, 3,4-oxadiazole hydrochloride (346.6 mg) prepared in Step 4 in a mixed solvent of toluene (4.5 mL) and N,N-dimethylformamide (10.0 mL), was added potassium carbonate (556.8 mg). The reaction mixture was stirred at room temperature for 10 minutes and then 5-bromo-2-chloronicotinonitrile (437.9 mg) was added thereto. The reaction mixture was stirred at 100° C. for 4 hours, cooled to room temperature, and then concentrated under reduced pressure. Ethyl acetate (20.0 mL) and brine (20.0 mL) were added to the residue and then the organic layer was separated. Ethyl acetate (20.0 mL) was added to the water layer and then the organic layer was separated. The combined organic layer was dried over anhydrous sodium sulfate and then concentrated under reduced pressure to give a yellow oily residue. The residue was purified with silica gel column chromatography (hexane/ethyl acetate=4/1) to give 250.0 mg of the titled compound as a yellow solid (Yield: 30.8%).
$^1$H-NMR (CDCl$_3$) δ 8.39 (d, 1H), 7.90 (d, 1H), 3.82-3.81 (m, 4H), 3.78-3.77 (m, 4H)

Step 6: 5-(4,4,5,5-tetramethyl-1,3,2-dioxaborolan-2-yl)-2-(4-(5-(trifluoromethyl)-1,3,4-oxadiazol-2-yl)piperazin-1-yl)nicotinonitrile To a solution of 5-bromo-2-(4-(5-(trifluoromethyl)-1,3,4-oxadiazol-2-yl)piperazin-1-yl)nicotinonitrile (250.0 mg) prepared in Step 5 in 1,4-dioxane (25.0 mL), were added potassium acetate (182.6 mg), bis(pinacolato)diboron (204.7 mg), 1,1'-bis(diphenylphosphino)ferrocene (10.5 mg) and [1,1'-bis(diphenylphosphino)ferrocene]dichloropalladium (II) (15.2 mg). The reaction mixture was stirred at 110° C. for 3 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=2/1) to give 150.0 mg of the titled compound as a white solid (Yield: 53.7%).
$^1$H-NMR (CDCl$_3$) δ 8.66 (s, 1H), 8.20 (s, 1H), 3.95-3.92 (m, 4H), 3.78-3.75 (m, 4H), 1.34-1.26 (m, 12H)

Step 7: 5-(4-(1-isopropyl-5-oxo-1H-1,2,4-triazol-4 (5H)-yl)phenyl)-2-(4-(5-(trifluoromethyl)-1, 3,4-oxadiazol-2-yl)piperazin-1-yl)nicotinonitrile To a solution of 5-(4,4,5,5-tetramethyl-1,3,2-dioxaborolan-2-yl)-2-(4-(5-(trifluoromethyl)-1,3,4-oxadiazol-2-yl) piperazin-1-yl)nicotinonitrile (30.0 mg) prepared in Step 6, 4-(4-bromophenyl)-1-isopropyl-1H-1,2,4-triazol-5(4H)-one (18.9 mg) prepared in Preparation 39 and tetrakis(triphenylphosphine)palladium(0) (3.5 mg) in N,N-dimethylformamide (2.0 mL), was added an aqueous solution of sodium carbonate (2.0 M, 0.1 mL). The reaction mixture was stirred at 80° C. for 26 hours and then filtered through a celite pad. The filtrate was concentrated under reduced pressure. The resulting residue was diluted with ethyl acetate, washed with brine, dried over anhydrous sodium sulfate, and then concentrated under reduced pressure to give a yellow oily residue. The residue was purified with silica gel column chromatography (hexane/ethyl acetate=1/2) to give 4.0 mg of the titled compound as a white solid (Yield: 11.4%).
$^1$H-NMR (CDCl$_3$) δ 8.60 (d, 1H), 8.00 (d, 1H), 7.73 (s, 1H), 7.69 (dd, 2H), 7.60 (dd, 2H), 4.60-4.56 (m, 1H), 4.50-4.45 (m, 2H), 3.38-3.31 (m, 3H), 2.32-2.29 (m, 2H), 2.15-2.12 (m, 2H), 1.43 (d, 6H)

Example 78

5-(3-fluoro-4-(1-isopropyl-5-oxo-1H-1,2,4-triazol-4(5H)-yl)phenyl)-2-(4-(5-(trifluoro methyl)-1,3,4-oxadiazol-2-yl)piperazin-1-yl)nicotinonitrile The titled compound was prepared in accordance with the same procedures as in Step 7 of Example 77, using 4-(4-bromo-2-fluorophenyl)-1-isopropyl-1H-1,2,4-triazol-5(4H)-one (20.1 mg) prepared in Preparation 3 instead of 4-(4-bromophenyl)-1-isopropyl-1H-1,2,4-triazol-5(4H)-one.
Yield: 12.9%
$^1$H-NMR (CDCl$_3$) δ 8.58 (d, 1H), 7.98 (d, 1H), 7.90-7.82 (m, 1H), 7.70 (s, 1H), 7.42-7.36 (m, 2H), 4.60-4.57 (m, 1H), 4.57-4.49 (m, 2H), 3.40-3.33 (m, 3H), 2.32-2.29 (m, 2H), 2.14-2.11 (m, 2H), 1.44 (d, 6H)

Example 79

(S)-5-(3-fluoro-4-(5-oxo-1-(tetrahydrofuran-3-yl)-1H-1,2,4-triazol-4(5H)-yl)phenyl)-2-(4-(5-(trifluoromethyl)-1,3,4-oxadiazol-2-yl)piperazin-1-yl)nicotinonitrile The titled compound was prepared in accordance with the same procedures as in Step 7 of Example 77, using (S)-4-(4-bromo-2-fluorophenyl)-1-(tetrahydrofuran-3-yl)-1H-1,2,4-triazol-5(4H)-one (20.8 mg) prepared in Preparation 17 instead of 4-(4-bromophenyl)-1-isopropyl-1H-1,2,4-triazol-5(4H)-one.
Yield: 7.5%
$^1$H-NMR (CDCl$_3$) δ 8.58 (d, 1H), 7.98 (d, 1H), 7.90-7.82 (m, 1H), 7.70 (s, 1H), 7.42-7.36 (m, 2H), 4.60-4.57 (m, 1H), 4.57-4.49 (m, 2H), 3.40-3.33 (m, 3H), 2.32-2.29 (m, 2H), 2.14-2.11 (m, 2H), 1.44 (d, 6H)

Example 80

5-(3-fluoro-4-(1-(2-methoxyethyl)-5-oxo-1H-1,2,4-triazol-4(5H)-yl)phenyl)-2-(4-(5-(trifluoromethyl)-1,3,4-oxadiazol-2-yl)piperazin-1-yl)nicotinonitrile The titled compound was prepared in accordance with the same procedures as in Step 7 of Example 77, using 4-(4-bromo-2-fluorophenyl)-1-(2-methoxyethyl)-1H-1,2,4-triazol-5(4H)-one (21.2 mg) prepared in Preparation 4 instead of 4-(4-bromophenyl)-1-isopropyl-1H-1,2,4-triazol-5(4H)-one.
Yield: 10.5%
$^1$H-NMR (CDCl$_3$) δ 8.58 (d, 1H), 7.98 (d, 1H), 7.88-7.83 (m, 1H), 7.73 (s, 1H), 7.42-7.36 (m, 2H), 4.53-4.49 (m, 2H), 4.08 (t, 2H), 3.77 (t, 2H), 3.42 (s, 3H), 3.42-3.33 (m, 3H), 2.32-2.29 (m, 2H), 2.14-2.11 (m, 2H)

Experimental Example 1 cAMP Accumulation Assay

32 μl of an assay medium (DMEM supplemented with GlutaMax™ 99%, dialyzed FBS 1%, non-essential amino acid 1 mM, HEPES 25 mM, penicillin 100 U/ml, and streptomycin 100 μg/ml) was added to each well of a 384 black well plate and then the GPR119 CRE-bla CHO-K1 cells (Invitrogen) were seeded in 1×10$^4$ cells per well. Doxycycline was dissolved in the assay medium in the concentration of 1 μg/ml. The resulting solution (4 μl) was added to each well, which was then incubated in a 5% CO$_2$ incubator at 37° C. for about 20 to 24 hours. Each test compounds were diluted with the assay medium to prepare 10 samples, which have concentrations ranging from 1 μM to 3 μM, respectively. Each samples (8 μl) was added to each well, which was then incubated in a 5% CO$_2$ incubator at 37° C. for 5 hours. In case of the control group, the well was treated with a solution (8 μl) prepared by diluting dimethyl sulfoxide (DMSO) in the assay medium to 1%. The substrate mixture (8 μl) was added to each well, which was then left under darkness at room temperature for 2 hours. The substrate mixture contains the followings: 1 mM Live-BLAzer™-FRET B/G(CCF4-AM) substrate 6 μl, solution B 60 μl, solution C 904 μl, and solution D 30 μl.

Fluorescence intensity was determined under the wavelength conditions of 400 nm/465 nm (excitation/emission) for the blue channel and 400 nm/535 nm (excitation/emission) for the green channel, with the fluorescence microplate reader (SpectraFluor Plus. TECAN). The net activity of each well was calculated by subtracting the average value of the cell-free control group from the value of the unstimulated (i.e., non-treated) control group or the stimulated (i.e., test compound-treated) group at each wavelength. MBX-2982 (Metabolex) was used as a control drug. The response ratio was calculated by dividing the net signal ratio (465 nm/535 nm) of the control drug or the test compound by the net signal ratio (465 nm/535 nm) of the non-treated control group. The relative ratio (R.R) was calculated by dividing the maximum activity [Emax (fold)] of the test compound (i.e., % activity in comparison with the background) by the maximum activity [Emax (fold)] of the control drug (MBX-2982) [Emax (% RR)=(Emax of the test compound/Emax of MBX-2982)×100]. EC$_{50}$ (half maximal effective concentration) was calculated using the software for statistical analysis "Prism 5.0 (GraphPad)", based on the values obtained according to concentrations of the test compounds. The results are shown in Tables 1 and 2 below.

TABLE 1

| | Emax (% RR) | Emax (Fold) | EC$_{50}$ (nM) |
|---|---|---|---|
| Example 1 | 123.9 | 2.9 | 59.0 |
| Example 2 | 101.6 | 3.3 | 31.9 |
| Example 3 | 113.4 | 3.4 | 62.0 |
| Example 4 | 108.0 | 3.5 | 54.9 |
| Example 5 | 109.1 | 2.7 | 4.0 |
| Example 6 | 111.5 | 2.5 | 26.0 |
| Example 8 | 113.4 | 2.5 | 5.0 |
| Example 9 | 118.2 | 2.8 | 3.0 |
| Example 10 | 104.5 | 2.6 | 8.0 |
| Example 11 | 102.1 | 2.9 | 5.0 |
| Example 12 | 103.8 | 2.6 | 1.0 |
| Example 13 | 102.0 | 2.9 | 114.0 |
| Example 14 | 125.1 | 3.3 | 14.8 |
| Example 15 | 124.5 | 3.5 | 5.0 |
| Example 16 | 116.8 | 3.3 | 7.2 |
| Example 17 | 115.1 | 3.2 | 8.2 |
| Example 18 | 104.6 | 2.9 | 17.0 |
| Example 19 | 113.0 | 3.5 | 5.4 |
| Example 20 | 109.6 | 3.1 | 5.6 |
| Example 21 | 102.0 | 2.9 | 2.0 |
| Example 22 | 119.3 | 3.2 | 10.2 |
| Example 23 | 111.7 | 3.4 | 7.9 |
| Example 24 | 124.6 | 3.6 | 4.5 |

TABLE 1-continued

|  | Emax (% RR) | Emax (Fold) | EC$_{50}$ (nM) |
|---|---|---|---|
| Example 25 | 116.0 | 3.3 | 2.6 |
| Example 26 | 112.5 | 3.4 | 20.0 |
| Example 27 | 149.4 | 4.0 | 3.1 |
| Example 28 | 145.6 | 3.9 | 4.0 |
| Example 29 | 110.1 | 3.1 | 1.5 |
| Example 30 | 130.9 | 3.8 | 1.5 |
| Example 31 | 148.7 | 3.4 | 10.0 |
| Example 33 | 125.7 | 4.0 | 4.4 |
| Example 34 | 113.8 | 3.2 | 8.4 |
| Example 35 | 129.7 | 3.7 | 4.8 |
| Example 36 | 118.1 | 4.3 | 13.2 |
| Example 37 | 110.0 | 3.1 | 3.2 |
| Example 39 | 133.6 | 3.9 | 3.8 |
| Example 40 | 112.1 | 3.1 | 9.0 |

TABLE 2

|  | Emax (% RR) | Emax (Fold) | EC$_{50}$ (nM) |
|---|---|---|---|
| Example 41 | 113.4 | 3.1 | 5.0 |
| Example 42 | 109.3 | 3.0 | 21.0 |
| Example 43 | 130.9 | 3.8 | 1.5 |
| Example 44 | 130.9 | 3.8 | 1.5 |
| Example 45 | 144.7 | 4.2 | 7.3 |
| Example 46 | 133.3 | 3.9 | 4.2 |
| Example 47 | 141.6 | 3.2 | 12.0 |
| Example 48 | 109.1 | 3.0 | 16.0 |
| Example 49 | 144.7 | 4.2 | 7.3 |
| Example 58 | 105.4 | 2.6 | 16.0 |
| Example 59 | 100.8 | 2.5 | 31.0 |
| Example 62 | 122.7 | 3.5 | 1.3 |
| Example 64 | 130.8 | 3.8 | 2.6 |
| Example 65 | 123.8 | 3.6 | 2.4 |
| Example 66 | 122.1 | 3.1 | 2.5 |
| Example 68 | 130.8 | 3.8 | 2.6 |
| Example 69 | 126.7 | 3.7 | 16.0 |
| Example 70 | 120.0 | 3.5 | 36.0 |
| Example 71 | 127.3 | 3.8 | 9.8 |
| Example 73 | 101.3 | 2.9 | 8.2 |
| Example 74 | 104.2 | 3.0 | 5.6 |
| Example 76 | 101.8 | 2.9 | 19.6 |

Experimental Example 2

Oral Glucose Tolerance Test (OGTT)

The oral glucose tolerance test of the compounds according to the present invention was carried out according to the procedures disclosed in Andrikopoulos S, Blair A R, Deluca N, Fam B C, Proietto J, Am J Physiol Endocrinol Metab. 2008, Vol 295, E1323-1332. Briefly, male C57BL/6 mice at 8 to 9 weeks of age having 20 g to 25 g of body weight (Orient Bio Inc. Korea) were allowed to acclimatize to the surroundings (temperature: 20±2° C., humidity: 40-60%, light/dark cycle: 12 hours) for 1 week. During the acclimatization, the mice were given ad libitum access to feed and water. The mice were fasted from 18 hours before the test, except for allowing free access to water. After measuring the mice' body weights and blood sugar levels, they were divided into test groups so as to have similar blood sugar levels. The mice were orally administered with a mixture of test compound and the diluent (0.5% solution of MC1500 (Sigma)). At 30 minutes after the administration, the mice were also orally administered with 20% glucose solution in an amount of 0.1 ml per 10 g of body weight. The blood samples were taken from the tail vain at 0 (right before the administration of the glucose solution), 15, 30, 60, 90, and 120 minutes after the administration of the glucose solution; and the blood sugar levels thereof were measured with a blood glucose test meter (GlucoDr. AGM-3000, All Medicus Co. Ltd.). The graph for blood sugar level on time for each test compound was plotted from the respective blood sugar values; and then area under the curve (AUC$_{glucose}$) was determined. The inhibition rate of blood sugar (%) was calculated from the following formula. The results are shown in Table 3 below.

Inhibition rate of blood sugar (%)=[(AUC$_{glucose}$ of the negative control group−AUC$_{glucose}$ of the test group)/AUC$_{glucose}$ of the negative control group]×100

TABLE 3

|  | Inhibition rate of blood sugar (%) |
|---|---|
| Example 1 | 22.3 |
| Example 5 | 21.9 |
| Example 10 | 23.8 |
| Example 14 | 18.6 |
| Example 15 | 21.7 |
| Example 17 | 18.2 |
| Example 33 | 20.9 |
| Example 34 | 25.1 |
| Example 37 | 16.5 |
| Example 40 | 17.2 |
| Example 41 | 18.8 |
| Example 43 | 25.2 |
| Example 44 | 27.0 |
| Example 47 | 32.7 |
| Example 50 | 15.6 |
| Example 61 | 18.0 |
| Example 63 | 27.7 |
| Example 69 | 25.8 |
| Example 70 | 25.2 |
| Example 71 | 20.4 |
| Example 72 | 16.5 |

As shown in Tables 1 to 3, the compounds of the present invention activate GPR119, and therefore can be usefully applied for treating GPR119-mediated diseases, such as diabetes mellitus.

The invention claimed is:

1. A compound of Formula 1 or its pharmaceutically acceptable salt:

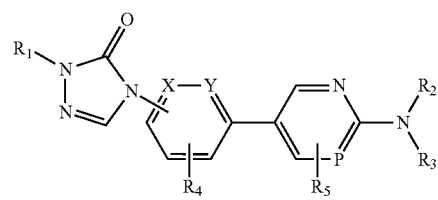

<Formula 1> wherein,

R$_1$ is hydrogen; a C$_1$-C$_6$ alkyl group optionally substituted with one or more substituents selected from the group consisting of hydroxy, halogen, C$_1$-C$_6$ alkoxy optionally substituted with C$_1$-C$_6$ alkoxy, C$_3$-C$_6$ cycloalkyl, cyano, 3- to 12-membered heterocyclic optionally substituted with one or more C$_1$-C$_6$ alkyls, —NR$_6$R$_7$, and

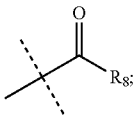

a $C_2$-$C_6$ alkenyl group; a $C_1$-$C_6$ alkylcarbonyl group; a $C_1$-$C_6$ alkoxycarbonyl group; or a 3- to 12-membered heterocyclic group optionally substituted with one or more substituents selected from the group consisting of $C_1$-$C_6$ alkyl, $C_2$-$C_6$ alkynyl, $C_1$-$C_6$ alkoxy, $C_3$-$C_6$ cycloalkyl, $C_1$-$C_6$ alkoxycarbonyl, $C_1$-$C_6$ alkylcarbonylamino, and $C_1$-$C_6$ alkylsulfonyl, $R_2$ is hydrogen or a $C_1$-$C_6$ alkyl group, $R_3$ is a $C_1$-$C_6$ alkyl group; or is cyclized with $R_2$ to form a 3- to 12-membered heterocyclic group, wherein the heterocyclic group may be optionally substituted with one or more substituents selected from the group consisting of $C_1$-$C_6$ alkyl optionally substituted with one or more halogens;

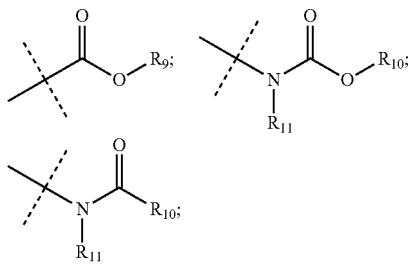

—$NR_{12}R_{13}$; 5- to 12-membered heteroaryl; and 3- to 12-membered heterocyclic (wherein, the heteroaryl or heterocyclic moiety may be optionally substituted with one or more $C_1$-$C_6$ alkyls optionally substituted with one or more halogens), $R_4$ and $R_5$ are, independently each other, hydrogen; a hydroxy group; a halogen group; a cyano group; a $C_1$-$C_6$ alkyl group optionally substituted with one or more halogens; a $C_1$-$C_6$ alkoxy group; or a mono- or di-$C_1$-$C_6$ alkylamino group, X and P are, independently each other, N or $CR_{14}$, Y is $CR_{14}$ or N, $R_6$ and $R_7$ are, independently each other, hydrogen; a $C_1$-$C_6$ alkyl group optionally substituted with one or more substituents selected from the group consisting of hydroxy, $C_1$-$C_6$ alkoxy and $C_3$-$C_6$ cycloalkyl; a $C_1$-$C_6$ alkylcarbonyl group; a $C_1$-$C_6$ alkoxycarbonyl group; or a $C_1$-$C_6$ alkylsulfonyl group, $R_8$ is a hydroxy group, a $C_1$-$C_6$ alkoxy group, an amino group, or a 3- to 12-membered heterocyclic group, $R_9$ is a $C_1$-$C_6$ alkyl group or a $C_2$-$C_6$ alkenyl group, $R_{10}$ is a $C_1$-$C_6$ alkyl group optionally substituted with one or more substituents selected from the group consisting of halogen, $C_3$-$C_6$ cycloalkyl, $C_1$-$C_6$ alkoxy, and 5- to 12-membered heteroaryl; a $C_2$-$C_8$ alkenyl group; a $C_3$-$C_6$ cycloalkyl group; a 6- to 12-membered aryl group optionally substituted with one or more substituents selected from the group consisting of halogen, $C_1$-$C_6$ alkyl optionally substituted with one or more halogens, and $C_1$-$C_6$ alkoxy; a 5- to 12-membered heteroaryl group; or a 3- to 12-membered heterocyclic group (wherein, the heteroaryl group or the heterocyclic group may be optionally substituted with one or more substituents selected from the group consisting of $C_1$-$C_6$ alkyl, nitro, hydroxy, and oxo), $R_{11}$ is hydrogen, a $C_1$-$C_6$ alkyl group, or a $C_2$-$C_6$ alkenyl group, $R_{12}$ is a $C_1$-$C_6$ alkylsulfonyl group; a $C_3$-$C_6$ cycloalkylsulfonyl group; a di-$C_1$-$C_6$ alkylaminosulfonyl group; a 5- to 12-membered heteroaryl group optionally substituted with $C_1$-$C_6$ alkyl; or a 3- to 12-membered heterocyclic group, $R_{13}$ is a $C_1$-$C_6$ alkyl group, $R_{14}$ is hydrogen; a halogen group; a cyano group; a nitro group; a $C_1$-$C_6$ alkyl group optionally substituted with one or more halogens; a $C_1$-$C_6$ alkoxy group; or a mono- or di-$C_1$-$C_6$ alkylamino group.

2. The compound or its pharmaceutically acceptable salt of claim 1, wherein $R_1$ is hydrogen; a $C_1$-$C_6$ alkyl group optionally substituted with one or more substituents selected from the group consisting of hydroxy, $C_1$-$C_6$ alkoxy, cyano, 3- to 12-membered heterocyclic optionally substituted with $C_1$-$C_6$ alkyl, —$NR_6R_7$, and

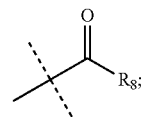

a $C_1$-$C_6$ alkoxycarbonyl group; or a 3- to 12-membered heterocyclic group.

3. The compound or its pharmaceutically acceptable salt of claim 2, wherein $R_6$ and $R_7$ is, independently each other, hydrogen; a $C_1$-$C_6$ alkyl group; a $C_1$-$C_6$ alkylcarbonyl group; a $C_1$-$C_6$ alkoxycarbonyl group; or a $C_1$-$C_6$ alkylsulfonyl group, and $R_8$ is be a $C_1$-$C_6$ alkoxy group, an amino group, or a 3- to 12-membered heterocyclic group.

4. The compound or its pharmaceutically acceptable salt of claim 1, wherein $R_2$ and $R_3$ is cyclized with each other to form a 3- to 12-membered heterocyclic group and wherein the heterocyclic group is optionally substituted with one or more substituents selected from the group consisting of $C_1$-$C_6$ alkyl optionally substituted with one or more halogens;

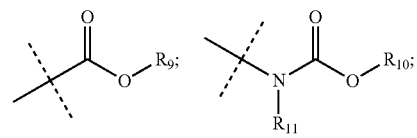

—$NR_{12}R_{13}$; and 5- to 12-membered heteroaryl (wherein, the heteroaryl moiety may be optionally substituted with $C_1$-$C_6$ alkyl optionally substituted with one or more halogens).

5. The compound or its pharmaceutically acceptable salt of claim 4, wherein $R_2$ and $R_3$ are cyclized with each other to form a piperazinyl group or a piperidinyl group.

6. The compound or its pharmaceutically acceptable salt of claim 5, wherein the piperazinyl group or the piperidinyl group is optionally substituted with one or more substituents selected from the group consisting of $C_1$-$C_6$ alkyl optionally substituted with one or more halogens;

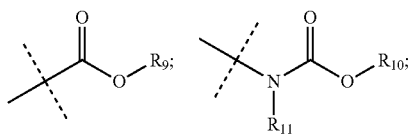

—NR₁₂R₁₃; and 5- to 12-membered heteroaryl selected from the group consisting of pyrimidyl, pyridyl, or 1,2,4-oxadiazolyl (wherein, the heteroaryl moiety may be optionally substituted with $C_1$-$C_6$ alkyl optionally substituted with one or more halogens).

7. The compound or its pharmaceutically acceptable salt of claim 6, wherein
$R_9$ is a $C_1$-$C_6$ alkyl group,
$R_{10}$ is a $C_1$-$C_6$ alkyl group or a $C_2$-$C_6$ alkenyl group,
$R_{11}$ is a $C_1$-$C_6$ alkyl group,
$R_{12}$ is a $C_1$-$C_6$ alkylsulfonyl group or a 5- to 12-membered heteroaryl group optionally substituted with $C_1$-$C_6$ alkyl, and
$R_{13}$ is a $C_1$-$C_6$ alkyl group.

8. The compound or its pharmaceutically acceptable salt of claim 1, wherein $R_4$ and $R_5$ is, independently each other, hydrogen; a halogen group; a cyano group; or a $C_1$-$C_6$ alkyl group optionally substituted with one or more halogens.

9. The compound or its pharmaceutically acceptable salt of claim 1, wherein X and P is, independently each other, N or $CR_{14}$; and $R_{14}$ is hydrogen or a halogen group.

10. The compound or its pharmaceutically acceptable salt of claim 1, wherein Y is $CR_{14}$; and $R_{14}$ is hydrogen or a halogen group.

11. The compound or its pharmaceutically acceptable salt of claim 1, which is selected from the group consisting of:
(S)-tert-butyl 4-(5-(3-fluoro-4-(1-methyl-5-oxo-1H-1,2,4-triazol-4(5H)-yl)phenyl)pyrimidin-2-yl)-3-methylpiperazin-1-carboxylate;
(S)-tert-butyl 4-(5-(3-fluoro-4-(5-oxo-1-propyl-1H-1,2,4-triazol-4(5H)-yl)phenyl)pyrimidin-2-yl)-3-methylpiperazin-1-carboxylate;
(S)-tert-butyl 4-(5-(3-fluoro-4-(1-isopropyl-5-oxo-1H-1,2,4-triazol-4(5H)-yl)phenyl)pyrimidin-2-yl)-3-methylpiperazin-1-carboxylate;
(S)-tert-butyl 4-(5-(3-fluoro-4-(1-(2-methoxyethyl)-5-oxo-1H-1,2,4-triazol-4(5H)-yl)phenyl)pyrimidin-2-yl)-3-methylpiperazin-1-carboxylate;
(S)-tert-butyl 4-(3-cyano-5-(3-fluoro-4-(5-oxo-1-propyl-1H-1,2,4-triazol-4(5H)-yl)phenyl)pyridin-2-yl)-3-methylpiperazin-1-carboxylate;
(S)-tert-butyl 4-(5-(3-fluoro-4-(5-oxo-1-propyl-1H-1,2,4-triazol-4(5H)-yl)phenyl)-3-(trifluoromethyl)pyridin-2-yl)-3-methylpiperazin-1-carboxylate;
(S)-4-(4-(2-(4-(5-ethylpyrimidin-2-yl)-2-methylpiperazin-1-yl)pyrimidin-5-yl)-2-fluorophenyl)-1-methyl-1H-1,2,4-triazol-5(4H)-one;
(S)-4-(2-fluoro-4-(2-(2-methyl-4-(5-(trifluoromethyl)pyridin-2-yl)piperazin-1-yl)pyrimidin-5-yl)phenyl)-1-methyl-1H-1,2,4-triazol-5(4H)-one;
(S)-2-(4-(5-ethylpyrimidin-2-yl)-2-methylpiperazin-1-yl)-5-(3-fluoro-4-(1-methyl-5-oxo-1H-1,2,4-triazol-4(5H)-yl)phenyl)nicotinonitrile;
(S)-5-(4-(1-(2-(diethylamino)ethyl)-5-oxo-1H-1,2,4-triazol-4(5H)-yl)-3-fluorophenyl)-2-(4-(5-ethylpyrimidin-2-yl)-2-methylpiperazin-1-yl)nicotinonitrile;
(S)-2-(4-(5-ethylpyrimidin-2-yl)-2-methylpiperazin-1-yl)-5-(3-fluoro-4-(1-(2-hydroxy-2-methylpropyl)-5-oxo-1H-1,2,4-triazol-4(5H)-yl)phenyl)nicotinonitrile;
(S)-2-(4-(5-ethylpyrimidin-2-yl)-2-methylpiperazin-1-yl)-5-(3-fluoro-4-(1-isobutyl-5-oxo-1H-1,2,4-triazol-4(5H)-yl)phenyl)nicotinonitrile;
(S)-methyl 2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)acetate;
(S)-2-(4-(5-ethylpyrimidin-2-yl)-2-methylpiperazin-1-yl)-5-(3-fluoro-4-(5-oxo-1-(2-pyrrolidin-1-yl)ethyl)-1H-1,2,4-triazol-4(5H)-yl)phenyl)nicotinonitrile;
(S)-2-(4-(5-ethylpyrimidin-2-yl)-2-methylpiperazin-1-yl)-5-(3-fluoro-4-(1-(2-morpholinoethyl)-5-oxo-1H-1,2,4-triazol-4(5H)-yl)phenyl)nicotinonitrile;
(S)-tert-butyl 2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethylcarbamate;
(S)-5-(4-(1-(2-aminoethyl)-5-oxo-1H-1,2,4-triazol-4(5H)-yl)-3-fluorophenyl)-2-(4-(5-ethylpyrimidin-2-yl)-2-methylpiperazin-1-yl)nicotinonitrile hydrochloride;
(S)-5-(4-(1-(cyanomethyl)-5-oxo-1H-1,2,4-triazol-4(5H)-yl)-3-fluorophenyl)-2-(4-(5-ethylpyrimidin-2-yl)-2-methylpiperazin-1-yl)nicotinonitrile;
(S)-tert-butyl 2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethyl (isopropyl)carbamate;
(S)-2-(4-(5-ethylpyrimidin-2-yl)-2-methylpiperazin-1-yl)-5-(3-fluoro-4-(1-(2-(isopropylamino)ethyl)-5-oxo-1H-1,2,4-triazol-4(5H)-yl)phenyl)nicotinonitrile hydrochloride;
(S)-2-(4-(5-ethylpyrimidin-2-yl)-2-methylpiperazin-1-yl)-5-(3-fluoro-4-(5-oxo-1H-1,2,4-triazol-4(5H)-yl)phenyl)nicotinonitrile;
(S)-2-(4-(5-ethylpyrimidin-2-yl)-2-methylpiperazin-1-yl)-5-(3-fluoro-4-(1-(methoxymethyl)-5-oxo-1H-1,2,4-triazol-4(5H)-yl)phenyl)nicotinonitrile;
(S)—N-(2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethyl)methanesulfonamide;
(S)-ethyl 4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-carboxylate;
(S)-5-(4-(1-(2-cyano-2-methylpropyl)-5-oxo-1H-1,2,4-triazol-4(5H)-yl)-3-fluorophenyl)-2-(4-(5-ethylpyrimidin-2-yl)-2-methylpiperazin-1-yl)nicotinonitrile;
(S)—N-(2-(4-(4-(5-cyano-6-(4-(5-ethylpyrimidin-2-yl)-2-methylpiperazin-1-yl)pyridin-3-yl)-2-fluorophenyl)-5-oxo-4,5-dihydro-1H-1,2,4-triazol-1-yl)ethyl)acetamide;
(S)-2-(4-(5-ethylpyrimidin-2-yl)-2-methylpiperazin-1-yl)-5-(3-fluoro-4-(1-((4-methylpiperazin-1-yl)methyl)-5-oxo-1H-1,2,4-triazol-4(5H)-yl)phenyl)nicotinonitrile;
(S)-2-(4-(5-ethylpyrimidin-2-yl)-2-methylpiperazin-1-yl)-5-(3-fluoro-4-(5-oxo-1-(pyrrolidin-1-ylmethyl)-1H-1,2,4-triazol-4(5H)-yl)phenyl)nicotinonitrile;
(S)-5-(2,5-difluoro-4-(1-methyl-5-oxo-1H-1,2,4-triazol-4(5H)-yl)phenyl)-2-(4-(5-ethylpyrimidin-2-yl)-2-methylpiperazin-1-yl)nicotinonitrile;
2-(4-(5-ethylpyrimidin-2-yl)piperazin-1-yl)-5-(3-fluoro-4-(1-isopropyl-5-oxo-1H-1,2,4-triazol-4(5H)-yl)phenyl)nicotinonitrile;
5-(4-(1-(2-methoxyethyl)-5-oxo-1H-1,2,4-triazol-4(5H)-yl)-3-fluorophenyl)-2-(4-(5-ethylpyrimidin-2-yl)piperazin-1-yl)nicotinonitrile;

2-(4-(5-ethylpyrimidin-2-yl)piperazin-1-yl)-5-(3-fluoro-4-(1-neopentyl-5-oxo-1H-1,2,4-triazol-4(5H)-yl)phenyl)nicotinonitrile;

(R)-2-(4-(5-ethylpyrimidin-2-yl)piperazin-1-yl)-5-(3-fluoro-4-(5-oxo-1-(tetrahydrofuran-3-yl)-1H-1,2,4-triazol-4(5H)-yl)phenyl)nicotinonitrile;

(R)-2-(4-(5-ethylpyrimidin-2-yl)piperazin-1-yl)-5-(3-fluoro-4-(5-oxo-1-(pyrrolidin-3-yl)-1H-1,2,4-triazol-4(5H)-yl)phenyl)nicotinonitrile;

2-(4-(5-ethylpyrimidin-2-yl)piperazin-1-yl)-5-(3-fluoro-4-(1-(morpholinomethyl)-5-oxo-1H-1,2,4-triazol-4(5H)-yl)phenyl)nicotinonitrile;

(S)-5-(4-(1-(2,3-dihydroxypropyl)-5-oxo-1H-1,2,4-triazol-4(5H)-yl)-3-fluorophenyl)-2-(4-(5-ethylpyrimidin-2-yl)piperazin-1-yl)nicotinonitrile;

2-(4-(5-ethylpyrimidin-2-yl)piperazin-1-yl)-5-(3-fluoro-4-(5-oxo-1-(2-oxo-2-(pyrrolidin-1-yl)ethyl)-1H-1,2,4-triazol-4(5H)-yl)phenyl)nicotinonitrile;

2-(4-(5-ethylpyrimidin-2-yl)piperazin-1-yl)-5-(2-fluoro-4-(1-isopropyl-5-oxo-1H-1,2,4-triazol-4(5H)-yl)phenyl)nicotinonitrile;

2-(4-(5-ethylpyrimidin-2-yl)piperazin-1-yl)-5-(4-(1-methyl-5-oxo-1H-1,2,4-triazol-4(5H)-yl)phenyl)nicotinonitrile;

2-(4-(5-ethylpyrimidin-2-yl)piperazin-1-yl)-5-(4-(1-(2-methoxyethyl)-5-oxo-1H-1,2,4-triazol-4(5H)-yl)phenyl)nicotinonitrile;

(R)-2-(4-(5-ethylpyrimidin-2-yl)piperazin-1-yl)-5-(4-(5-oxo-1-(tetrahydrofuran-3-yl)-1H-1,2,4-triazol-4(5H)-yl)phenyl)nicotinonitrile;

(S)-2-(4-(5-ethylpyrimidin-2-yl)piperazin-1-yl)-5-(4-(5-oxo-1-(pyrrolidin-3-yl)-1H-1,2,4-triazol-4(5H)-yl)phenyl)nicotinonitrile;

2-(4-(5-ethylpyrimidin-2-yl)piperazin-1-yl)-5-(3-fluoro-4-(1-isopropyl-5-oxo-1H-1,2,4-triazol-4(5H)-yl)phenyl)nicotinonitrile hydrochloride;

2-(4-(5-ethylpyrimidin-2-yl)piperazin-1-yl)-5-(3-fluoro-4-(1-isopropyl-5-oxo-1H-1,2,4-triazol-4(5H)-yl)phenyl)nicotinonitrile sulfonate;

5-(3-fluoro-4-(1-methyl-5-oxo-1H-1,2,4-triazol-4(5H)-yl)phenyl)-2-(4-(5-isopropyl-1,2,4-oxadiazol-3-yl)piperazin-1-yl)nicotinonitrile;

5-(3-fluoro-4-(1-isopropyl-5-oxo-1H-1,2,4-triazol-4(5H)-yl)phenyl)-2-(4-(5-isopropyl-1,2,4-oxadiazol-3-yl)piperazin-1-yl)nicotinonitrile;

(S)-5-(3-fluoro-4-(5-oxo-1-(tetrahydrofuran-3-yl)-1H-1,2,4-triazol-4(5H)-yl)phenyl)-2-(4-(5-isopropyl-1,2,4-oxadiazol-3-yl)piperazin-1-yl)nicotinonitrile;

2-(4-(5-isopropyl-1,2,4-oxadiazol-3-yl)piperazin-1-yl)-5-(4-(1-(methoxymethyl)-5-oxo-1H-1,2,4-triazol-4(5H)-yl)phenyl)nicotinonitrile;

5-(3-fluoro-4-(5-oxo-1-propyl-1H-1,2,4-triazol-4(5H)-yl)phenyl)-2-(4-(5-isopropyl-1,2,4-oxadiazol-3-yl)piperazin-1-yl)nicotinonitrile hydrochloride;

tert-butyl 4-(5-(3-fluoro-4-(5-oxo-1-propyl-1H-1,2,4-triazol-4(5H)-yl)phenyl)pyridin-2-yl)-3-(trifluoromethyl)piperazin-1-carboxylate;

tert-butyl 4-(5-(3-fluoro-4-(1-isopropyl-5-oxo-1H-1,2,4-triazol-4(5H)-yl)phenyl)pyridin-2-yl)-3-(trifluoromethyl)piperazin-1-carboxylate;

4-(2-fluoro-4-(6-(2-(trifluoromethyl)-4-(5-(trifluoromethyl)pyridin-2-yl)piperazin-1-yl)pyridin-3-yl)phenyl)-1-propyl-1H-1,2,4-triazol-5(4H)-one;

4-(4-(6-(4-(5-ethylpyrimidin-2-yl)-2-(trifluoromethyl)piperazin-1-yl)pyridin-3-yl)-2-fluorophenyl)-1-propyl-1H-1,2,4-triazol-5(4H)-one;

tert-butyl 1-(5-(3-fluoro-4-(5-oxo-1-propyl-1H-1,2,4-triazol-4(5H)-yl)phenyl)pyrimidin-2-yl)piperidin-4-yl(methyl)carbamate;

N-(1-(5-(3-fluoro-4-(5-oxo-1-propyl-1H-1,2,4-triazol-4(5H)-yl)phenyl)pyrimidin-2-yl)piperidin-4-yl)-N-methylpropan-1-sulfonamide;

tert-butyl ethyl(1-(5-(3-fluoro-4-(5-oxo-1-propyl-1H-1,2,4-triazol-4(5H)-yl)phenyl)pyrimidin-2-yl)piperidin-4-yl)carbamate;

tert-butyl 1-(3-fluoro-5-(3-fluoro-4-(5-oxo-1-propyl-1H-1,2,4-triazol-4(5H)-yl)phenyl)pyridin-2-yl)piperidin-4-yl(methyl)carbamate;

tert-butyl 1-(3-cyano-5-(3-fluoro-4-(1-isopropyl-5-oxo-1H-1,2,4-triazol-4(5H)-yl)phenyl)pyridin-2-yl)piperidin-4-yl(methyl)carbamate;

prop-1-en-2-yl 1-(3-cyano-5-(3-fluoro-4-(1-isopropyl-5-oxo-1H-1,2,4-triazol-4(5H)-yl)phenyl)pyridin-2-yl)piperidin-4-yl(methyl)carbamate;

2-(4-((5-ethylpyrimidin-2-yl)(methyl)amino)piperidin-1-yl)-5-(3-fluoro-4-(1-isopropyl-5-oxo-1H-1,2,4-triazol-4(5H)-yl)phenyl)nicotinonitrile;

tert-butyl 1-(3-cyano-5-(4-(1-(2-(diethylamino)ethyl)-5-oxo-1H-1,2,4-triazol-4(5H)-yl)-3-fluorophenyl)pyridin-2-yl)piperidin-4-yl(methyl)carbamate;

5-(3-fluoro-4-(5-oxo-1-propyl-1H-1,2,4-triazol-4(5H)-yl)phenyl)-2-(4-(3-isopropyl-1,2,4-oxadiazol-5-yl)piperidin-1-yl)nicotinonitrile;

5-(4-(1-(2-(diethylamino)ethyl)-5-oxo-1H-1,2,4-triazol-4(5H)-yl)-3-fluorophenyl)-2-(4-(3-isopropyl-1,2,4-oxadiazol-5-yl)piperidin-1-yl)nicotinonitrile;

5-(3-fluoro-4-(5-oxo-1-(pyrrolidin-1-ylmethyl)-1H-1,2,4-triazol-4(5H)-yl)phenyl)-2-(4-(3-isopropyl-1,2,4-oxadiazol-5-yl)piperidin-1-yl)nicotinonitrile;

5-(4-(1-ethyl-5-oxo-1H-1,2,4-triazol-4(5H)-yl)phenyl)-2-(4-(3-isopropyl-1,2,4-oxadiazol-5-yl)piperidin-1-yl)nicotinonitrile;

5-(3-fluoro-4-(5-oxo-1-propyl-1H-1,2,4-triazol-4(5H)-yl)phenyl)-2-(4-(5-isopropyl-1,2,4-oxadiazol-3-yl)piperidin-1-yl)nicotinonitrile;

5-(4-(1-(2-(diethylamino)ethyl)-5-oxo-1H-1,2,4-triazol-4(5H)-yl)-3-fluorophenyl)-2-(4-(5-isopropyl-1,2,4-oxadiazol-3-yl)piperidin-1-yl)nicotinonitrile;

5-(3-fluoro-4-(5-oxo-1-(pyrrolidin-1-ylmethyl)-1H-1,2,4-triazol-4(5H)-yl)phenyl)-2-(4-(3-isopropyl-1,2,4-oxadiazol-5-yl)piperidin-1-yl)nicotinonitrile;

2-(4-(5-isopropyl-1,2,4-oxadiazol-3-yl)piperidin-1-yl)-5-(4-(1-(2-methoxyethyl)-5-oxo-1H-1,2,4-triazol-4(5H)-yl)phenyl)nicotinonitrile;

(R)-2-(4-(5-isopropyl-1,2,4-oxadiazol-3-yl)piperidin-1-yl)-5-(4-(5-oxo-1-(tetrahydrofuran-3-yl)-1H-1,2,4-triazol-4(5H)-yl)phenyl)nicotinonitrile;

(S)-2-(4-(5-isopropyl-1,2,4-oxadiazol-3-yl)piperidin-1-yl)-5-(4-(5-oxo-1-(tetrahydrofuran-3-yl)-1H-1,2,4-triazol-4(5H)-yl)phenyl)nicotinonitrile;

2-(4-(4-(5-cyano-6-(4-(5-isopropyl-1,2,4-oxadiazol-3-yl)piperidin-1-yl)pyridin-3-yl)phenyl)-5-oxo-4,5-dihydro-1H-1,2,4-triazol-1-yl)acetamide;

5-(4-(1-isopropyl-5-oxo-1H-1,2,4-triazol-4(5H)-yl)phenyl)-2-(4-(5-(trifluoromethyl)-1,3,4-oxadiazol-2-yl)piperidin-1-yl)nicotinonitrile;

5-(3-fluoro-4-(1-isopropyl-5-oxo-1H-1,2,4-triazol-4(5H)-yl)phenyl)-2-(4-(5-(trifluoromethyl)-1,3,4-oxadiazol-2-yl)piperidin-1-yl)nicotinonitrile;

(S)-5-(3-fluoro-4-(5-oxo-1-(tetrahydrofuran-3-yl)-1H-1,2,4-triazol-4(5H)-yl)phenyl)-2-(4-(5-(trifluoromethyl)-1,3,4-oxadiazol-2-yl)piperidin-1-yl)nicotinonitrile;

(S)-5-(3-fluoro-4-(5-oxo-1-(tetrahydrofuran-3-yl)-1H-1,
2,4-triazol-4(5H)-yl)phenyl)-2-(4-(5-(trifluoromethyl)-
1,3,4-oxadiazol-2-yl)piperidin-1-yl)nicotinonitrile;

5-(4-(1-isopropyl-5-oxo-1H-1,2,4-triazol-4(5H)-yl)phe-
nyl)-2-(4-(5-(trifluoromethyl)-1,3,4-oxadiazol-2-yl)
piperazin-1-yl)nicotinonitrile;

5-(3-fluoro-4-(1-isopropyl-5-oxo-1H-1,2,4-triazol-4
(5H)-yl)phenyl)-2-(4-(5-(trifluoromethyl)-1,3,4-oxadi-
azol-2-yl)piperazin-1-yl)nicotinonitrile;

(S)-5-(3-fluoro-4-(5-oxo-1-(tetrahydrofuran-3-yl)-1H-1,
2,4-triazol-4(5H)-yl)phenyl)-2-(4-(5-(trifluoromethyl)-
1,3,4-oxadiazol-2-yl)piperazin-1-yl)nicotinonitrile;
and 5-(3-fluoro-4-(1-(2-methoxyethyl)-5-oxo-1H-1,2,4-tri-
azol-4(5H)-yl)phenyl)-2-(4-(5-(trifluoromethyl)-1,3,4-
oxadiazol-2-yl)piperazin-1-yl)nicotinonitrile.

12. A pharmaceutical composition for treating diabetes mellitus, comprising a therapeutically effective amount of the compound or its pharmaceutically acceptable salt according to claim 1; and a pharmaceutically acceptable carrier.

13. A method for treating diabetes mellitus in a mammal, including a human, in need thereof, which comprises administering to such mammal a therapeutically effective amount of the compound or its pharmaceutically acceptable salt according to claim 1.

* * * * *